US012465690B2

(12) United States Patent
San Solo et al.

(10) Patent No.: US 12,465,690 B2
(45) Date of Patent: Nov. 11, 2025

(54) INTEGRATED DISINFECTION DEVICE

(71) Applicant: Becton, Dickinson and Company, Franklin Lakes, NJ (US)

(72) Inventors: Shoshana San Solo, New York, NY (US); Nicholas Erekovcanski, Butler, NJ (US); Paul P. Marici, Piscataway, NJ (US); Richard Timmers, Westwood, NJ (US); Gheorghe Cojocariu, Bridgewater, NJ (US); Bradley Tonniges, Columbus, NE (US); Steve Fitz, Columbus, NE (US); Gregory Anderson, Columbus, NE (US); Gerald Leon Bonczynski, Columbus, NE (US); Samantha R. Garrabrant, Fair Lawn, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 221 days.

(21) Appl. No.: 18/379,719

(22) Filed: Oct. 13, 2023

(65) Prior Publication Data

US 2024/0033437 A1 Feb. 1, 2024

Related U.S. Application Data

(62) Division of application No. 16/923,414, filed on Jul. 8, 2020, now Pat. No. 11,786,663.

(60) Provisional application No. 62/883,448, filed on Aug. 6, 2019, provisional application No. 62/873,451, filed on Jul. 12, 2019.

(51) Int. Cl.
*A61M 5/31* (2006.01)

(52) U.S. Cl.
CPC ....... *A61M 5/31* (2013.01); *A61M 2005/3104* (2013.01); *A61M 2005/3117* (2013.01)

(58) Field of Classification Search
CPC ............ A61M 5/31; A61M 2005/3104; A61M 2005/3117
See application file for complete search history.

(56) References Cited

U.S. PATENT DOCUMENTS

| | | | | |
|---|---|---|---|---|
| 4,711,363 | A | 12/1987 | Marino | |
| 4,738,376 | A | 4/1988 | Markus | |
| 5,496,288 | A | 3/1996 | Sweeney | |
| 8,388,894 | B2 * | 3/2013 | Colantonio ......... | A61M 39/162 604/905 |

(Continued)

FOREIGN PATENT DOCUMENTS

| | | | |
|---|---|---|---|
| CA | 2523133 | C | 2/2013 |
| CN | 101541361 | A | 9/2009 |

(Continued)

OTHER PUBLICATIONS

"Final Office Action in U.S. Appl. No. 16/253,683 dated Dec. 23, 2020, 9 pages".

(Continued)

*Primary Examiner* — Dung T Ulsh
(74) *Attorney, Agent, or Firm* — Servilla Whitney LLC

(57) ABSTRACT

Syringe tip caps are described herein. Such syringe tip caps may include a cup, a cap, a locking feature, a peelable seal and an absorbent material. The cap having locking features and a chamber appropriately sized to adapt to and interlock with an annular wall of the cup.

8 Claims, 65 Drawing Sheets

(56) References Cited

U.S. PATENT DOCUMENTS

| | | | | |
|---|---|---|---|---|
| 8,715,231 | B2 | 5/2014 | Woehr | |
| 8,777,504 | B2 | 7/2014 | Shaw et al. | |
| 9,192,449 | B2 | 11/2015 | Kerr et al. | |
| 10,166,381 | B2 * | 1/2019 | Gardner | A61M 39/162 |
| 2004/0039341 | A1 | 2/2004 | Ranalletta | |
| 2008/0010766 | A1 | 1/2008 | Kaufman et al. | |
| 2010/0050351 | A1 | 3/2010 | Colantonio et al. | |
| 2011/0046603 | A1 | 2/2011 | Felsovalyi et al. | |
| 2012/0039764 | A1 | 2/2012 | Solomon et al. | |
| 2012/0109073 | A1 | 5/2012 | Anderson et al. | |
| 2012/0123386 | A1 | 5/2012 | Tsals | |
| 2013/0085474 | A1 | 4/2013 | Charles et al. | |
| 2013/0171030 | A1 | 7/2013 | Ferlic et al. | |
| 2014/0366914 | A1 | 12/2014 | Kerr et al. | |
| 2015/0011936 | A1 | 1/2015 | Okihara et al. | |
| 2015/0374968 | A1 * | 12/2015 | Solomon | A61M 39/162 604/535 |
| 2018/0200145 | A1 | 7/2018 | Sanders et al. | |
| 2018/0361003 | A1 * | 12/2018 | Dombrowski | A61M 39/162 |
| 2020/0269033 | A1 * | 8/2020 | Corrigan | A61M 39/20 |
| 2021/0346672 | A1 * | 11/2021 | Grant | A61M 39/18 |

FOREIGN PATENT DOCUMENTS

| | | | |
|---|---|---|---|
| CN | 102448502 | A | 5/2012 |
| CN | 214388299 | U | 10/2021 |
| DE | 20017013 | U1 | 12/2000 |
| DE | 10247963 | A1 | 5/2004 |
| EP | 2606930 | A1 | 6/2013 |
| EP | 2832391 | A1 | 2/2015 |
| EP | 3275490 | A1 | 1/2018 |
| GB | 2518646 | A | 4/2015 |
| JP | 2004208740 | A | 7/2004 |
| JP | 2008253775 | A | 10/2008 |
| JP | 2009526241 | A | 7/2009 |
| JP | 2014528288 | A | 10/2014 |
| JP | 2014532517 | A | 12/2014 |
| WO | 200024442 | A1 | 5/2000 |
| WO | 200224551 | A1 | 3/2002 |
| WO | 2012144026 | A1 | 10/2012 |
| WO | 2018237090 | A1 | 12/2018 |
| WO | 2019147906 | A1 | 8/2019 |

OTHER PUBLICATIONS

“PCT International Search Report and Written Opinion in PCT/US2020/041097 dated Oct. 27, 2020, 18 pages”.

“PCT International Search Report and Written Opinion in PCT/US2020/041311 dated Sep. 30, 2020, 16 pages”.

“PCT International Search Report and Written Opinion in PCT/US2020/041312 dated Oct. 19, 2020, 11 pages”.

“Ruhof Dry Sponges”, Ruhof, Sep. 30, 2016, https://www.ruhof.com/products/ruhof-dry-sponges (Year: 2016).

* cited by examiner

INTEGRATED DISINFECTION DEVICE

CROSS-REFERENCE TO RELATED APPLICATIONS

This application is a divisional of U.S. patent application Ser. No. 16/923,414, filed on Jul. 8, 2020, now U.S. Pat. No. 11,786,663 issued Oct. 17, 2023, claims priority under 35 U.S.C. § 119(e) to U.S. Provisional Application No. 62/873,451, filed Jul. 12, 2019, and U.S. Provisional Application No. 62/883,448 filed Aug. 6, 2019, the disclosures of which are incorporated herein by reference in their entireties.

TECHNICAL FIELD

The present disclosure generally relates to a pre-filled syringe assembly having an integrated disinfection unit assembled to a syringe tip cap by flexible features to a physical barrier for securely sealing the tip of a hypodermic syringe barrel, preventing contact of the syringe tip with the surrounding non-sterile environment and providing for a means of mechanical and chemical disinfection.

BACKGROUND

Vascular access devices (VADs) are commonly used therapeutic devices, which include intravenous (IV) catheters, syringes, extension sets, stop cocks, tubing, high pressure extension tubing, and needleless access devices. The operation of VADs is often compromised or completely prevented by the occurrence of thrombus formation. Thrombosis is the development of a blood clot within a vessel and/or vascular access device. If not properly maintained or if exposed to a non-sterile environment, the VADs can become contaminated, sealed with blood clots or spread infection. To ensure VADs are used properly and do not become sealed or infected, protocols to ensure sterile practice have been developed. These protocols include sterilizing the VAD and flushing the catheter with a flush solution. Catheters are flushed using syringe assemblies filled with various fluids. In some cases, different fluids are injected sequentially in accordance with the protocol. For example, a saline solution followed by an anticoagulant such as heparin. The size of the syringe used to flush intravenous (I.V.) lines varies by various factors including the size and length of the catheter. Typically syringes of 1 ml, 3 ml, 5 ml and 10 ml volume are used. VAD protocols usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections.

Conventional flush syringes have a barrel with a luer tip at one end which is exposed to the non-sterile environment once the syringe tip is removed from packaging thus providing an opportunity for undesired contamination.

Current "recommended practice" for aseptic IV line maintenance and IV drug delivery practices require adherence to a stepwise process referred to as "SASH." During the first step of the process, the clinician cleans/disinfects (generally with an alcohol swab) the VAD connector. Second, a syringe containing saline is used to flush the IV line or catheter (Saline flush), and then the VAD connector is disinfected a second time. Third, the fluid or pharmaceutical therapy is administered through the IV line or catheter (Administer therapy), the VAD connector is disinfected a third time, followed by a second Saline flush step. The final step, which is dependent upon the patient's need and institutional policy, is a final disinfection of the VAD connector followed by a Heparin lock step, where a small amount of heparin is injected into the IV line or catheter to prevent the formation of thrombi or blood clots. A separate disinfecting cap may be used to sterile the hub of the VAD which after sterilization is performed the disinfecting cap is discarded. At the conclusion of this tedious stepwise process, the inlet port of the VAD connector is left exposed to the environment. This "recommended practice" requires disinfecting the VAD connector after each access makes IV line maintenance a very burdensome and time consuming process. Because the process is so cumbersome, clinicians very rarely implement this "recommended practice" in its entirety, and, thus, patients are exposed to the risk of contracting CRBSIs. Microorganisms populate exposed connector inlet surfaces, and, when the "recommended practice" is not adhered to, the microorganisms can enter the IV line during flushing. Furthermore, blood reflux into the IV line or catheter can cause clot formation inside the lines, and microorganisms from the connector inlet surfaces can colonize blood clots inside the lines and infect the patients during flushing.

Current practice requires users to obtain a separate flush syringe and a separate disinfection unit product. There is a need, therefore, for an integrated disinfection unit assembled to a syringe that promotes compliance with aseptic technique by eliminating the additional swabbing and disinfecting steps while reducing the number of separate flushing and disinfecting apparatuses used in current practice.

SUMMARY

One aspect of the present disclosure pertains to an integrated disinfection device having a cup having an integral body, an annular wall having a length L(a) extending from the closed end to an open end defining a chamber; the annular wall having an exterior wall surface and an interior wall surface; a plurality of clips disposed on the exterior wall surface of the annular wall, the clips protruding outwards from the exterior wall surface and being adjacent to the closed end of the cup; a plurality of inward protrusions adjacent to the interior wall surface of the chamber of the cup; a cap having an integral body, an annular wall having a length L(a) extending from the bottom end to an top end defining a chamber; the chamber is appropriately sized to adapt to the annular wall of the cup; a mating surface dispose on the chamber; and a plurality of locking holes disposed on the annular wall.

In one or more embodiments, the plurality of clips may be one-way flexing clips.

In one or more embodiments, the locking holes are coincident with the mating surface of the chamber.

In one or more embodiments, the inward protrusions are shaped as a hex fitting.

In one or more embodiments, a bottom surface of the locking holes coincides with the mating surface of the chamber.

In one or more embodiments, the cap includes a connection element.

In one or more embodiments, the connection element may be a luer slip connection or a luer lock connection.

A second aspect of the present disclosure pertains to an integrated disinfection device including a cup having an integral body, an annular wall having a length L(a) extending from the closed end to an open end defining a chamber;

the annular wall having an exterior wall surface and an interior wall surface; a plurality of alignment teeth disposed on the annular wall; a plurality of inward protrusions disposed on the chamber of the cup adjacent to the interior wall surface; a plurality of locking tabs; a cap having an integral body, an annular wall having a length L(a) extending from the bottom end to an top end defining a chamber; the chamber is appropriately sized to adapt to the annular wall of the cup a plurality of alignment teeth face disposed on the interior wall surface of the annular wall; a mating surface dispose on the chamber; and a locking hole disposed in the center of the mating surface.

In one or more embodiments, the locking tabs are perpendicular to a plane coincident to the closed end of the cup.

In one or more embodiments, the locking tabs include a harpoon-shaped lip.

In one or more embodiments, the locking tabs are disposed in the center of the closed end.

In one or more embodiments, the alignment teeth are spaced evenly along the interior wall surface of the annular wall.

In one or more embodiments, the cap includes a connection element.

In one or more embodiments, the connection element may be a luer slip connection or a luer lock connection.

A third aspect of the present disclosure pertains to an integrated disinfection device including a cup having an integral body, an annular wall having a length L(a) extending from the closed end to an open end defining a chamber; the annular wall having an exterior wall surface and an interior wall surface; a plurality of female receivers disposed on opposite sides of the interior wall surface; a cap having an integral body, an annular wall having a length L(a) extending from the bottom end to an top end defining a chamber; and a plurality of flexing tabs disposed on perpendicular to the closed end.

In one or more embodiments, the flexing tabs are harpoon-shaped.

In one or more embodiments, the cap includes a connection element. In one or more embodiments, the connection element may be a luer slip connection or a luer lock connection.

A fourth aspect of the present disclosure pertains to an integrated disinfection device including a cup having an integral body, an annular wall having a length L(a) extending from the closed end to an open end defining a chamber; the annular wall having an exterior wall surface and an interior wall surface; a plurality of protrusions disposed on the interior wall surface; a mating surface dispose on the chamber having a male slot that protrudes out perpendicularly from the mating surface in the opposite direction of the top end of the annular wall; a cap having an integral body, an annular wall having a length L(b) extending from the bottom end to an top end defining a chamber; a mating protrusion having a peripheral rim disposed on the cap and a female slot.

In one or more embodiments, the cap includes a connection element. In one or more embodiments, the connection element may be a luer slip connection or a luer lock connection.

A fifth aspect of the present disclosure pertains to an integrated disinfection device including a cup having an integral body, an annular wall having a length L(a) extending from the closed end to an open end defining a chamber; the annular wall having an exterior wall surface and an interior wall surface; a plurality of alignment teeth disposed on the annular wall; a cap having an integral body, an annular wall having a length L(a) extending from the bottom end to an top end defining a chamber; the chamber is appropriately sized to adapt to the annular wall of the cup a mating surface dispose on the chamber; and an annular snap joint disposed on the exterior wall surface of the annular wall.

In one or more embodiments, the cap includes a connection element. In one or more embodiments, the connection element may be a luer slip connection or a luer lock connection.

A sixth aspect of the present disclosure pertains to an integrated disinfection device including a cup having an integral body, an annular wall having a length L(a) extending from the closed end to an open end defining a chamber; the annular wall having an exterior wall surface and an interior wall surface; a cap having an integral body, an annular wall having a length L(a) extending from the bottom end to an top end defining a chamber; the chamber is appropriately sized to adapt to the annular wall of the cup; a plurality of locking holes disposed on the annular wall; a plurality of alignment teeth disposed on the interior wall surface of the annular wall; and a plurality of knobs disposed on the exterior wall surface of the annular wall.

In one or more embodiments, the cap includes a connection element. In one or more embodiments, the connection element may be a luer slip connection or a luer lock connection.

In one or more embodiments, the plurality of knobs protrudes outwards from the exterior wall surface.

Another aspect of the present disclosure pertains to an assembly of a syringe tip cap and an IV access port disinfecting unit having mechanical mating features that facilitate automated assembly. In one or more embodiments, mechanical locking is achieved by use of undercuts, interference fits, and locking tapers.

In one or more embodiments, anti-rotation is achieved by use of ribs, fins, and channels.

In one or more embodiments, automated or universal alignment is achieved by used of channels and chamfers.

DETAILED DESCRIPTION

Figure 1:
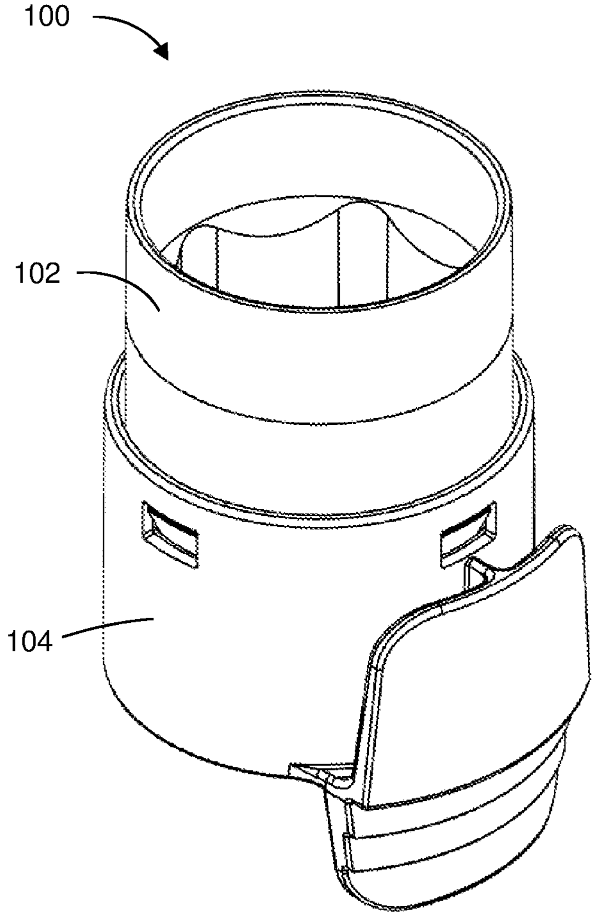
FIG. 1 illustrates a perspective view of an integrated disinfection syringe tip cap assembly in accordance with a first embodiment of the present disclosure.

Before describing several exemplary embodiments of the present disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

Reference to "pre-filled syringe assembly" includes syringes which have barrels filled prior to delivery to the user with a solution or medicament during or after the assembly of the syringe using sterile filling methods. Pre-filled syringe assembly include syringe assemblies are indicated for use in the flushing of vascular access devices (VADs).

As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the VAD. A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Clinicians need to handle multiple components while accessing an intravenous (IV) line or catheter as they are required to open and disinfect the hub, open the syringe, hold the line in place, etc. while ensuring that none of the devices touch any surfaces as this would lead to contamination and blood stream infections which can have deadly outcomes. Therefore, accessing an intravenous (IV) line or catheter is not straightforward and requires a certain level of dexterity to carry out the procedure while preventing the syringe tip from coming into contact with the surrounding environment. If the syringe tip touches any non-sterile surfaces, "touch" contamination can occur which can cause microbial growth in the IV line and consequently lead to incidents of catheter-associated-bloodstream infection ("CRBSI") and central line-associated bloodstream infection ("CLABSI") which are very costly and lethal.

Embodiments of the present disclosure relate to a pre-filled syringe assembly having an integrated disinfection unit assembled to a syringe tip cap by flexible features to a physical barrier for securely sealing the tip of a hypodermic syringe barrel, preventing contact of the syringe tip with the surrounding non-sterile environment and providing for a means of mechanical and chemical disinfection. The disinfection unit provides means of mechanical and chemical disinfection, i.e. a scrubbing unit (foam, etc.) and a chemical disinfectant (alcohol, etc.). Embodiments of the present disclosure provide mechanical means of joining the disinfection unit and the syringe tip cap post sterilization, without the need for adhesive.

Embodiments of the present disclosure allow for permanently joining the disinfection unit to the syringe unit for performing the disinfection and the following flushing process in standard SAS and SASH procedures. Embodiments of the present disclosure engage the disinfection unit and the syringe tip cap on the assembly line, using flexible elements, e.g. clips, on the syringe tip cap or the disinfection unit. In one or more embodiments, the disinfection unit is in the form of a cup. These flexible elements, e.g. clips, tabs, etc., on either the disinfection unit or the syringe tip cap engage to a corresponding mating feature on the other component, lock, and prevent disengagement once the disinfection unit and the syringe tip cap are assembled. The mechanisms to engage the disinfection unit and the syringe tip cap on the assembly line, necessitate minimum alignment and create minimum disturbance each other. This is critical for sustaining sterility post assembly, in case any of the components of the disinfection unit and the syringe tip cap are sterilized.

The flush syringe contains flush solution e.g. saline or other medication through the shelf life of the product and enables delivery of this saline during use, i.e. the syringe is connected to a hub (such as needle-free connectors, etc.) and the syringe contents are delivered.

The syringe cap provides container closure integrity for the syringe contents through the shelf life and is removed by the user prior to flush administration.

The disinfection unit provides means of disinfection of the hub, through mechanical and chemical disinfection. The disinfection unit contains the chemical disinfectant (such as Isopropyl alcohol 70%) through the shelf life of the product.

Figure 2:
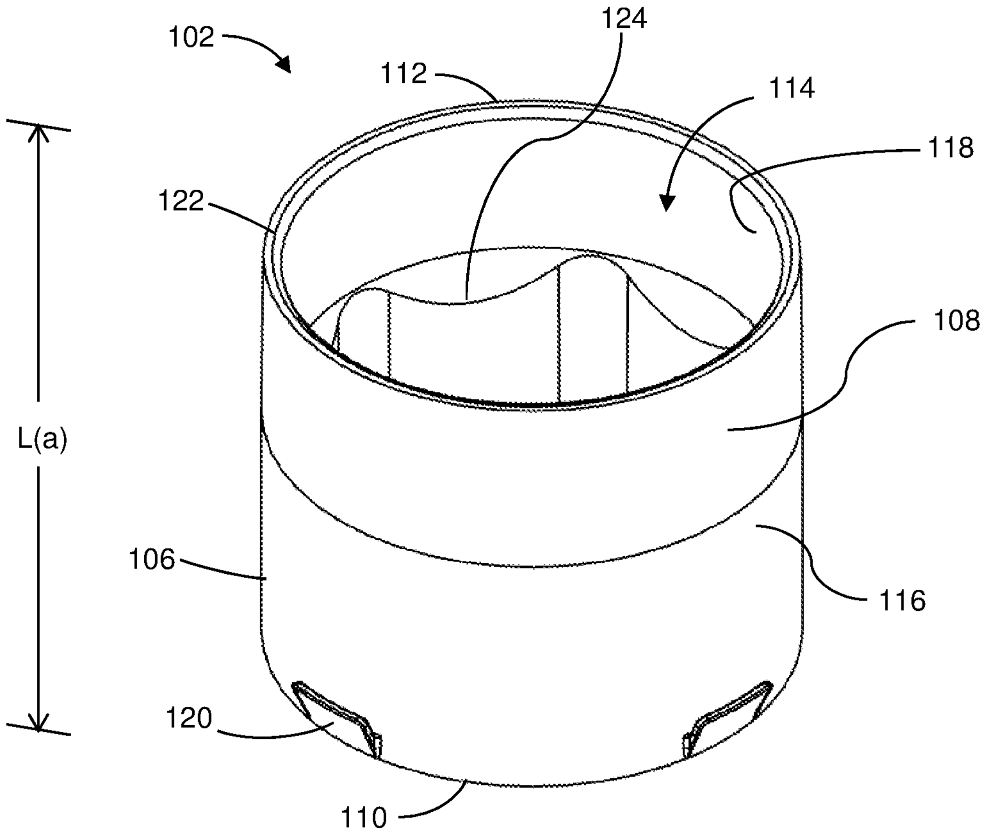
FIG. 2 illustrates a perspective view of a cup in accordance with a first embodiment of the present disclosure.

Referring to FIGS. 1-2, the cup 102 comprises an integral body 106, an annular wall 108 having a length L(a) extending from the closed end 110 to an open end 112 that defines a chamber 114. The annular wall 108 comprises of an exterior wall surface 116 and an interior wall surface 118. The exterior wall surface 116 of the annular wall 108 comprises of a plurality of clips 120. The clips 120 protrude outwards from the exterior wall surface 116 and are adjacent to the closed end 110 of the cup 102.

The chamber 114 of the cup 102 comprises of a plurality of inward protrusions 124 adjacent to the interior wall surface 118. The inward protrusions 124 are shaped as a hex fitting to provide extended connection from the cup.

Figure 3:
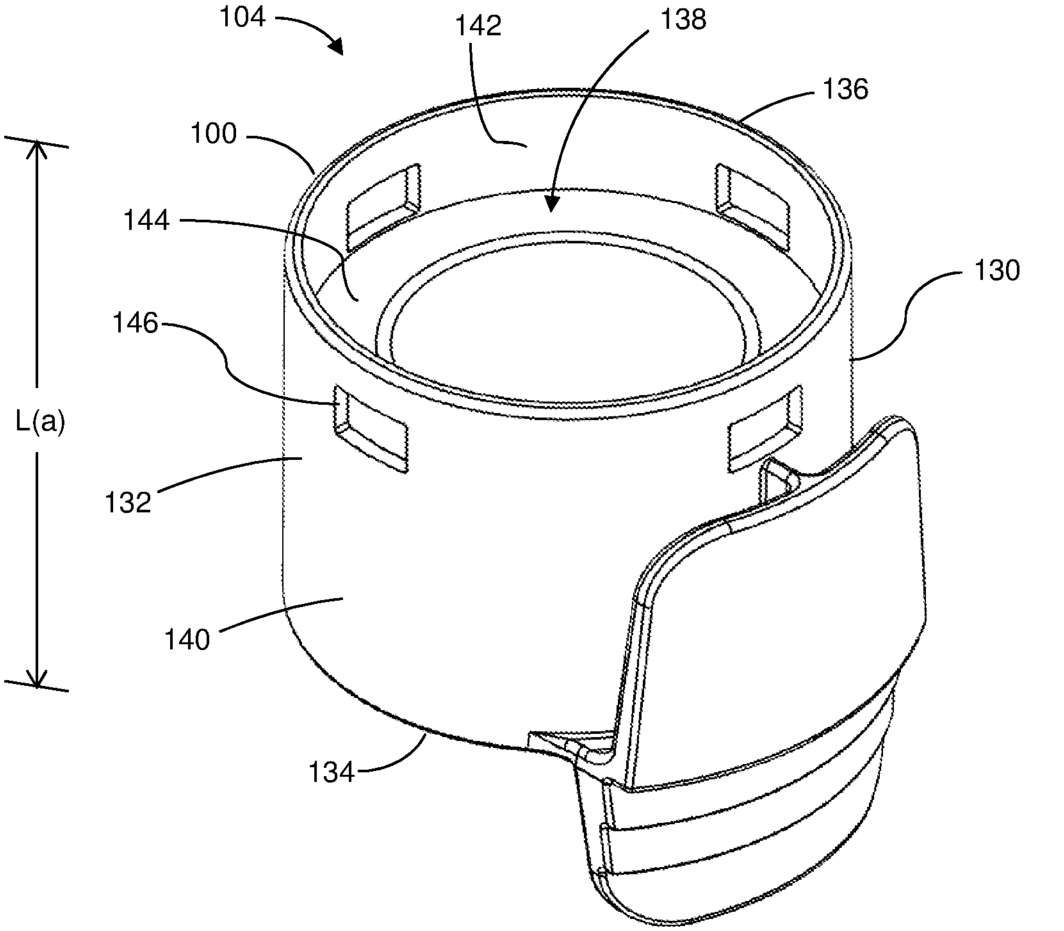
FIG. 3 illustrates a perspective view of a cap in accordance with a first embodiment of the present disclosure.

Referring to FIG. 3, the cap 104 comprises an integral body 130, an annular wall 132 having a length L(a) extending from the bottom end 134 to a top end 136 that defines a chamber 138. The annular wall 132 also comprises of an exterior wall surface 140 and an interior wall surface 142. The chamber 138 of the cap 104 comprises of a mating surface 144. The chamber 138 is appropriately sized to adapt to the annular wall 108 of the cup 102.

Furthermore, the annular wall 132 comprises of a plurality of locking holes 146 that extend from the interior wall surface 142 to the exterior wall surface 140. The bottom surfaces of the locking holes 146 are coincident with the mating surface 144 of the chamber 138.

In general, the clips 120 are configured as a locking mechanism whereby one-way flexing clips 120 which require relatively low axial forces to assemble and produce significant locking strength. As the cap 104 and cup 102 are assembled, the clips 120 flex inward until they enter the locking holes 146 on the cap 104. Once aligned, the clips spring or deflect outward creating a mate between the cap 104 and cup 102. Additionally, the components do not require complete clip and hole alignment during the assembly process as the individual parts self-align during assembly. Once the closed end 110 of the cup 102 bottoms out on the mating surface 144 of the cap 104, the clips 120 are configured to align and lock with the hole 146 by rotating the parts by a quarter turn.

Specifically, during assembly of the cup 102 and the cap 104, the closed end 110 of the cup 102 is inserted into the chamber 138 of the cap 104. The clips 120 flex inward towards the annular wall 108 of the cup 102. Once the clips 120 are aligned with the locking holes 146 of the cap 104, the clips 120 spring outward—creating a permanent mate between the two parts without the use of adhesives. Exact alignment of the clips 120 and the locking holes 146 are not necessary to complete the assembly process. Once the cup 102 has been inserted into the chamber 138 of the cap 104 and the mating surface 144 makes contact with the closed end 110, rotation of the cup 102 relative to the cap 104 will ensure alignment of the clips 120 and the locking holes 146, or vice versa. Once the assembly is complete, the mechanical mating prevents the cup 102 from being removed from the cap 104 by pulling the components away from each other. Additionally, this mechanical mating prevents any rotation of the two components relative to each other.

Figure 4:
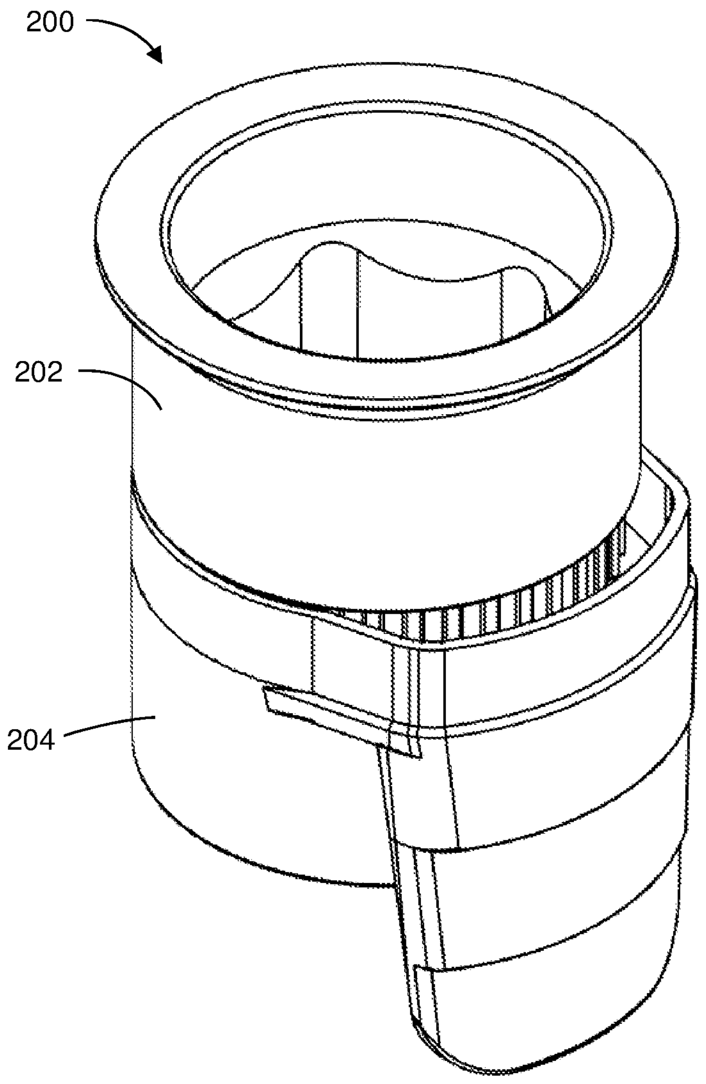
FIG. 4 illustrates a perspective view of an integrated disinfection syringe tip cap assembly in accordance with a second embodiment of the present disclosure.
Figure 5:
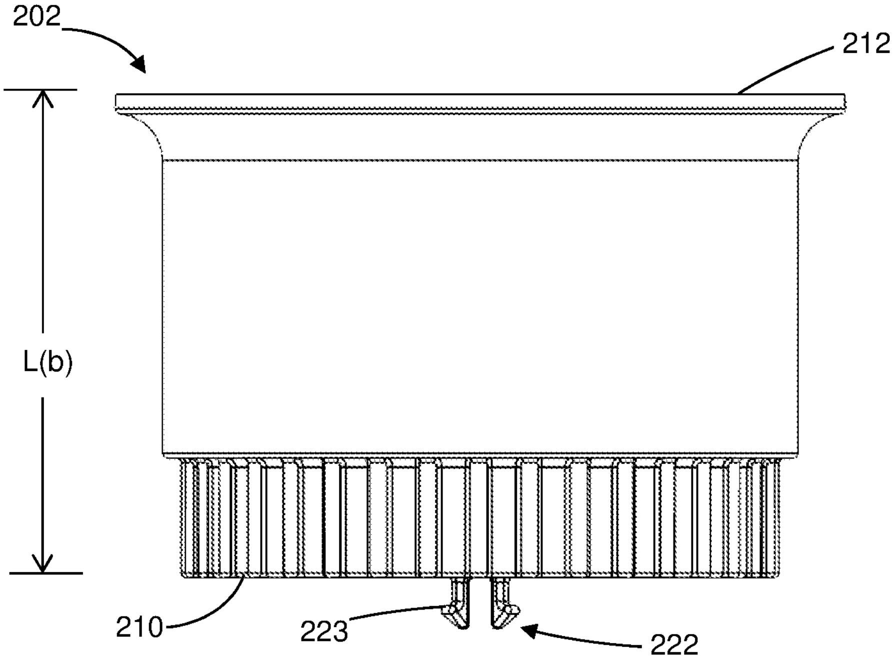
FIG. 5 illustrates a side view of a cup in accordance with a second embodiment of the present disclosure.
Figure 6:
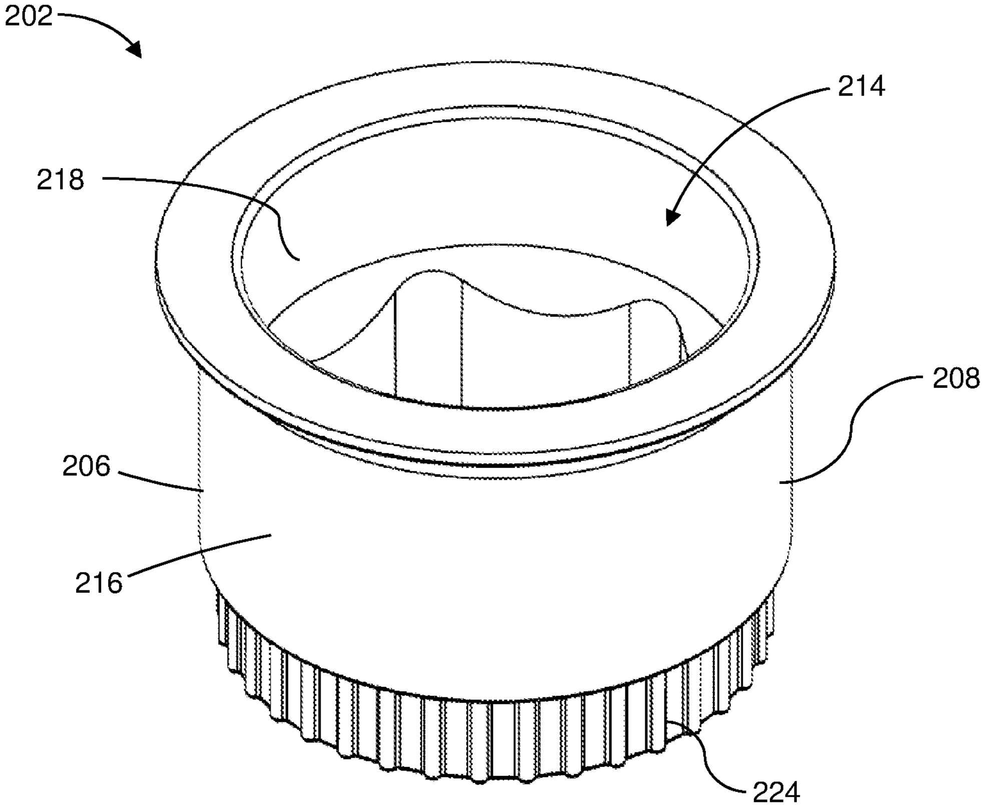
FIG. 6 illustrates a perspective view of a cup in accordance with a second embodiment of the present disclosure.

Referring to FIGS. 4-6, the cup 202 comprises an integral body 206, an annular wall 208 having a length L(b) extending from the closed end 210 to an open end 212 that defines a chamber 214. The annular wall 208 comprises of an exterior wall surface 216 and an interior wall surface 218.

The annular wall 208 also comprises of a plurality of alignment teeth 224 adjacent to the closed end 210 of the cup 202. The chamber 214 of the cup 202 comprises of a plurality of inward protrusions 124 adjacent to the interior wall surface 218. The inward protrusions 124 are shaped as a hex fitting to provide extended connection from the cup.

The cup 202 also comprises a plurality of locking tabs 222 that extend away from the closed end 210. The locking tabs 222 are perpendicular to the closed end 210 of the cup 202. Each locking tab 222 comprises of a lip 223 that makes the shape similar to a harpoon. The locking tabs 222 are situated in the center of the surface on which the closed end 210 exists. The lip 223 of the locking tabs 222 faces in the opposite direction of each other. The amount of locking tabs 222 may vary.

Figure 7:
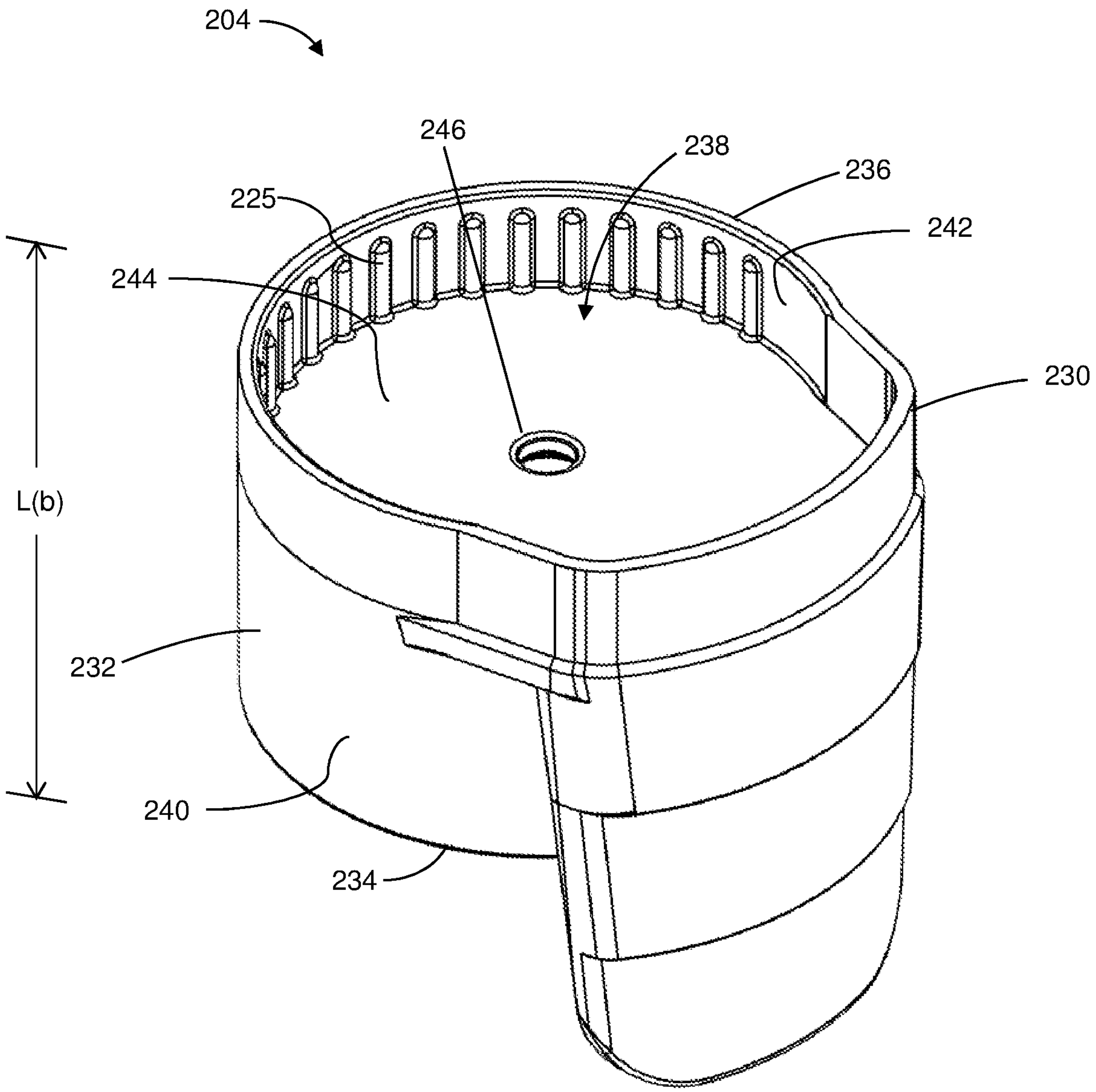
FIG. 7 illustrates a perspective view of a cap in accordance with a second embodiment of the present disclosure.

Referring to FIG. 7, the cap 204 comprises an integral body 230, an annular wall 232 having a length L(b) extending from the bottom end 234 to an top end 236 that defines a chamber 238. The annular wall 232 comprises of an exterior wall surface 240 and an interior wall surface 242. The chamber 238 is appropriately sized to adapt to the annular wall 208 of the cup 202. The interior wall surface 242 comprises of a plurality of alignment teeth 225. The alignment teeth 225 are spaced evenly along the interior wall surface 242 of the annular wall 232; however, the alignment teeth 225 may take up only a partial surface of the interior wall surface 242. The chamber 238 of the cap 204 comprises of a mating surface 244. In the center of the mating surface 244 exists a locking hole 246.

In general, as the cap 204 and the cup 202 are assembled, the harpoon-shaped locking tab 222 flex inward until they enter the locking hole 246 on the top of the cap 204. Once the harpoon-shaped locking tab 222 clear the undercut on the locking hole 246, the harpoon-shaped locking tab 222 spring outward creating a lock between the cap 204 and the cup 202.

Specifically, during assembly of the cup 202 and the cap 204, the closed end 210 of the cup 202 is inserted onto the chamber 238 of the cap 204 to make contact with the mating surface 244 of the cap 204. As it enters the locking hole 246 of the cap 204, the locking tabs 222 of the cup 202 flex inward. Once the lips 223 of the locking tabs 222 clear the undercut of the locking hole 246, they spring outward creating a lock between the cap 204 and the cup 202. The alignment teeth 224 of the cup 202 and the cap 204 guide the two components during the assembly process to ensure smooth and accurate assembly for high speed manufacturing. The alignment teeth 224 also prevent any rotation of the two components relative to each other. Additionally, the components can be assembled universally and do not require specific orientation.

Figure 8:
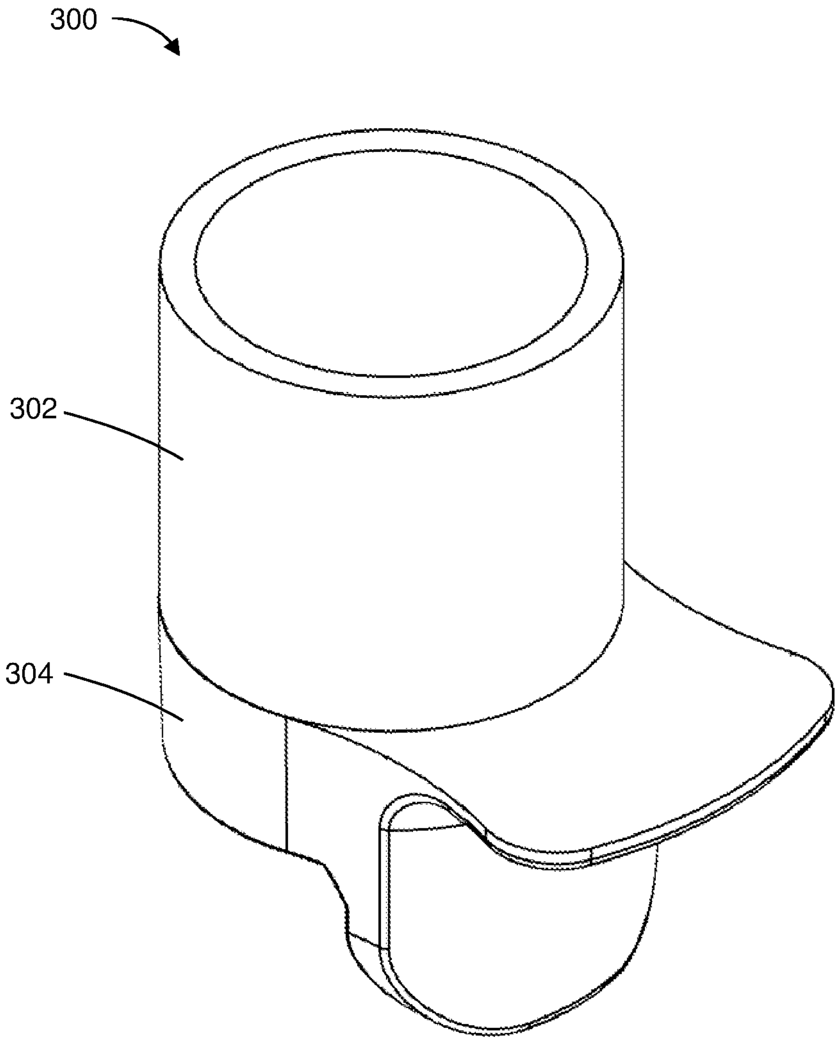
FIG. 8 illustrates a perspective view of an integrated disinfection syringe tip cap assembly in accordance with a third embodiment of the present disclosure.
Figure 9:
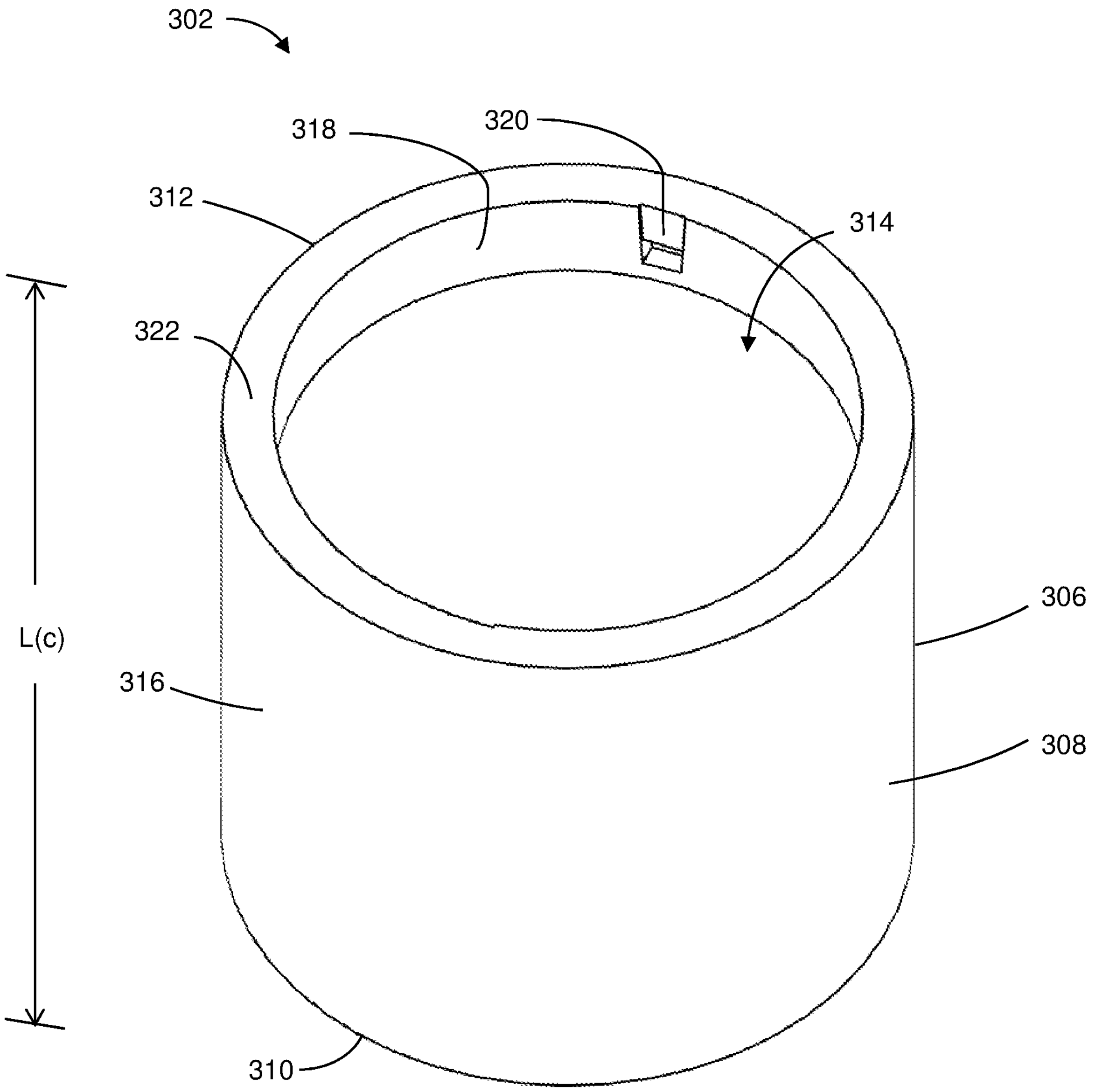
FIG. 9 illustrates a perspective view of a cup in accordance with a third embodiment of the present disclosure.

Referring to FIGS. 8-9, the cup 302 comprises an integral body 306, an annular wall 308 having a length L(c) extending from the top end 310 to a bottom end 312 that defines a chamber 314. The annular wall 308 comprises of an exterior wall surface 316 and an interior wall surface 318, as well as a peripheral surface 322. The interior wall surface 318 of the annular wall 308 comprises of a plurality of opposite facing female receivers 320 of the interior wall surface 318.

Figure 10:
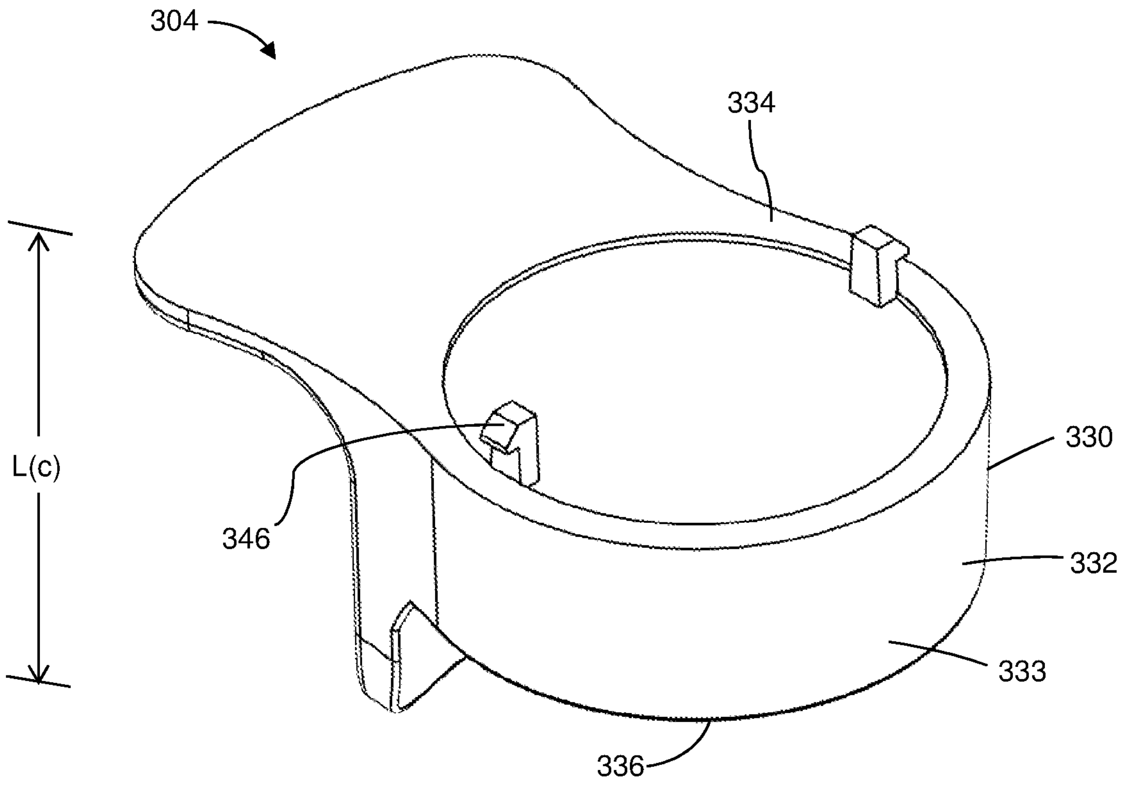
FIG. 10 illustrates a perspective view of a cap in accordance with a third embodiment of the present disclosure.

Referring to FIG. 10, the cap 304 comprises an integral body 330, an annular wall 332 having a length L(c) extending from a closed end 334 and an open end 336. The annular wall 332 comprises of a smooth wall 333. Perpendicular to the closed end 334 of the cap 304 exist a plurality of flexing tabs 346. In one or more embodiments, the flexing tabs 346 are harpooned shaped.

As the cap 304 and the cup 302 are assembled, the flexing tabs 346 flex inward into the chamber 314 of the cup 302. Once the flexing tabs 346 of the cap 304 clear the peripheral surface 322 of the cup 302, the flexing tabs 346 snap outward to secure into the female receivers 320 of the cup 302. Once mated, the peripheral surface 322 is in contact with the closed end 334 of the cup 302. This embodiment improves the aesthetic features of the first embodiment due to that the mating features are hidden under the components once mated. Once the assembly is complete, the mechanical mating prevents the cup 102 from being removed from the cap 104 by pulling the components away from each other. Additionally, this mechanical mating prevents any rotation of the two components relative to each other.

Figure 11:
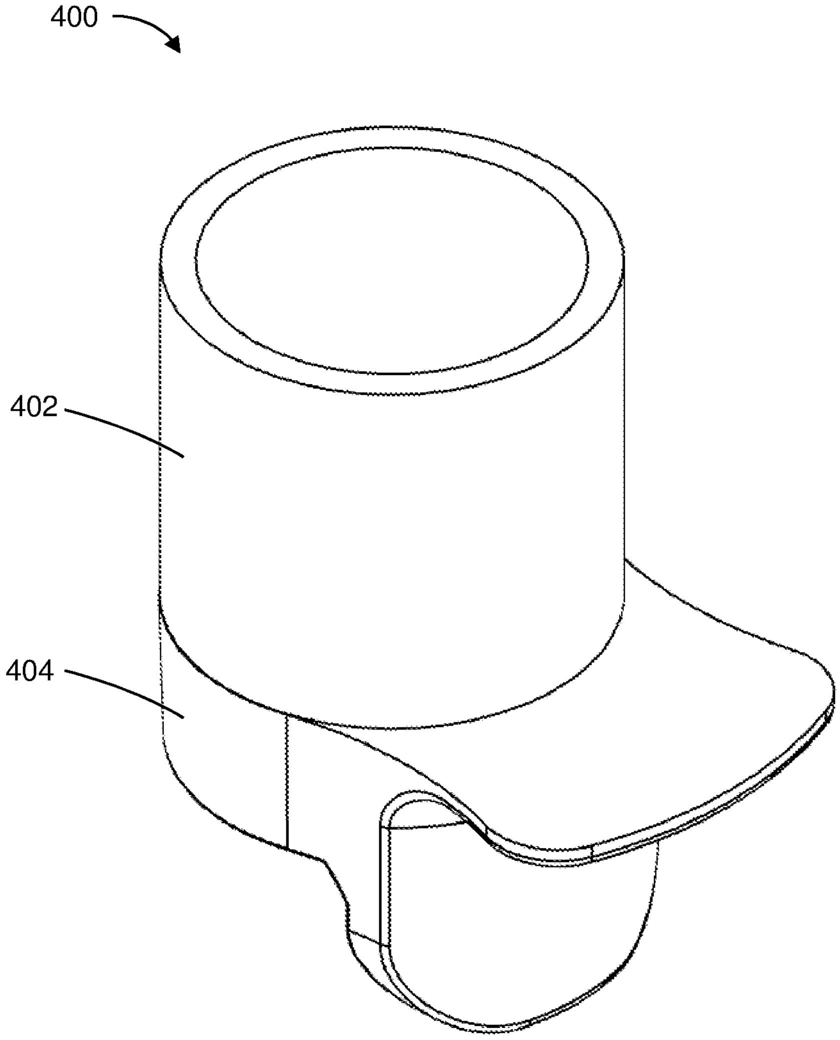
FIG. 11 illustrates a perspective view of an integrated disinfection syringe tip cap assembly in accordance with a fourth embodiment of the present disclosure.
Figure 12:
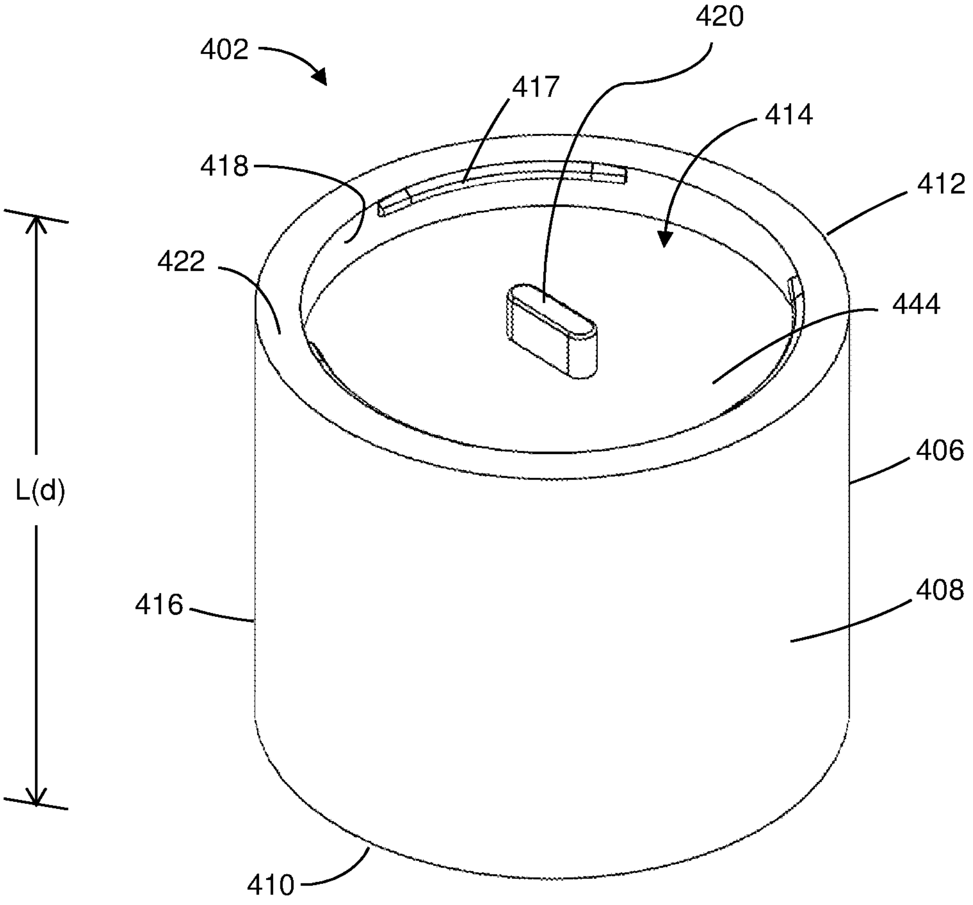
FIG. 12 illustrates a bottom perspective view of a cup in accordance with a fourth embodiment of the present disclosure.

Referring to FIGS. 11-12, the cup 402 comprises an integral body 406, an annular wall 408 having a length L(d) extending from the top end 410 to a bottom end 412 that defines a chamber 414. The annular wall 408 comprises of an exterior wall surface 416 and an interior wall surface 418, as well as a peripheral rim 422. The interior wall surface 418 comprises of a plurality of protrusions 417 that are adjacent to the peripheral rim 422. The length of the protrusions 417 runs parallel to the peripheral rim 422; however, their length may vary. The protrusions 417 are uniformly spaced along the circumference of the interior wall surface 418. In one or more embodiments, the spacing between the protrusions 417 will change depending on the number protrusions included in the embodiment.

The chamber 414 comprises of a mating surface 444. In the center of the mating surface 444 a male slot 420 protrudes out perpendicularly from the mating surface 444 in the direction away from the mating surface 444.

Figure 13:
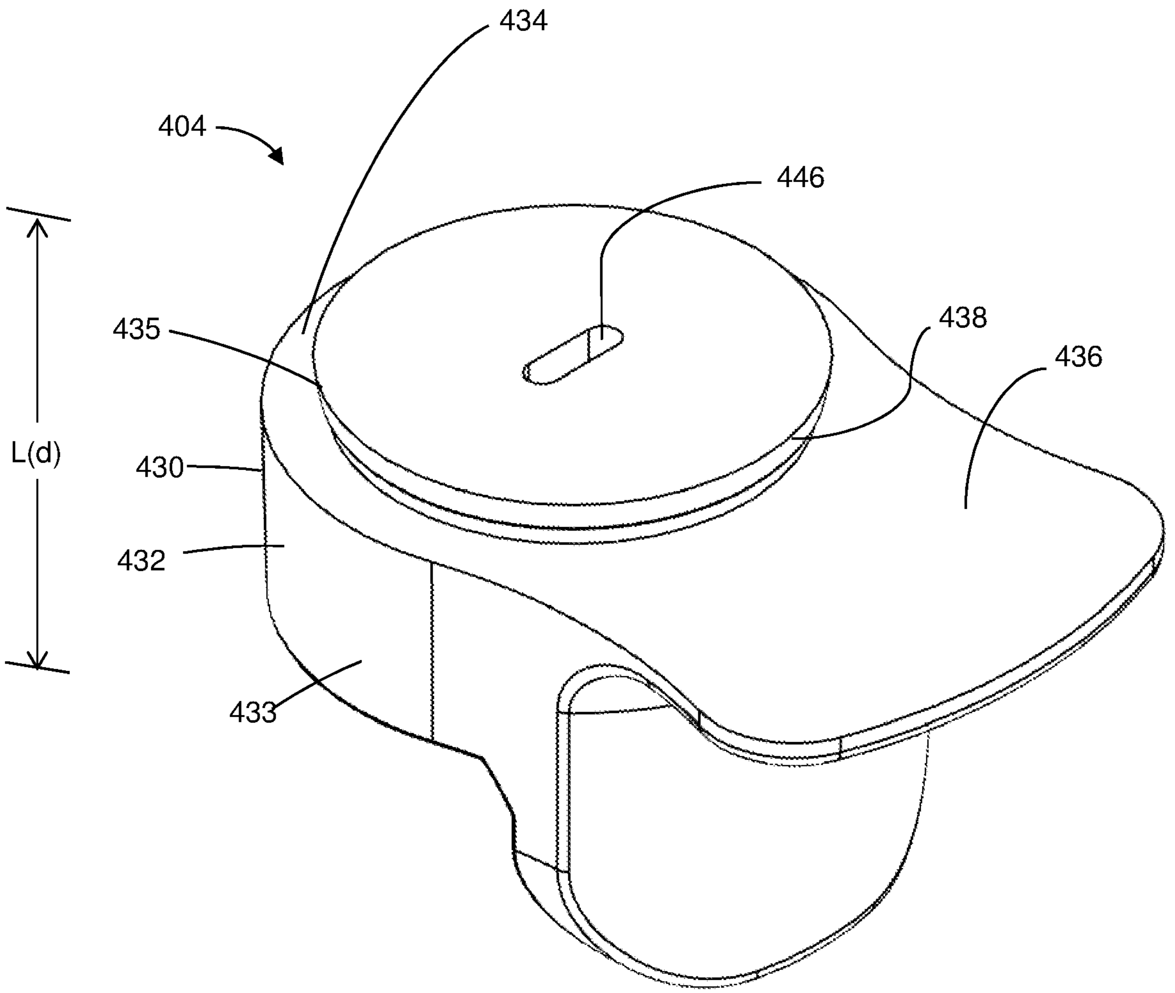
FIG. 13 illustrates a perspective view of a cap in accordance with a fourth embodiment of the present disclosure.
Figure 14:
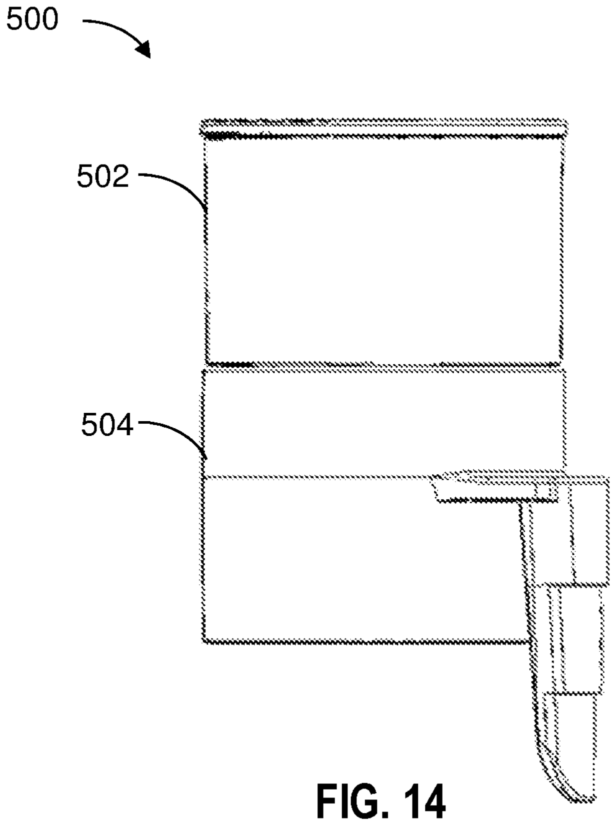
FIG. 14 illustrates a perspective view of a an integrated disinfection syringe tip cap assembly in accordance with a fifth embodiment of the present disclosure.

Referring to FIG. 13, the cap 404 comprises an integral body 430, an annular wall 432 having a length L(d) extending from the closed end 434 to an top end 436. The annular wall 432 comprises of a smooth wall 433. Normal to the plane of the closed end 434 of the cap 404 exists a mating protrusion 435. Surrounding the mating protrusion 435 is a peripheral rim 438 that increases the diameter of the mating protrusion 435. Located in the center of the mating protrusion 435 exists a female slot 446.

As the cap 404 and the cup 402 are assembled, bottom end 412 of the cup 402 is oriented to face the top end 436 of the cap 404. The chamber 414 of the cup 402 is inserted over the mating protrusion 435 of the cap 404. As the user presses the cup 402 onto the cap 404, the peripheral rim 438 causes the protrusions 417 of the cup 402 to radiate outwards. Once the protrusions 417 of the cup 402 clear the peripheral rim 438 of the cap 404, the protrusions snap back inward and lock the cup 402 onto the cap 404. Simultaneously, the male slot 420 on the cup 402 fits into the female slot 446 of the cap 404. Once the assembly is complete, the male slot 420 and female slot 446 lock the components such that the rotation of the cup 402 with respect to the cap 404 is prohibited during use. This embodiment requires the user to insert the cup 402 onto the cap 404 in a specific orientation. If the components are not in the correct orientation during assembly, the components cannot be mated together.

Referring to FIGS. 14-17, the cup 502 comprises an integral body 506, an annular wall 508 having a length L(e) extending from the top end 510 to a bottom end 512. The annular wall 508 comprises of an exterior wall surface 516 and an interior wall surface 518. The annular wall 508 also comprises of a plurality of alignment teeth 524 adjacent to the bottom end 512 of the cup 502. The exterior wall surface 516 also comprises an annular snap joint (female feature) 550.

Figure 17:
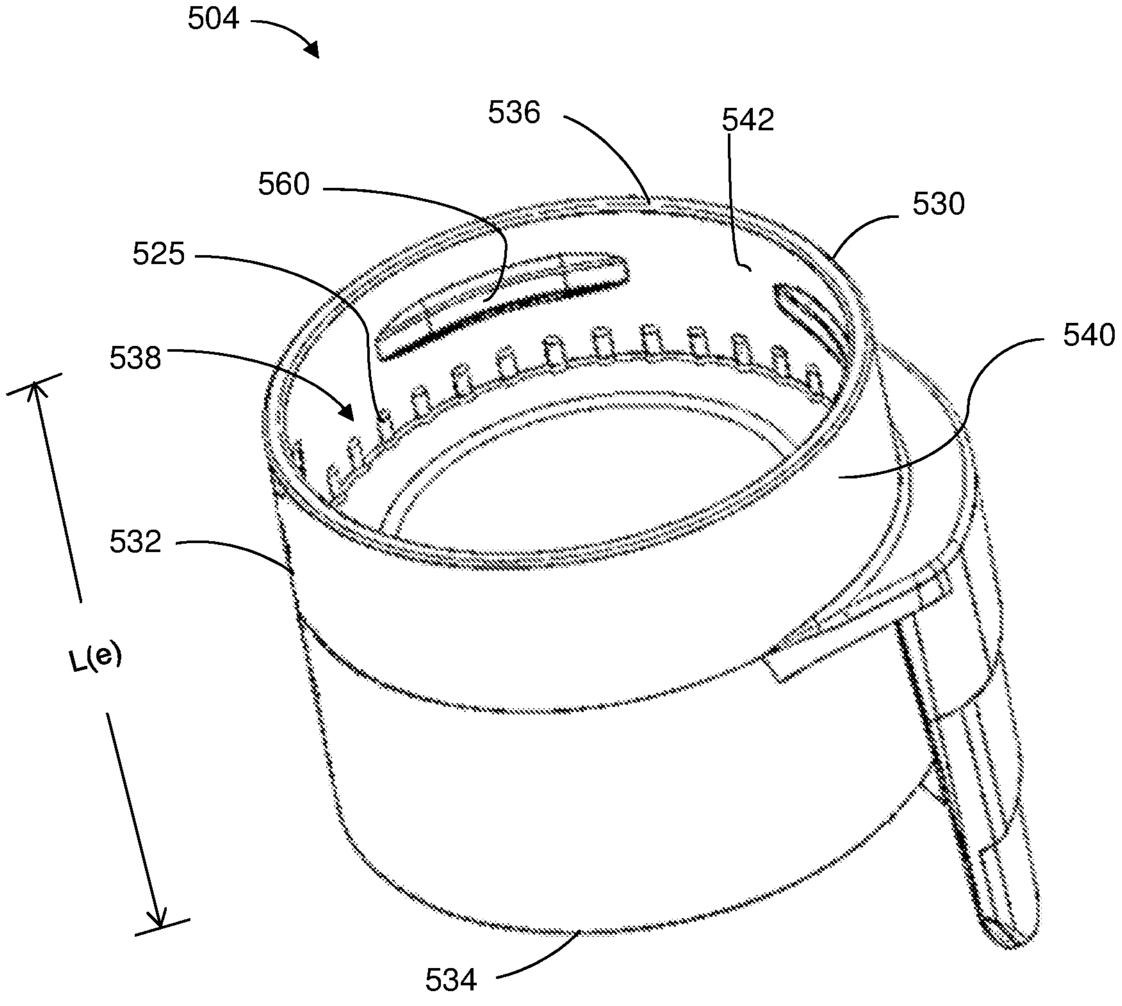
FIG. 17 illustrates a perspective view of a cap in accordance with a fifth embodiment of the present disclosure.

Referring to FIG. 17, The cap 504 comprises an integral body 530, an annular wall 532 having a length L(e) extending from the bottom end 534 to an top end 536 that defines a chamber 538. The annular wall 532 comprises of an exterior wall surface 540 and an interior wall surface 542. The chamber 538 is appropriately sized to adapt to the annular wall 508 of the cup 502. The interior wall surface 542 comprises of a plurality of alignment teeth 525 and an annular snap joint 560. In one or more embodiments, the annular snap joint 560 includes a male feature in the form of locking tabs. The alignment teeth 525 are spaced evenly along the interior wall surface 542 of the annular wall 532; however, the alignment teeth 525 may take up only a partial surface of the interior wall surface 542.

Figure 15:
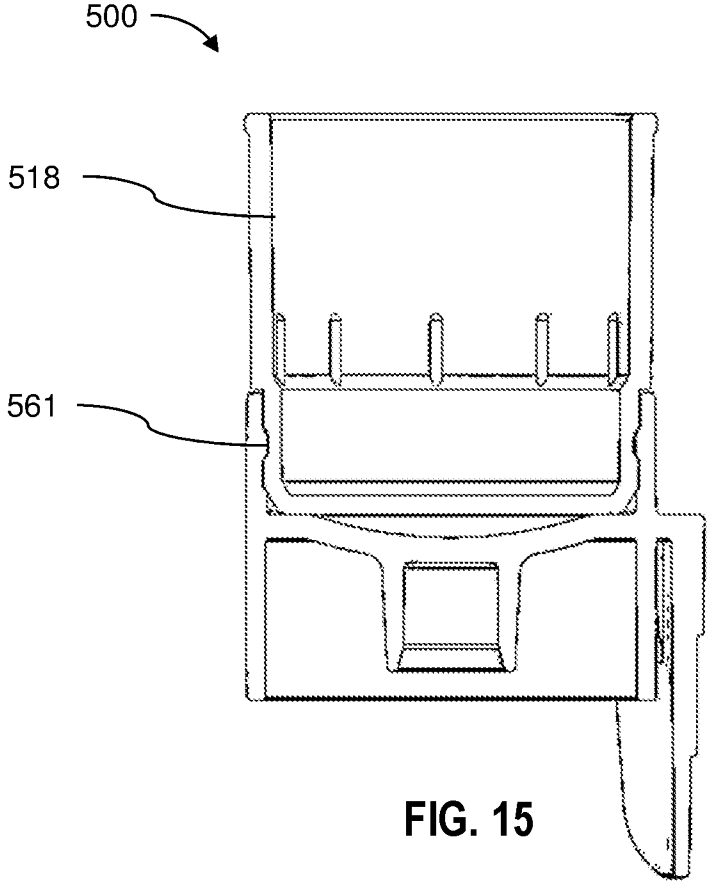
FIG. 15 illustrates a cross-section view of a an integrated disinfection syringe tip cap assembly in accordance with a fifth embodiment of the present disclosure.
Figure 16:
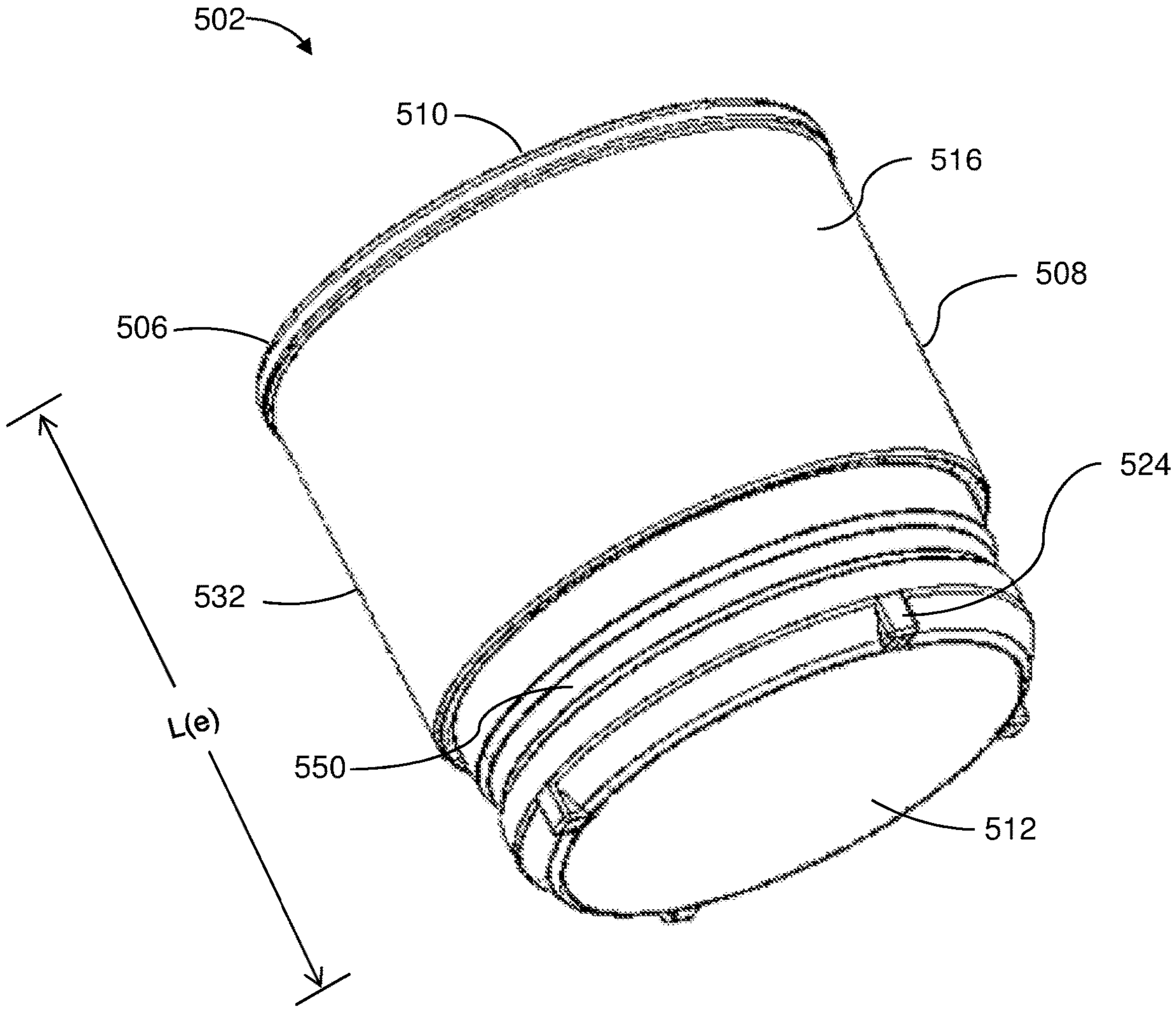
FIG. 16 illustrates a perspective view of a cup in accordance with a fifth embodiment of the present disclosure.

As the cap 504 and the cup 502 are assembled, bottom end 512 of the cup 502 is oriented to face the top end 536 of the cap 504. As the user presses the cup 502 onto the chamber 538 of the cap 504, the annular snap joint (male feature) 560 engages with the annular snap joint (female feature) 550. Thus, an annular snap joint 561 exists between the cup 502 and the cap 504 as shown in FIG. 15. The alignment teeth 524 of the cup 502 fit in between the alignment teeth 225 of the cap 504. During assembly, the cup 502 must be oriented so that the alignment teeth 524 are inserted into the space between the annular snap joint 560.

The alignment teeth of the cup 502 and the cap 504 guide the two components during the assembly process to ensure smooth and accurate assembly for high speed and high volume manufacturing.

Once the assembly is complete, the annular snap joint (female feature) 550 of the cup 502 engage with the annular snap joint 560 and lock the components such that the rotation of the cup 502 with respect to the cap 504 is prohibited during use.

In one or more embodiments, a female opening on the cap 504 for the male portion on the cup 502 locks the parts together with an undercut in the disinfecting unit and four uniform locking tabs on the cap 504. Additionally, there are four fins on the bottom of the cup 502 which will mate in between the ribs on the cap 504 and keep the cup 502 from rotating.

Figure 18:
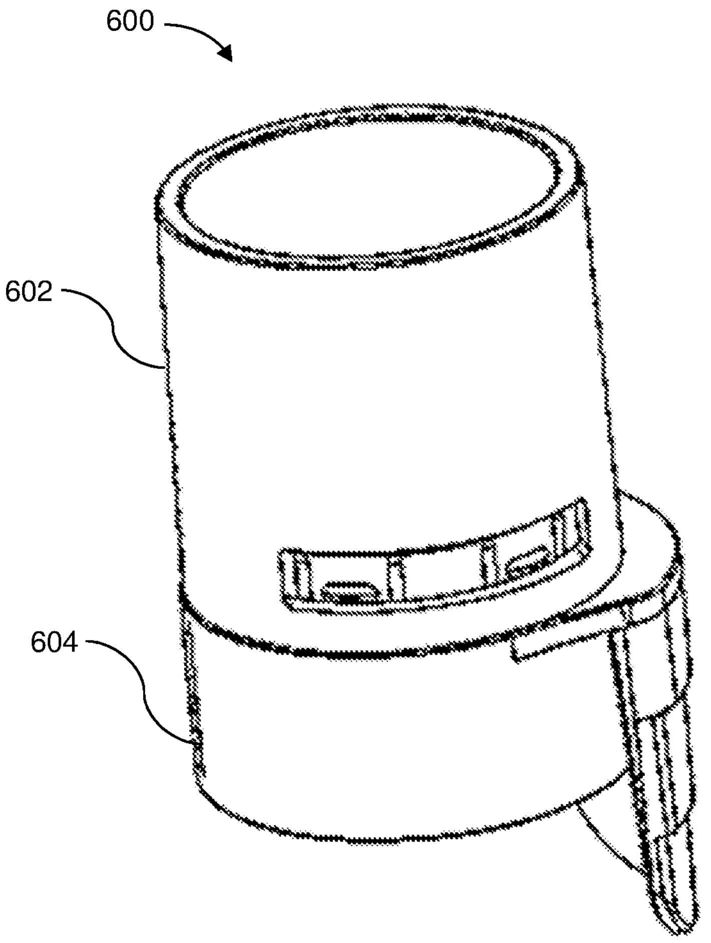
FIG. 18 illustrates a perspective view of an integrated disinfection syringe tip cap assembly in accordance with a sixth embodiment of the present disclosure.
Figure 19:
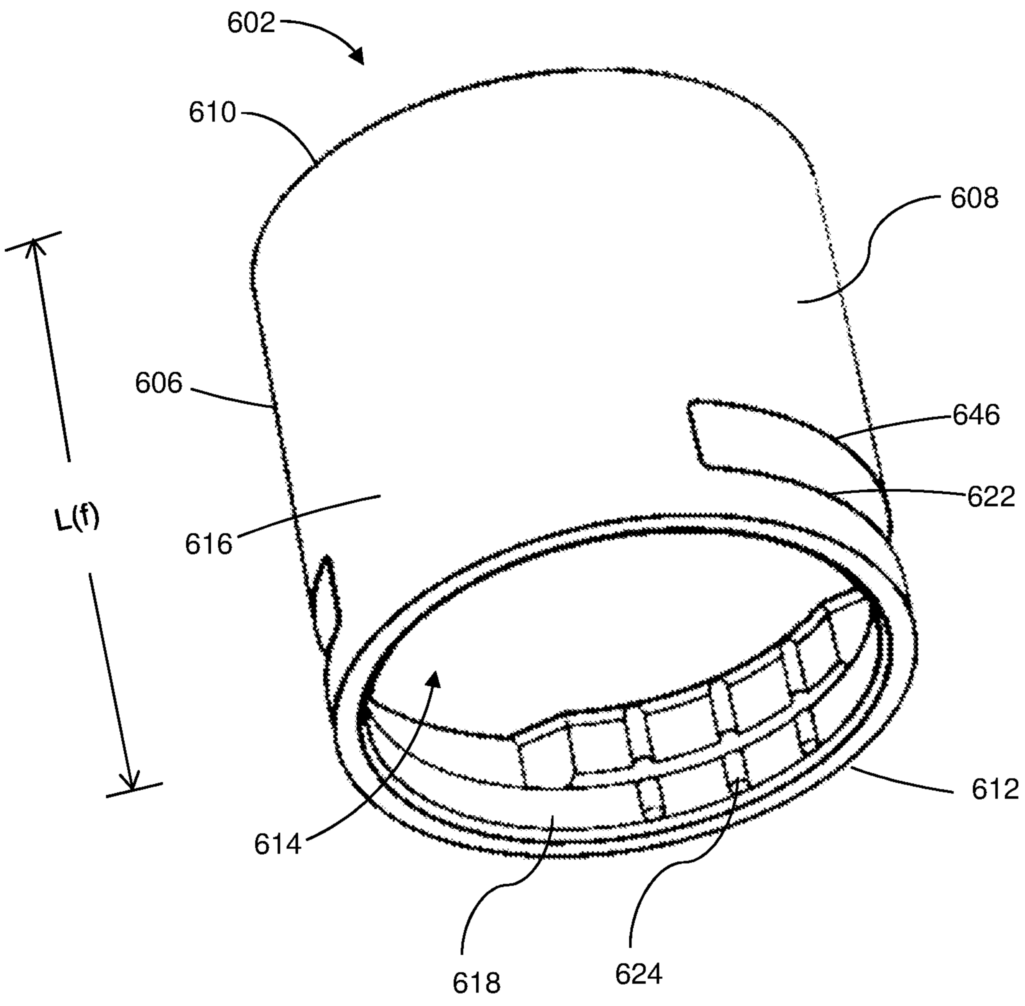
FIG. 19 illustrates a perspective view of a cup in accordance with a sixth embodiment of the present disclosure.

Referring to FIGS. 18-19, the cup 602 comprises an integral body 606, an annular wall 608 having a length L(f) extending from the closed end 610 to an open end 612 that defines a chamber 614. The annular wall 608 comprises of an exterior wall surface 616 and an interior wall surface 618.

Furthermore, the annular wall 608 comprises of a plurality of locking holes 646 that extend radially from the interior wall surface 618 to the exterior wall surface 616. The locking holes 646 are adjacent to the open end 612. The interior wall surface 618 of annular wall 608 also comprises of a plurality of alignment teeth 624 adjacent to the closed end 610 of the cup 602.

Figure 20:
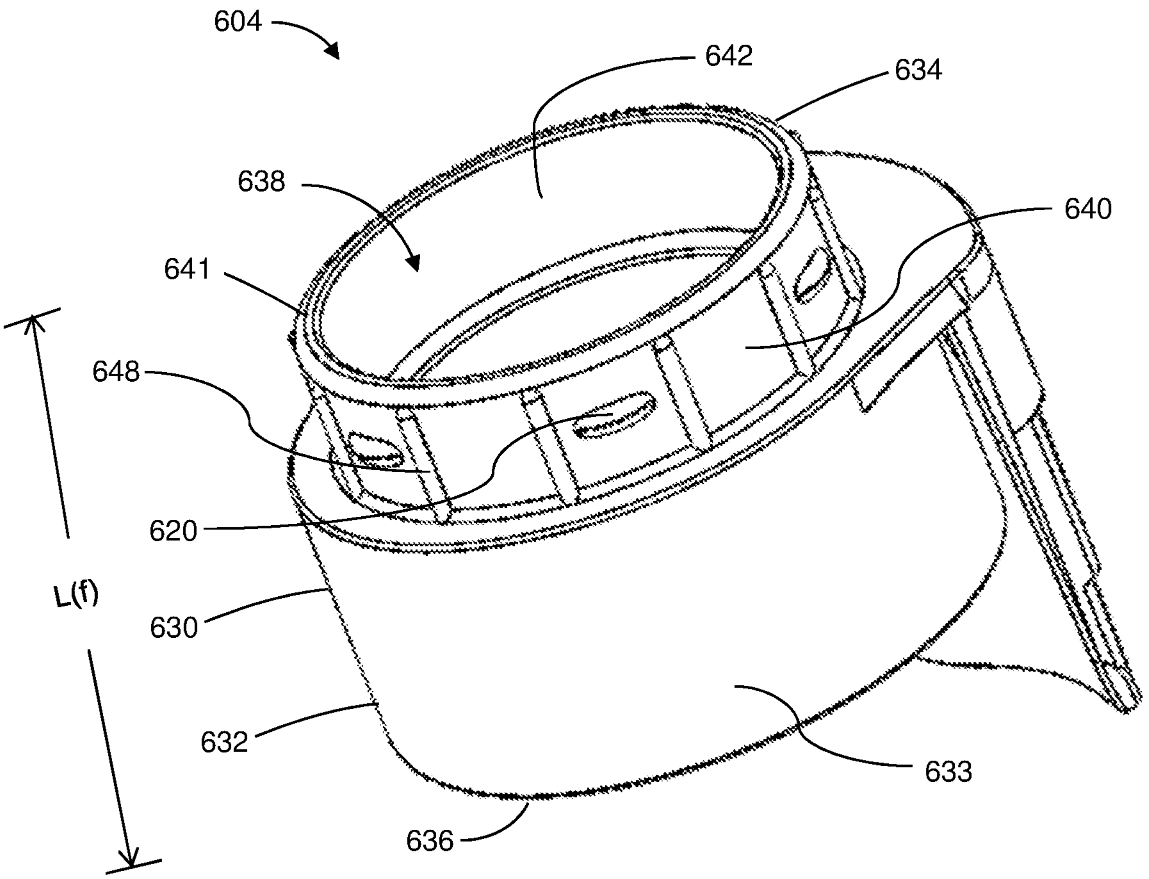
FIG. 20 illustrates a perspective view of a cap in accordance with a sixth embodiment of the present disclosure.
Figure 21:
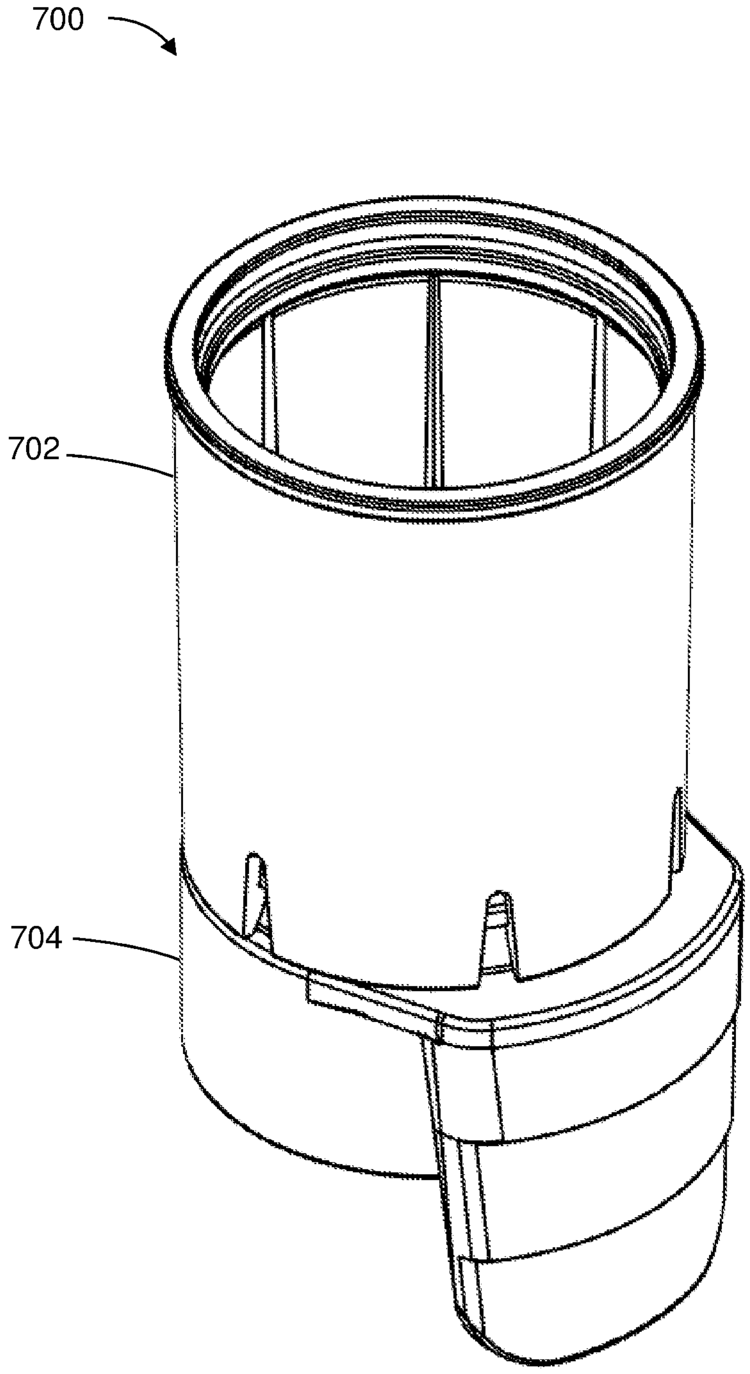
FIG. 21 illustrates a perspective view of an integrated disinfection syringe tip cap assembly in accordance with a seventh embodiment of the present disclosure.
Figure 22:
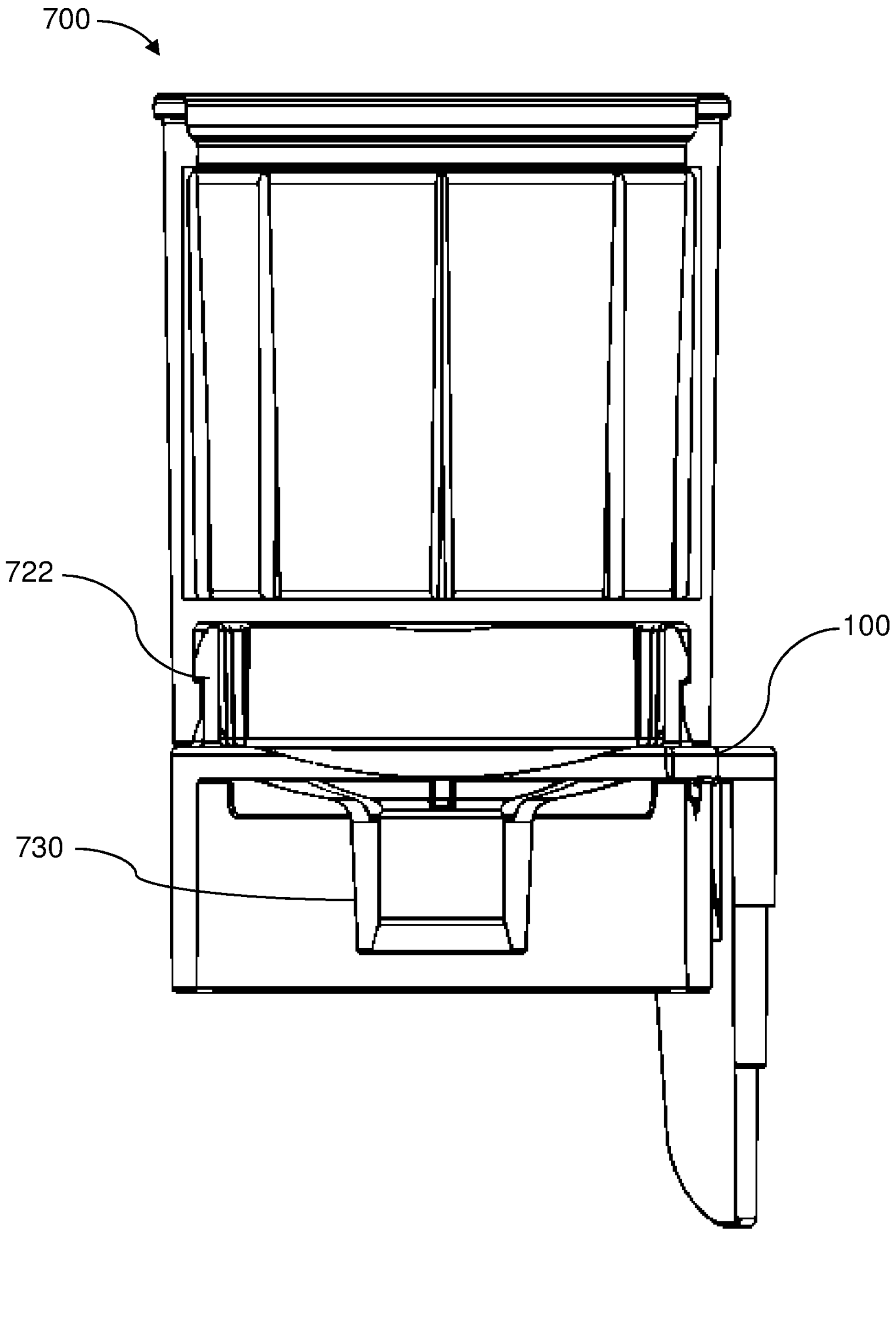
FIG. 22 illustrates a cross-sectional view of a an integrated disinfection syringe tip cap assembly in accordance with a seventh embodiment of the present disclosure.
Figure 23:
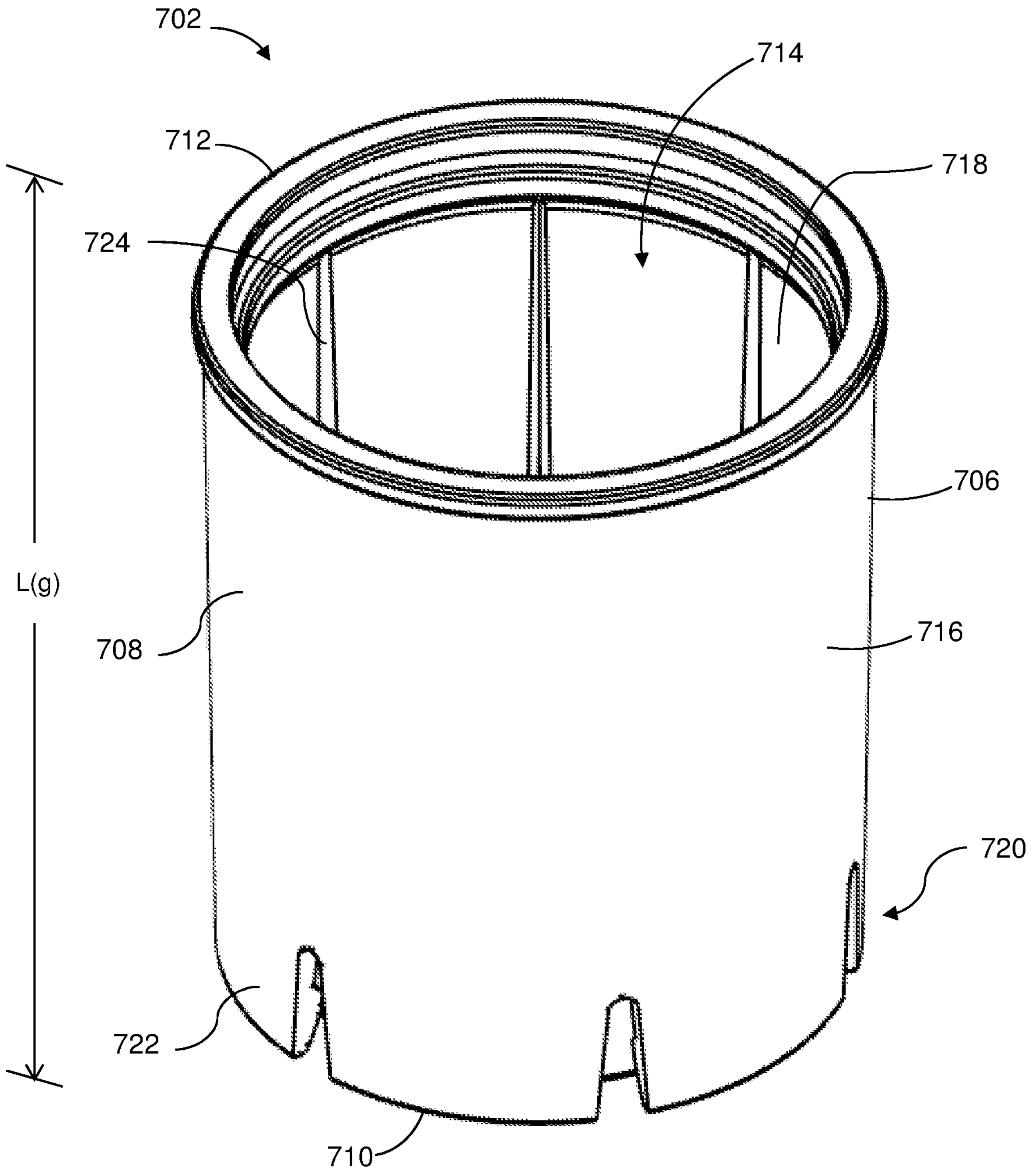
FIG. 23 illustrates a perspective view of a cup in accordance with a seventh embodiment of the present disclosure.
Figure 24:
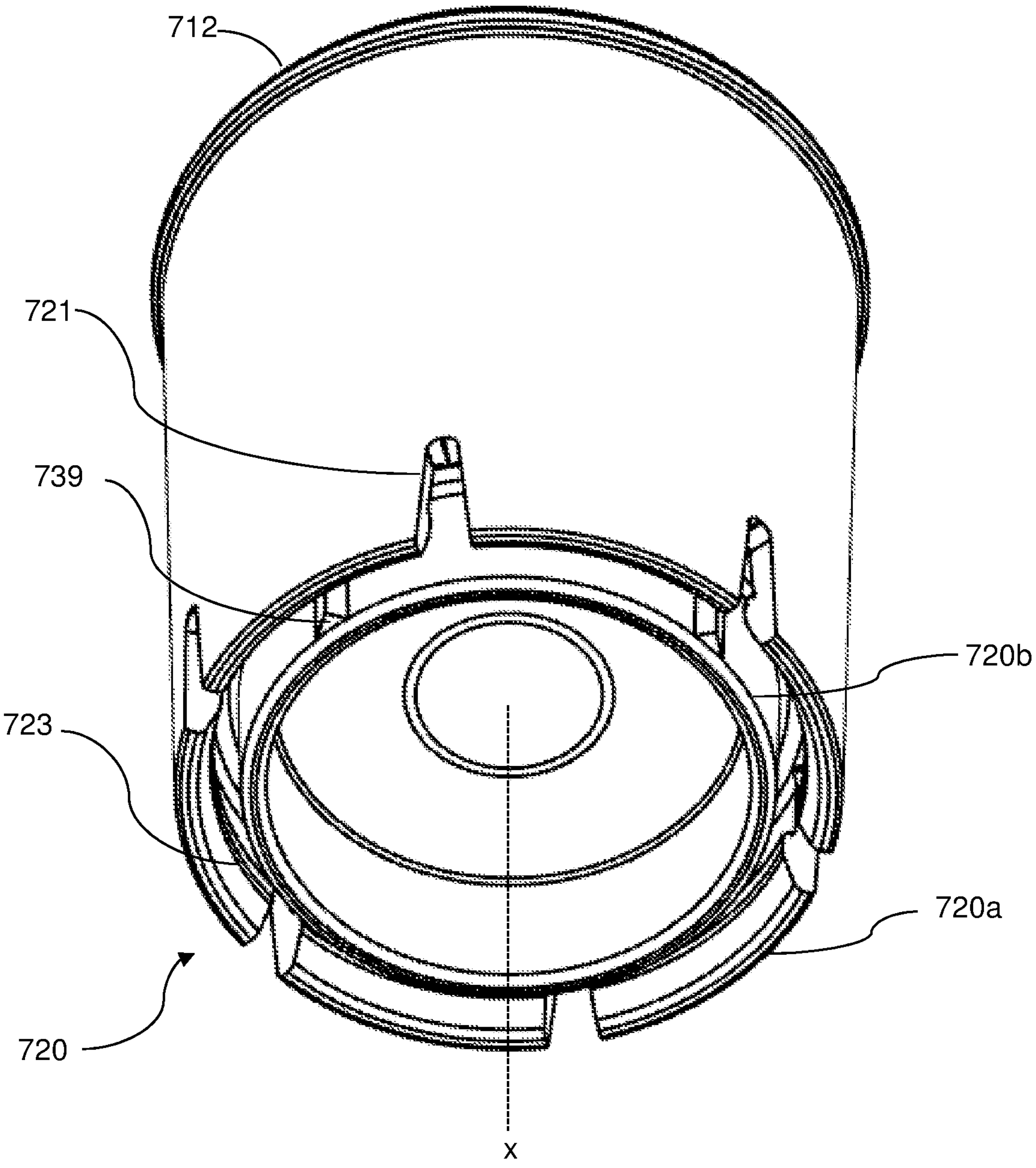
FIG. 24 illustrates a bottom view of a cup in accordance with a seventh embodiment of the present disclosure.

Referring to FIG. 20, the cap 604 comprises an integral body 630, an annular wall 632 having a length L(f) extending from the bottom end 636 to an top end 634 that defines a chamber 638. The annular wall 632 comprises of an exterior wall surface 640 and an interior wall surface 642. The exterior wall surface 640 comprises of a plurality of alignment teeth 648.

The exterior wall surface 640 of the annular wall 608 also comprises of a plurality of knobs 620. The knobs 620 protrude outwards from the exterior wall surface 640.

For assembly of both components, as the user presses the cup 602 onto the cap 604, the alignment teeth 624 of the cup 602 and the alignment teeth 625 of cap 604 guide the two components to allow assembly of the cup 602 and the cap 604. The open end 612 of the cup 602 is inserted onto the top end 634 of the cap 604. Thus, the top portion of the exterior wall surface 640 fits into the chamber 614 of the cup 602. During assembly, the interior wall surface 618 flex outwards over the plurality of knobs 620 on the cap 604. Simultaneously, the knobs 620 of the cup 602 neatly fit in between the alignment teeth 624 of the cup 602. Once the knobs 620 clear the locking hole bottom surface 622, the interior wall surface 618 snaps inward and cause the two components to mate. The complete assembly of the components comprises of the knobs 620 being snap-fitted into the locking holes 646; and the knobs 620 neatly fitted in between alignment teeth 624, providing a friction-fit connection.

Once the knobs 620 are aligned with the locking holes 646 of the cup 602, the knobs 620 spring outward—creating a permanent mate between the two parts without the use of adhesives. Exact alignment of the knobs 620 and the locking holes 646 are not necessary to complete the assembly process. Once the cup 602 has been inserted into the chamber 638 of the cap 604 and the mating surface 644 makes contact with the closed end 610, rotation of the cup 602 relative to the cap 604 will ensure alignment of the knobs 620 and the locking holes 646, or vice versa.

Referring to FIGS. 21-24, the cup 702 comprises an integral body 706, an annular wall 708 having a length L(g) extending from the closed end 710 to an open end 712 that defines a chamber 714. The annular wall 708 comprises of an exterior wall surface 716 and an interior wall surface 718.

The chamber 714 of the cup 702 comprises of a plurality of inward protrusions 724 adjacent to the interior wall surface 718.

The cup 702 also comprises a skirt 720 that extend away from the open end 712 of the cup 702. The skirt comprises of an outer skirt 720*a* and an inner skirt 720*b*. The outer skirt 720*a* comprises of a plurality of parabolic spaces 721 that promote flexibility to the outer skirt 720*a*. The outer skirt 720*a* also comprises of a lip 723 that is situated on the side wall of the outer skirt 720*a*, facing towards the x-axis of the cup 702. In one or more embodiments, the inner skirt 720*b* of the cup 702 comprises of a plurality of alignment teeth 739 that are uniformly spaced about the circumference of the inner skirt 720*b*. The plurality of alignment teeth 739 are situated on the side wall of the inner skirt 720*b*, facing away from the x-axis The outer skirt 720*a* is coincident to the annular wall 708 of the cup 702. The inner skirt 720*b* is concentric to the outer skirt 720*a*; however, its radial distance from the x-axis may vary.

Figure 25:
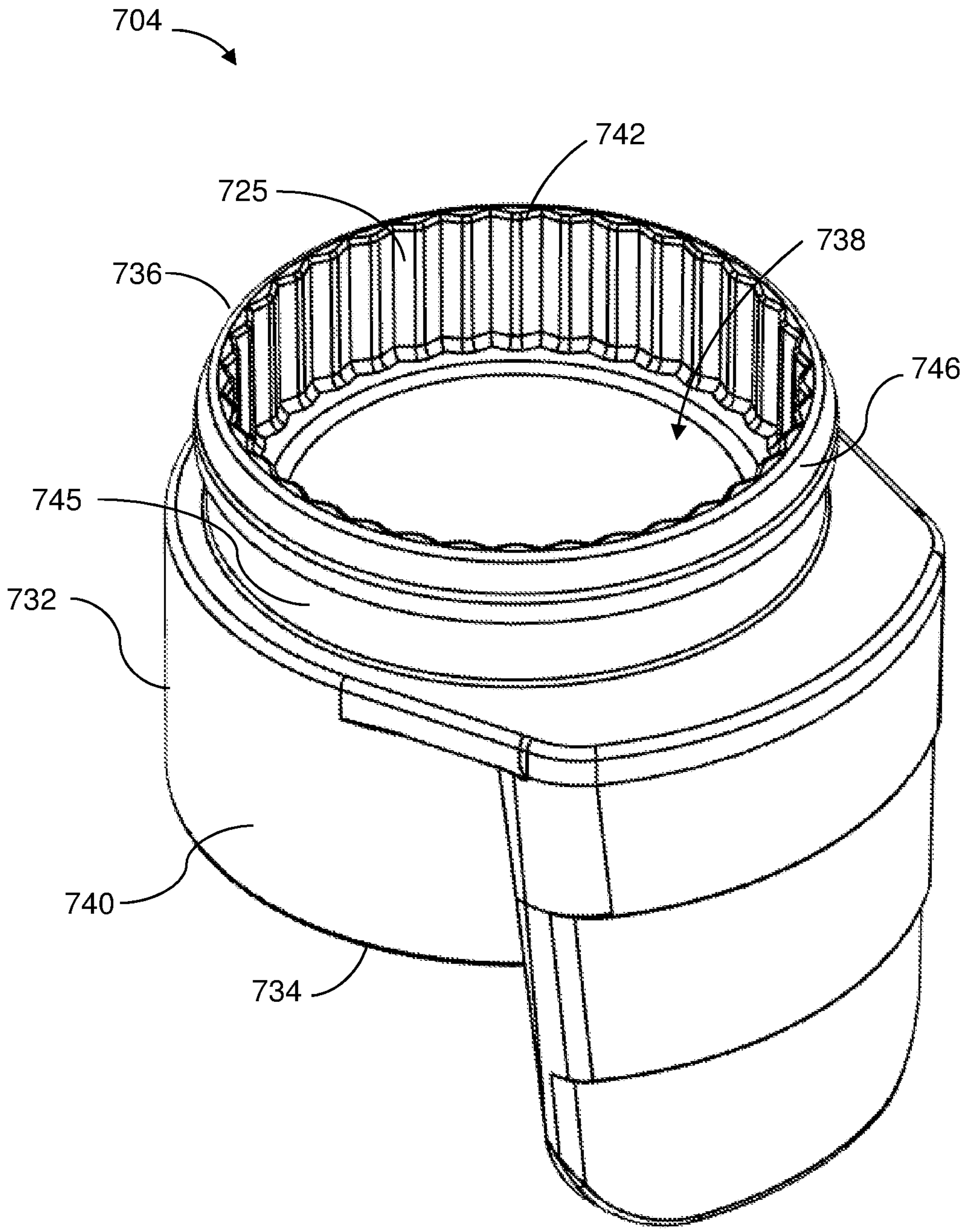
FIG. 25 illustrates a perspective view of a cap in accordance with a seventh embodiment of the present disclosure.
Figure 26:
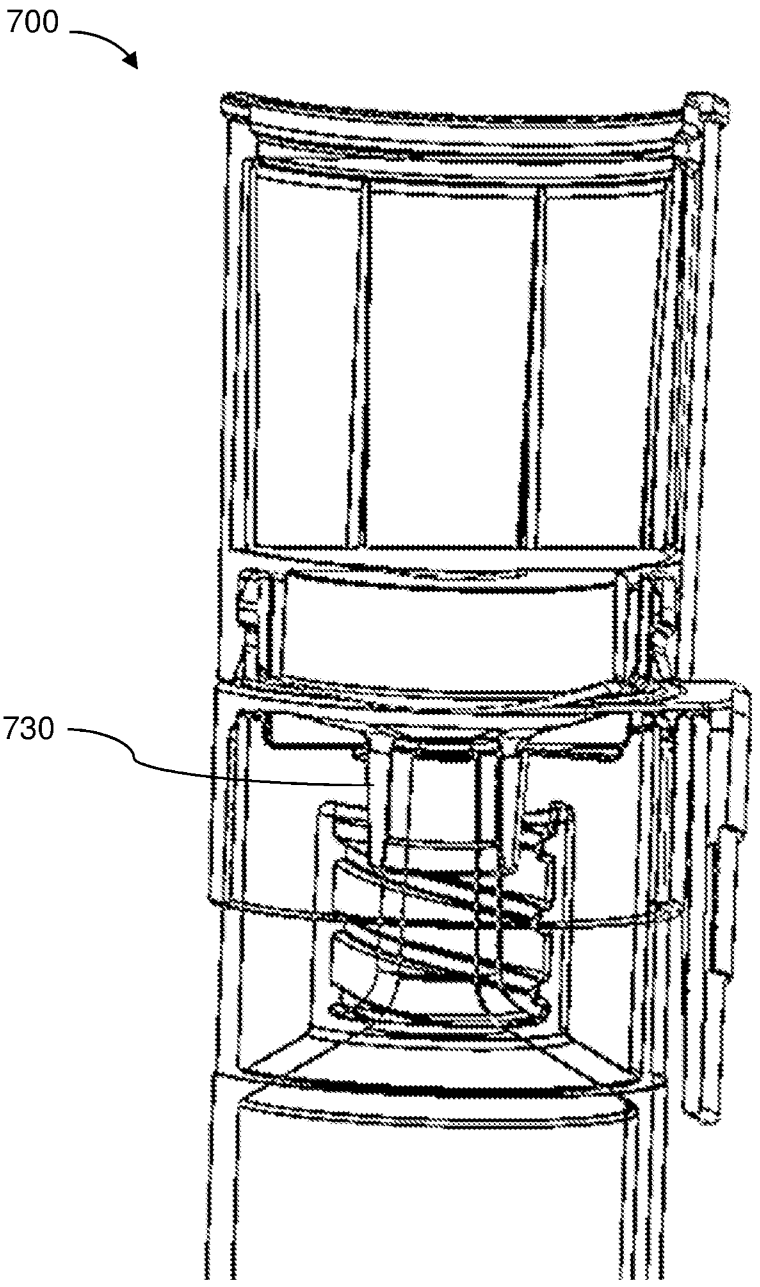
FIG. 26 illustrates a cross-sectional view of a an integrated disinfection syringe tip cap assembly in accordance with a seventh embodiment of the present disclosure.
Figure 27:
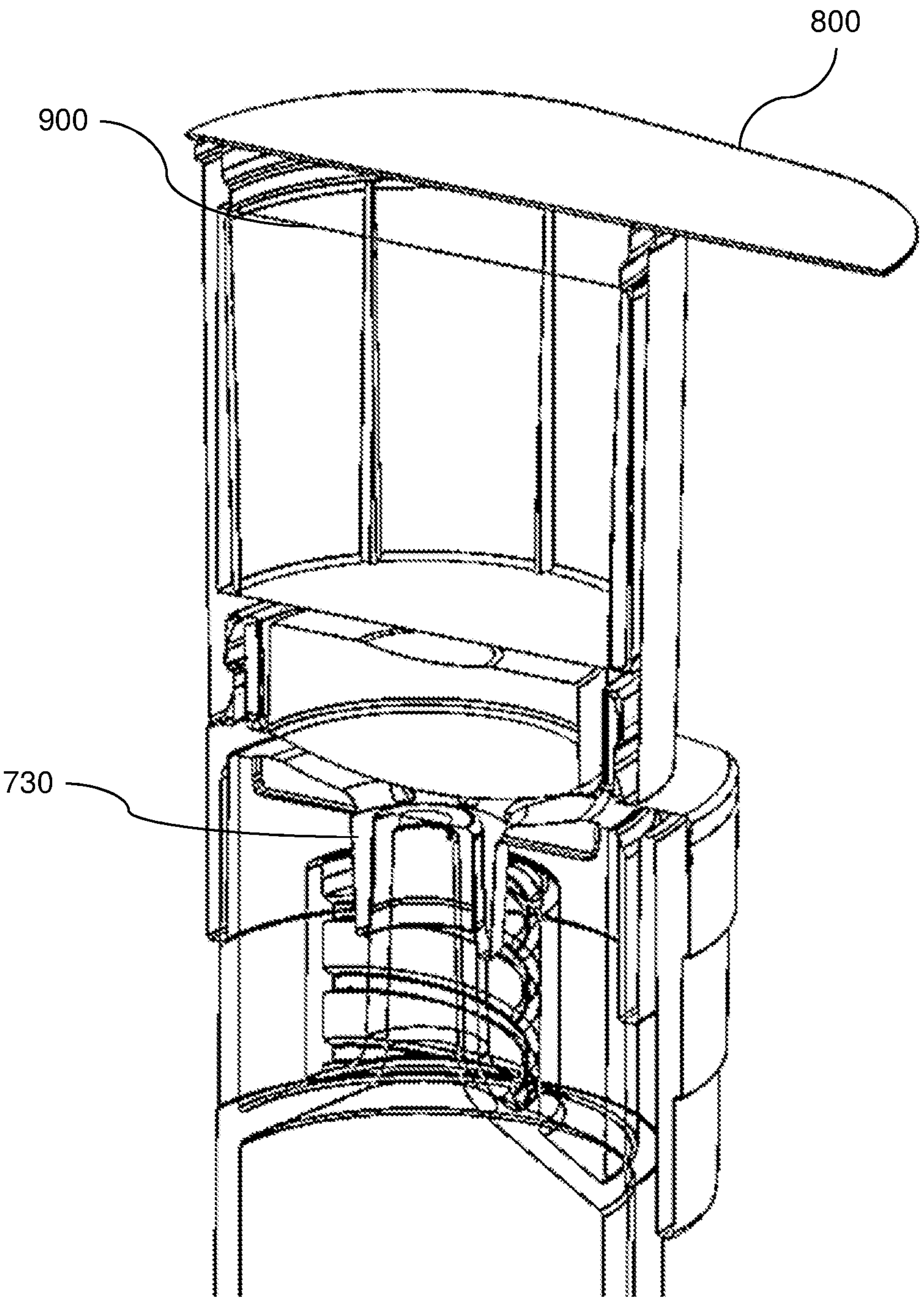
FIG. 27 illustrates a cross-sectional view of a an integrated disinfection syringe tip cap assembly in accordance with an embodiment of the present disclosure.
Figure 28:
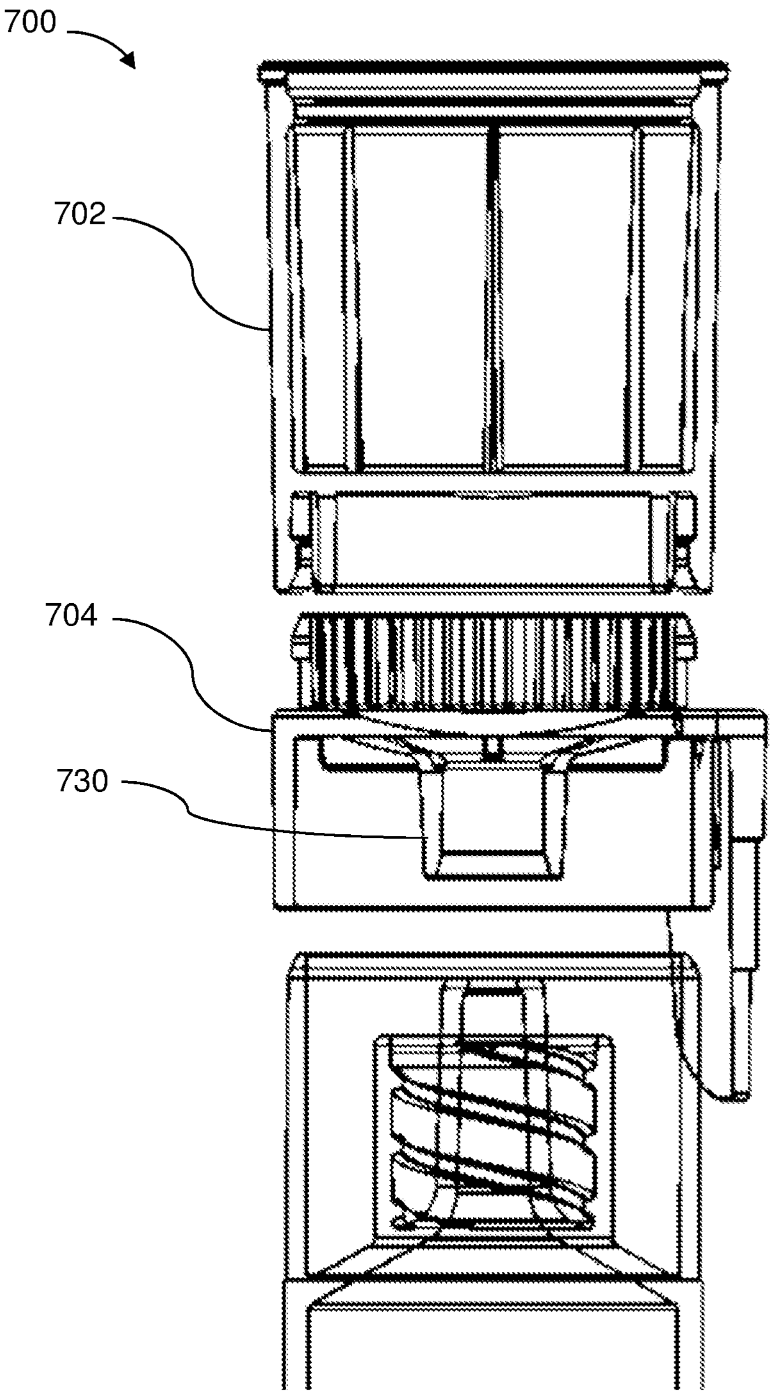
FIG. 28 illustrates a cross-sectional view of a an integrated disinfection syringe tip cap assembly in accordance with a seventh embodiment of the present disclosure.

Referring to FIGS. 25 and 25*a*, the cap 704 comprises an integral body, an annular wall 732 having a length L(g) extending from the bottom end 734 to an top end 736 that defines a chamber 738. The annular wall 732 comprises of an exterior wall surface 740 and an interior wall surface 742. On the exterior wall surface 740, adjacent to the top end 736, exists a beveled rim 746. Underneath the beveled rim 746 exists a collar 745. The chamber 738 is appropriately sized to adapt to the inner skirt 720*b* of the cup 702. The interior wall surface 742 comprises of a plurality of alignment teeth 725. The alignment teeth 725 are spaced evenly along the interior wall surface 742 of the annular wall 732; however, the alignment teeth 725 may take up only a partial surface of the interior wall surface 742.

In general, as the cap 704 and the cup 702 are assembled, the outer skirt 720*a* flex outward until they engage a beveled rim 746 on the exterior wall surface 740 on the top of the cap 704. Once the lip 723 clear the beveled rim 746, the outer skirt 720*a* springs inward-creating a lock between the cap 704 and the cup 702.

Specifically, during assembly of the cup 702 and the cap 704, the closed end 710 of the cup 702 is inserted onto the top end 736 of the cap 704. As the cup 702 is forced onto the cap 704, the beveled rim 746 cause the outer skirt 720*a* to flex outward. Simultaneously, the inner skirt 720*b* inserts into the chamber 738 of the cap 704. Once the lips 723 of the outer skirt 720*a* clear the beveled rim 746, the outer skirt 720*a* springs inward. The lips 723 fit into the collar 745 of the cap 704, creating a lock between the cap 704 and the cup 702. The alignment teeth 739 of the cup 702 and the alignment teeth 725 of the cap 704 guide the two components during the assembly process as well as prohibit the cap 704 from rotating relative to the cup 702 to ensure smooth and accurate assembly. Additionally, the components can be assembled universally and do not require specific orientation.

Referring to FIGS. 26-33, an assembly of one or more of the embodiments is shown.

In one or more embodiments, the cap 704 includes a fluid type connection element 730 to allow the assembled cup and cap to be connected to a syringe. In one or more embodiments, the fluid type connection element 730 is a luer slip, as shown in FIGS. 26-29. In one or more embodiments, the fluid type connection is a threaded connection, for example, luer threaded connection. The cap 704 may include a luer slip connection, as shown in FIGS. 26-29, or a threaded luer lock connection (not shown) to allow the assembled cup and cap to be connected to a syringe.

In one or more embodiments, shown in FIGS. 27, 29, 31, and 33, a removable seal 800 may be disposed on the open distal end of the tip cap or the open end of the cup. The removable seal 800 may be a peelable seal. In one or more embodiments, the removable seal 800 may be an aluminum or multi-layer polymer film peel back top. The seal can be a plastic sealed aluminum, and can be chemically-resistant, light-blocking, non-permeable, or sterile. The removable seal 800 prevents the prefilled flush solution or antimicrobial solution from exiting the chamber of the cup or cap. In one or more embodiments, the removable seal 800 is heat-sealed or induction sealed to the open end of the cup or cap. In one or more embodiments, the removable seal 800 comprises a moisture barrier.

Figure 29:
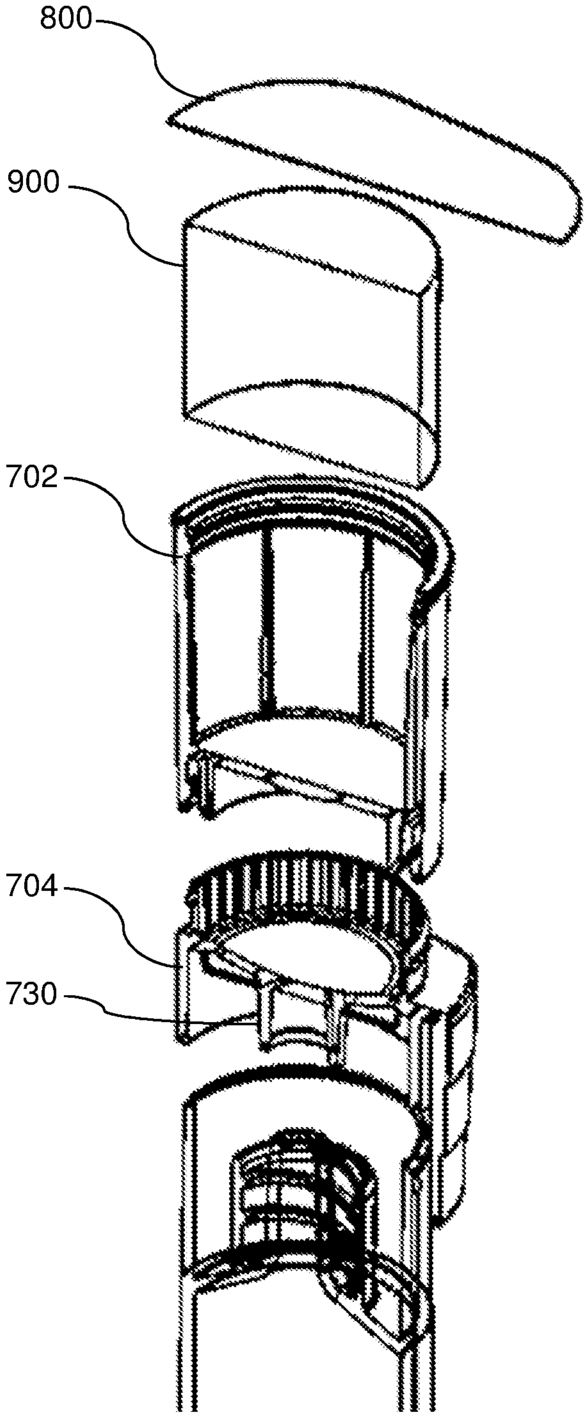
FIG. 29 illustrates an exploded view of a an integrated disinfection syringe tip cap assembly in accordance with a seventh embodiment of the present disclosure.
Figure 30:
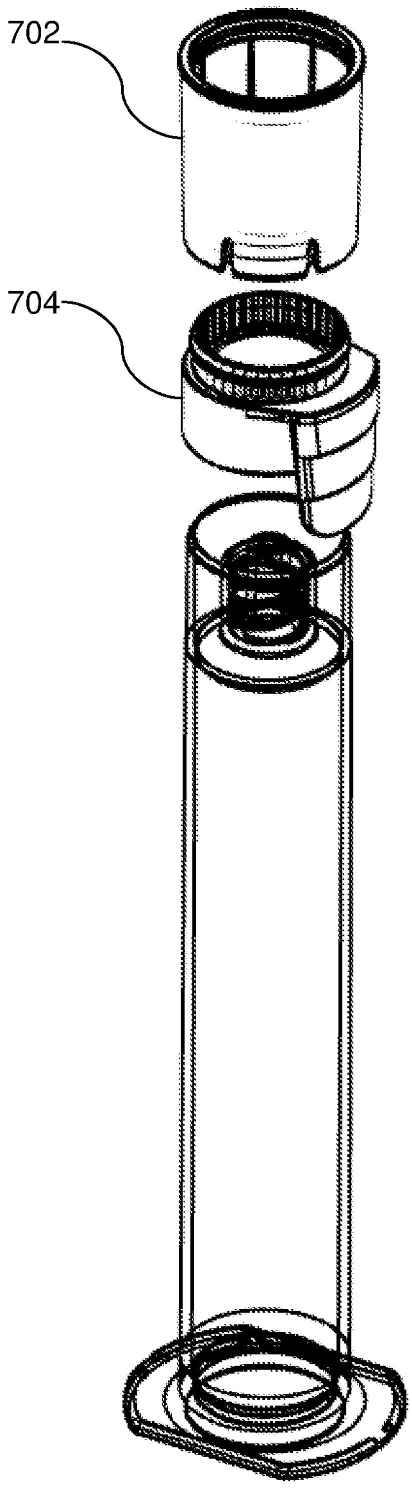
FIG. 30 illustrates an exploded view of a an integrated disinfection syringe tip cap assembly in accordance with a seventh embodiment of the present disclosure.
Figure 31:
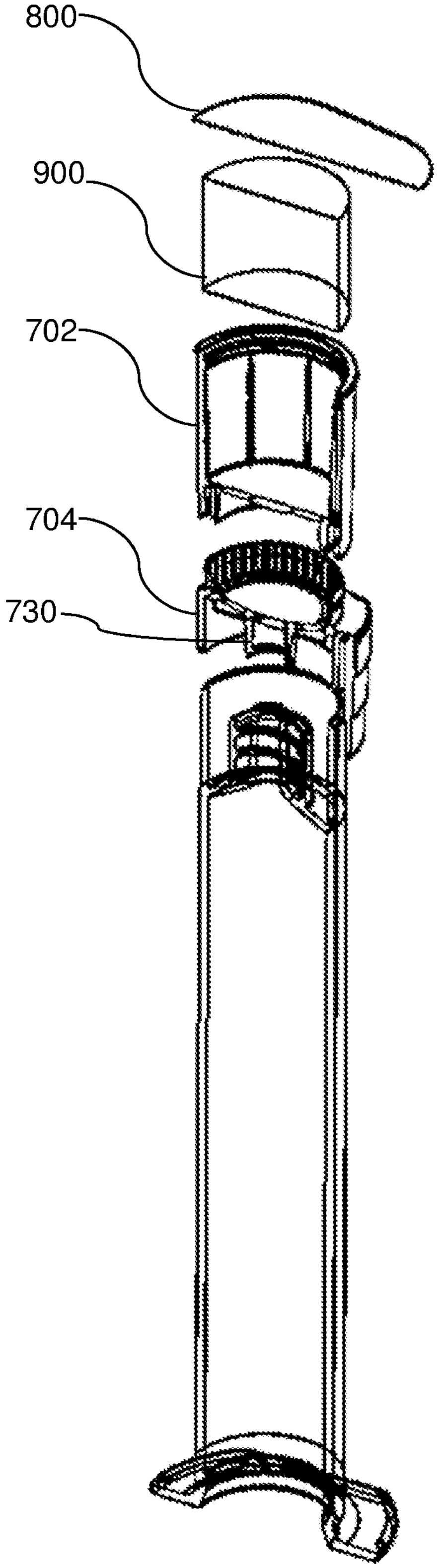
FIG. 31 illustrates a cross-sectional exploded view of a an integrated disinfection syringe tip cap assembly in accordance with a seventh embodiment of the present disclosure.
Figure 32:
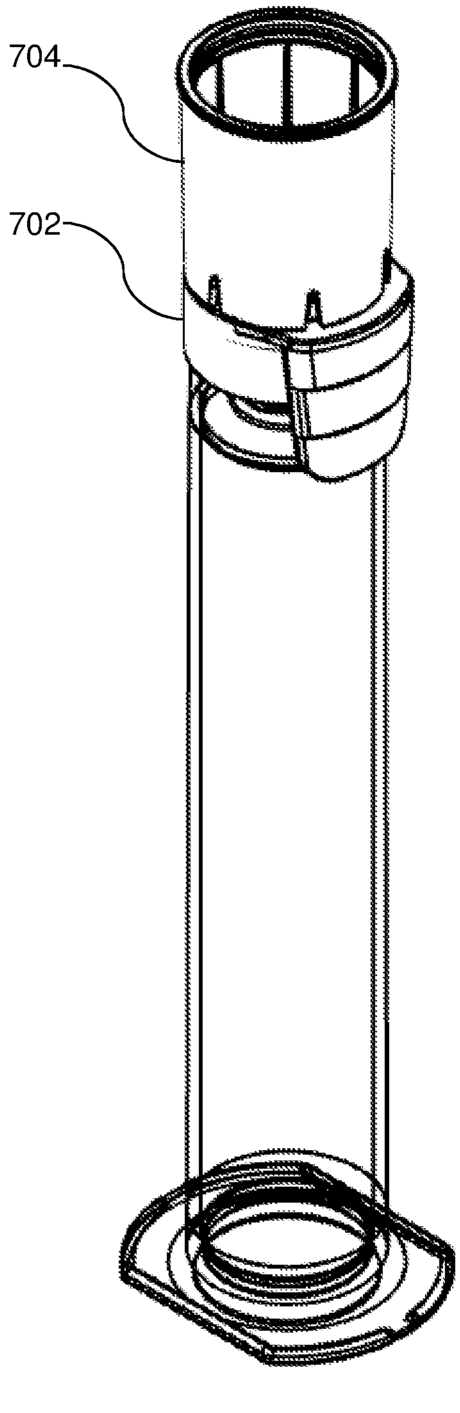
FIG. 32 illustrates a perspective view of a an integrated disinfection syringe tip cap assembly in accordance with a seventh embodiment of the present disclosure.
Figure 33:
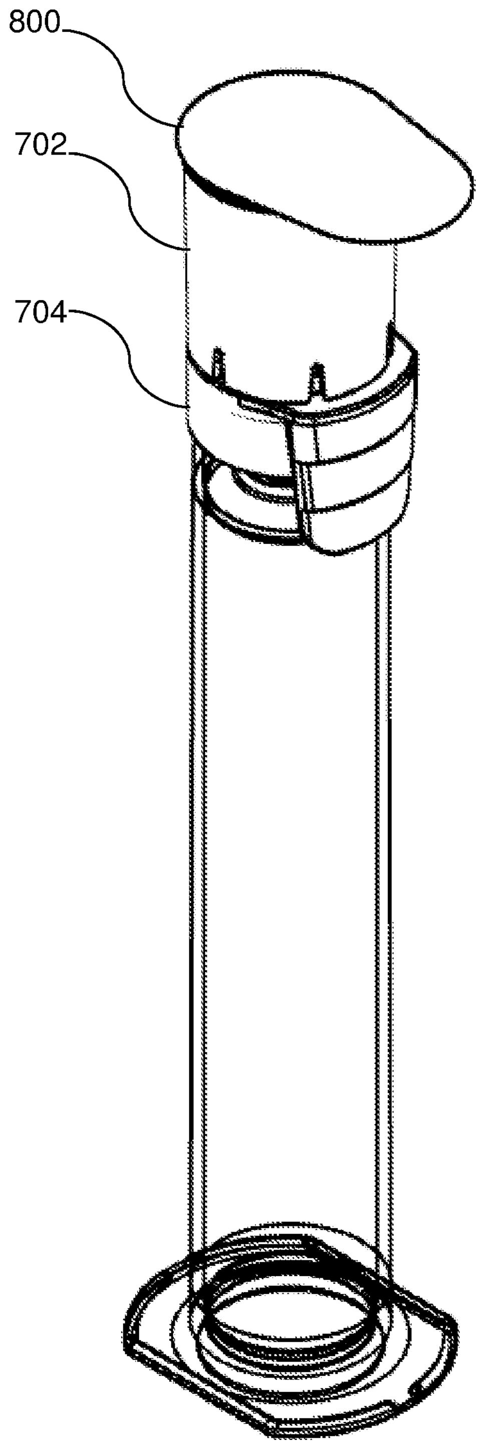
FIG. 33 illustrates a perspective view of an integrated disinfection syringe tip cap assembly in accordance with a seventh embodiment of the present disclosure.

As shown in FIGS. 29 and 31, an absorbent material 900 is disposed and housed in the chamber 714 of the cup 702. Absorbent material 900 soaks up the disinfectant or antimicrobial agent that is housed within the chamber 714 of the cup 702. In one or more embodiments, the absorbent material 900 is a nonwoven material, foam or a sponge. In a specific embodiment, the foam is a polyurethane foam. In one or more embodiments, the absorbent material 900 may include one or more grooves that are sized and adapted to receive a male luer connector, a female luer connector or a hemodialysis connector.

In one or more embodiments, the disinfectant or antimicrobial agent is selected from the group consisting essentially of isopropyl alcohol (IPA), ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more embodiments, the disinfectant or antimicrobial agent may include variations of alcohol or chlorhexidine. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

As shown in FIGS. 34-68, another aspect of the present disclosure pertains to an assembly 1010 of a syringe tip cap (TP) and an IV access port disinfecting unit (DU) having mechanical mating features that facilitate automated assembly. Once assembled together by an axial force, the assembly of the syringe tip cap and the IV access port disinfecting unit can withstand, axial, radial, disassembly forces, while maintaining container closure integrity for the syringes fluid path. To remove the assembly of the tip cap and disinfecting unit from the syringe barrel, the user shall apply a torque on the entire assembly thus unthreading it from the barrel for use on the catheter line. In one or more embodiments, the IV access port disinfecting unit is in the form of a cup.

Figure 34:
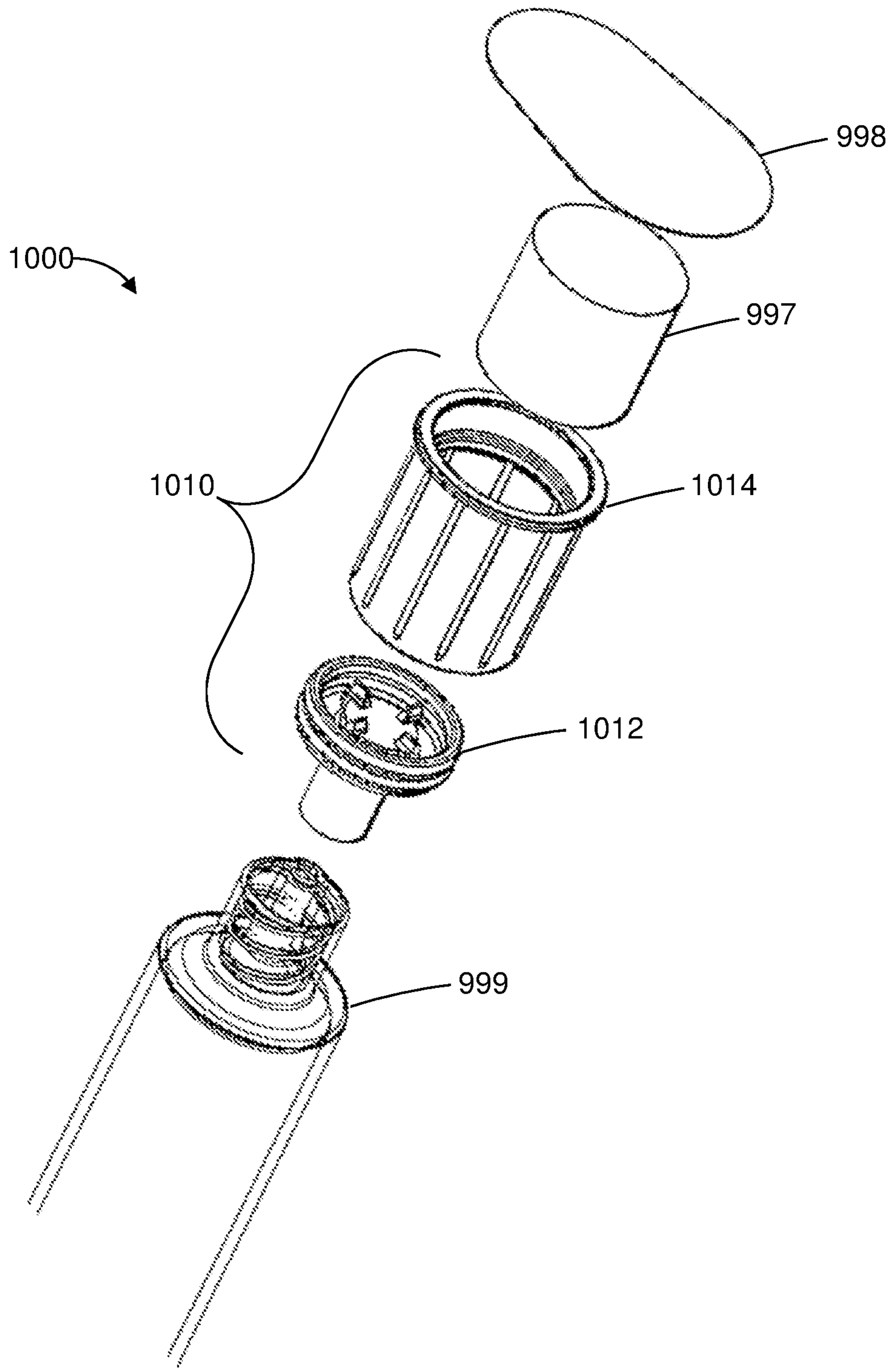
FIG. 34 illustrates an exploded view of an assembly of an integrated disinfection unit and tip cap in accordance with an eighth embodiment of the present disclosure.
Figure 35:
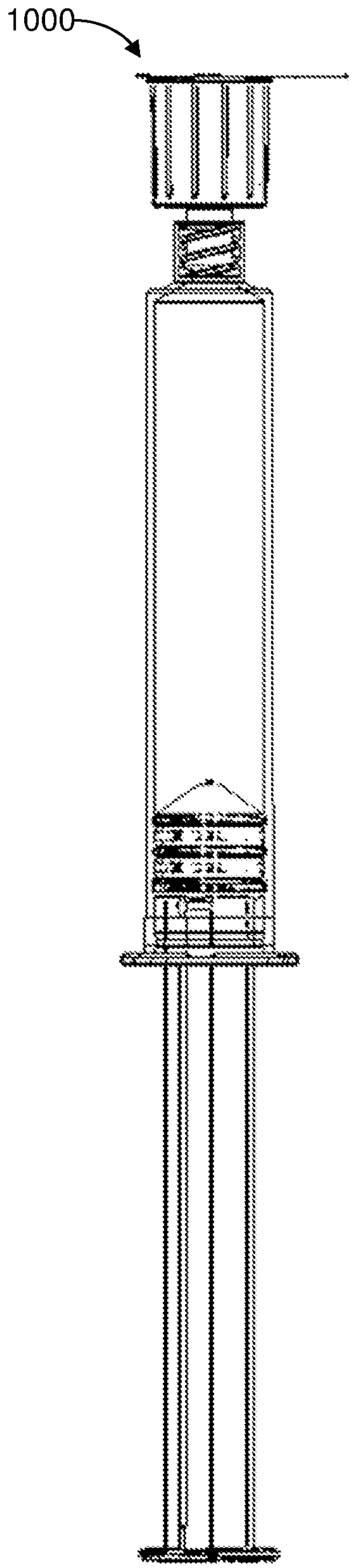
FIG. 35 illustrates a side view of an assembly of an integrated disinfection unit and tip cap in accordance with an eighth embodiment of the present disclosure.
Figure 36:
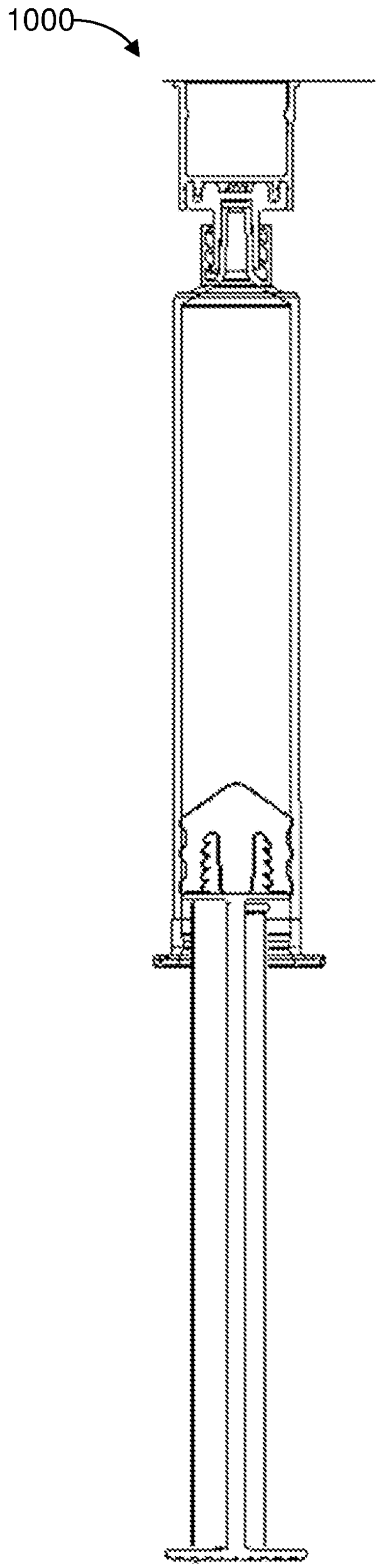
FIG. 36 illustrates a cross-sectional view of an assembly of an integrated disinfection unit and tip cap in accordance with an eighth embodiment of the present disclosure.
Figure 37:
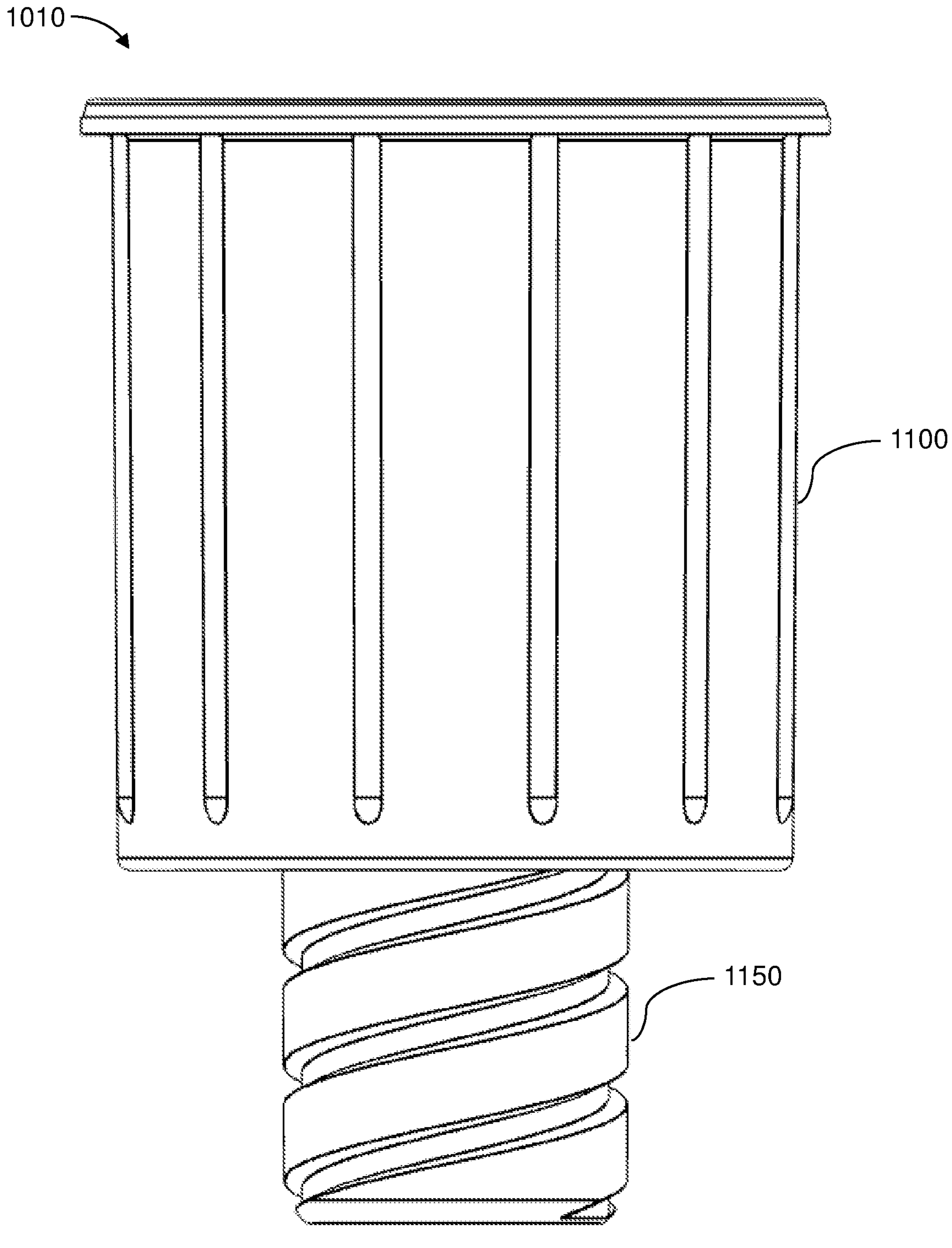
FIG. 37 illustrates a side view of an integrated disinfection unit and tip cap assembly in accordance with an eighth embodiment of the present disclosure.
Figure 38:
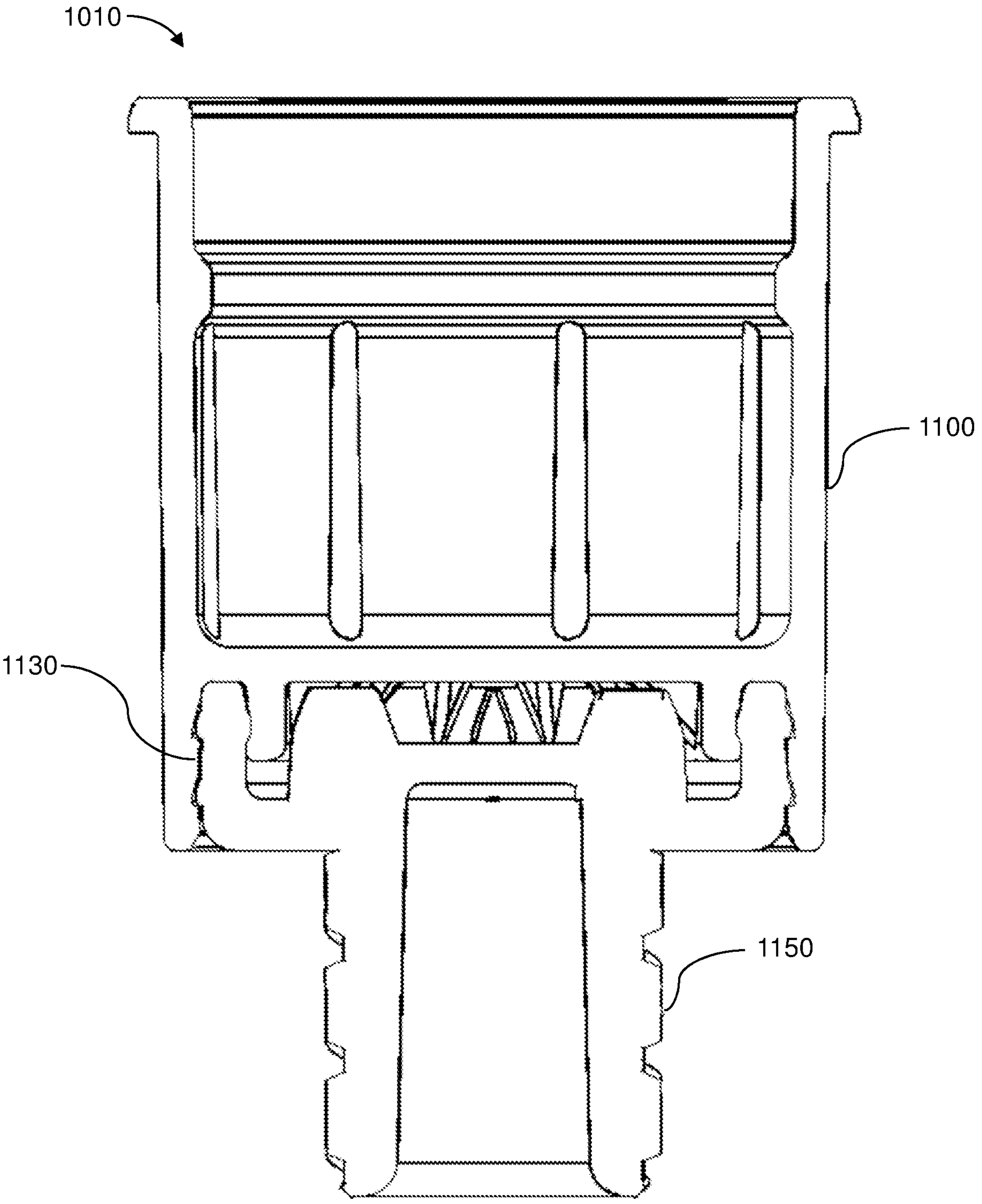
FIG. 38 illustrates a cross-sectional view of an integrated disinfection unit and tip cap assembly in accordance with an eighth embodiment of the present disclosure.
Figure 39:
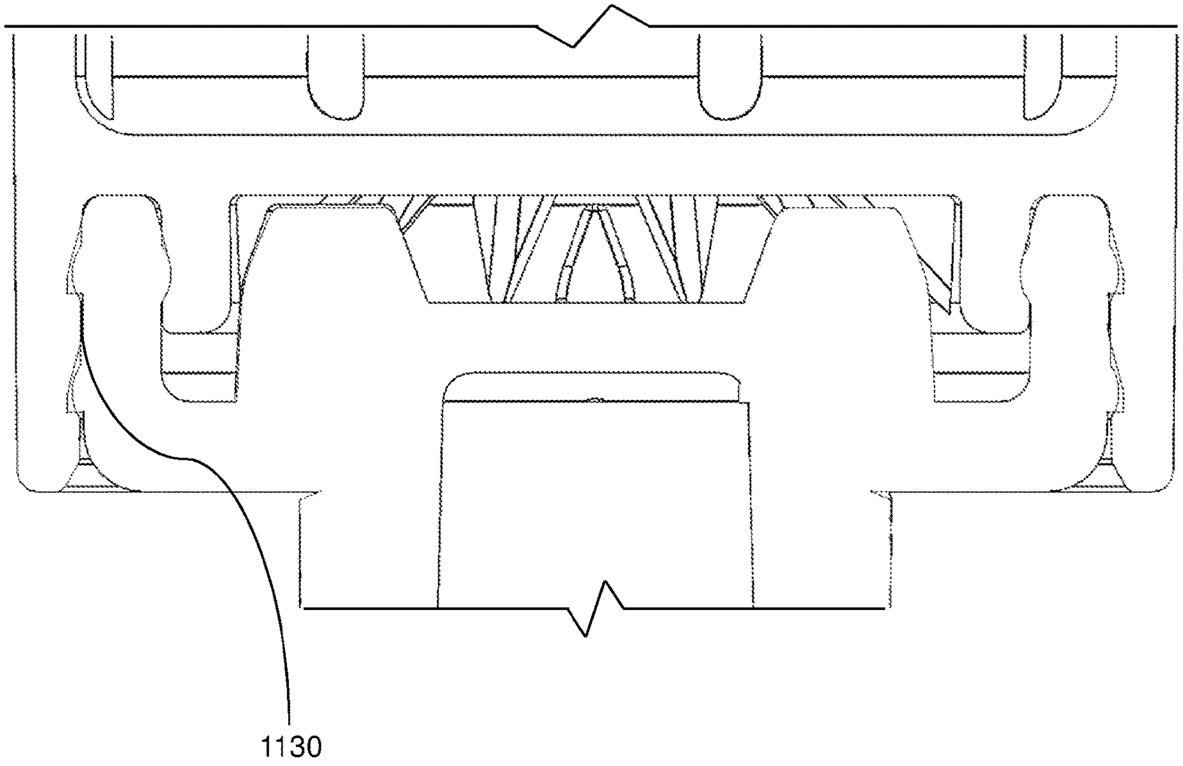
FIG. 39 illustrates a partial cross-sectional view of tip cap of FIG. 38 in accordance with a eighth embodiment of the present disclosure.
Figure 40:
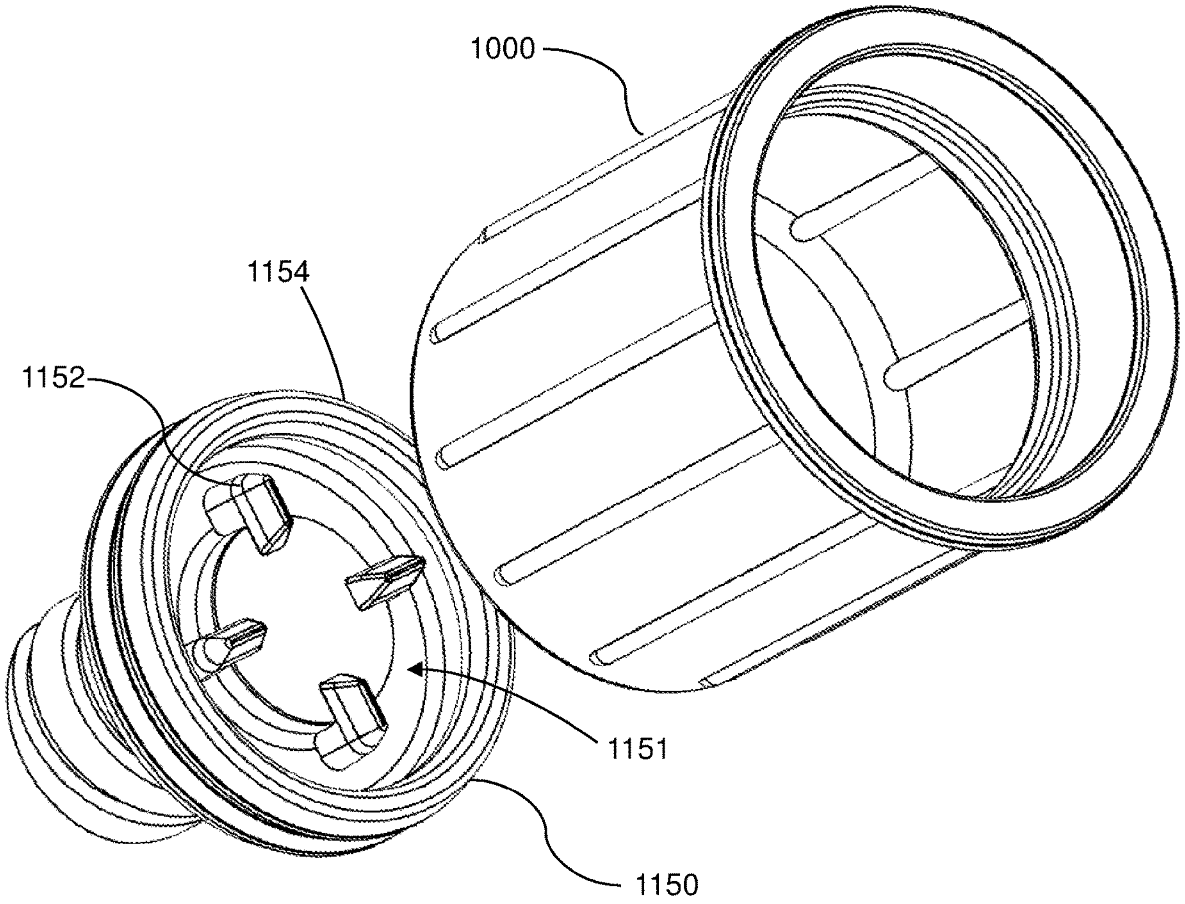
FIG. 40 illustrates an exploded perspective view of an disinfection unit and tip cap assembly shown in FIGS. 37-39 in accordance with a eighth embodiment of the present disclosure.
Figure 41:
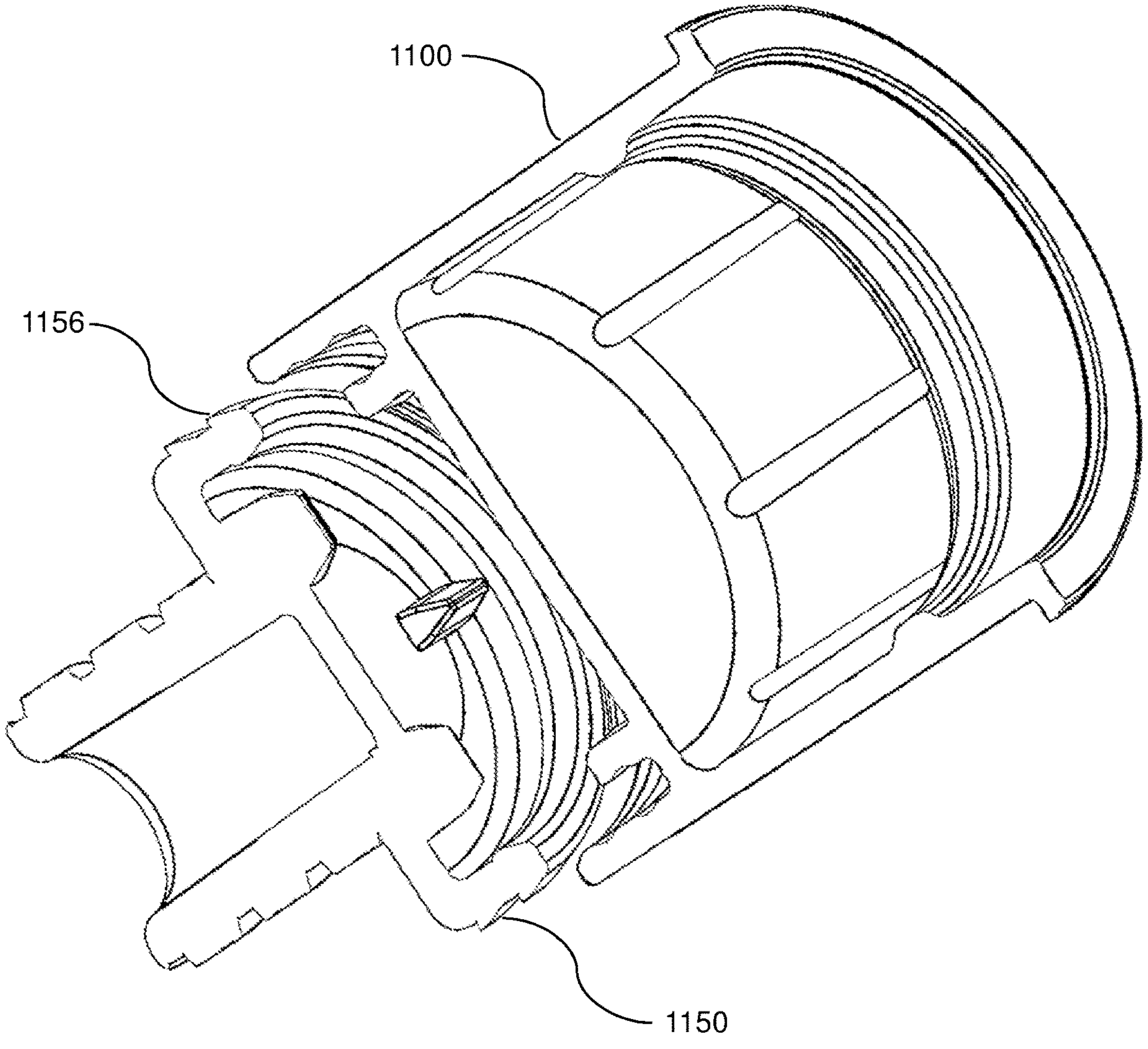
FIG. 41 illustrates a cross-sectional view of an integrated disinfection unit and tip cap assembly in accordance with an eighth embodiment of the present disclosure shown in FIGS. 37-40.

As shown in FIGS. 34-36, the assembly 1010 of a syringe tip cap 1012 (TP) and IV access port disinfecting unit 1014 (DU), in all its embodiments of the present disclosure couples the syringe tip cap 1012 (TP) to the disinfecting unit 1014 (DU). The assembly 1010 of a syringe tip cap 1012 (TP) and IV access port disinfecting unit 1014 (DU) ensures that the user will not need to flip the device over when wanting to disinfect or perform a flush procedure. This not only improves clinician workflow but reduces the risk of potential contamination when flipping the device over. In addition, the assembly 1010 of the syringe tip cap 1012 (TP) and IV access port disinfecting unit 1014 (DU) of the present disclosure does not require a “cradle” or other device to assembly the devices together.

The assembly 1010 of a syringe tip cap 1012 (TP) and IV access port disinfecting unit 1100 (DU) facilitates high speed, automated assembly. The assembly of a syringe tip cap 1012 (TP) and IV access port disinfecting unit 1014 (DU) ensures device integrity when an axial, radial, or torsional disassembly forces is applied post assembly.

As shown in FIGS. 34-36, the assembly 1010 of the syringe tip cap 1012 (TP) and the IV access port disinfecting unit 1014 is designed to sit on a syringe barrel 999 and maintain sterility and container closure integrity (CCI) for the shelf life of the product. In one or more embodiments, the assembly 1010 of the syringe tip cap 1012 (TP) and the IV access port disinfecting unit 1014 may contain a disinfectant that can be utilized to disinfect IV access ports before a flush procedure or medication is administered. In one or more embodiments, the assembly 1010 of the syringe tip cap 1012 (TP) and IV access port disinfecting unit/cup 1014 (DU) is comprised of a syringe threaded tip cap 1012 (TC) and a disinfecting unit 1014 (DU), containing both a scrubbing foam 997 and disinfectant, such as isopropyl alcohol (IPA), and sealed with a peal-able foil lid.

As shown in FIGS. 34-68, the mating features of the seventh aspect of the present disclosure are located on the tip cap (1150, 1190, 1250, 1350, 1450, 1550, 1650) or disinfecting unit (1100, 1200, 1300, 1400, 1500, 1600) or both. The mating features ensure that once the tip cap and disinfecting unit are assembled, they shall not be easily disassembled by a axial, radial, or torsional force. In addition, the tip cap (1150, 1190, 1250, 1350, 1450, 1550, 1650) and disinfecting unit (1100, 1200, 1300, 1400, 1500, 1600) have anti-rotation features that ensure that they do not rotate freely of one another (i.e. the disinfecting unit shall not rotated as a “scrub the hub” is being performed. These anti-rotation features also ensure that once the tip cap is unthreaded the tip cap/disinfecting unit assembly shall be removed together and not as two separate pieces.

In the prior art, a disinfecting unit may be disposed on the plunger rod, opposite of a luer tip, thus requiring the user to maneuver the device at great lengths to perform a proper flush procedure, which increases the change of accidental contamination by inadvertently striking a surface or dropping the device. The device of the eighth aspect of the present disclosure has the luer tip and the disinfecting unit on the same end of the device, resulting in less maneuvering being required to use the device properly.

In the prior art, a “cradle” underside is employed under where the disinfecting unit is held resulting in the cradle being easily disassembled by a user during normal use. The device of the eighth aspect of the present disclosure, in all its embodiments explained below, does not allow access to the features that hold the tip cap and disinfecting unit together. These features are effectively hidden during and post assembly and require substantial force to separate the tip cap and disinfecting unit.

In one or more embodiments, the tip cap of the eighth aspect of the present disclosure includes geometric features that can facilitate torqueing on to a syringe during automated assembly.

In one or more embodiments, the tip cap and disinfecting unit of the eighth aspect of the present disclosure include self-aligning features to ensure that the tip cap and disinfecting unit are oriented correctly and do not jam during automated assembly.

In one or more embodiments, the tip cap and disinfecting unit of the eighth aspect of the present disclosure have mating features that can withstand high force, relative to normal use, in the axial, radial, and torsional directions and do not disassemble.

To ensure maximum scrubbing, the tip cap and disinfecting unit of the eighth aspect of the present disclosure shall include anti-rotational features ensuring they do not spring freely once assembled.

When a torque is applied to either the tip cap or disinfecting unit or both of the eighth aspect of the present disclosure, the tip cap and/or disinfecting unit assembly should unthread off the barrel as a single piece.

As shown in FIGS. 37-41, one or more embodiments of the assembly 1010 of the syringe tip cap (TP) and IV access port disinfecting unit (DU) includes a tip cap 1150 whose torqueing features 1151 are on the inner most part of the top side 1154 of the tip cap 1150. The torqueing feature 1151 includes one or more ribs 1152. In one or more embodiments, the ribs 1152 extend along a partial length on the outer diameter (OD) of the sidewall 1156 of the tip cap 1150. In one or more embodiments, the torqueing feature includes four ribs. The mating features are designed as the male undercut to the disinfecting unit’s female opening. As the devices are assembled, the undercuts 1130 will slip past each other and lock into place, once the devices are bottomed out on each other. The interference between the two undercuts 1130 is high enough that it also acts as an anti-rotational feature. In one or more embodiments, since mating surfaces are uniform 360 degrees around the part, no self-aligning features are required. In one or more embodiments, the disinfecting unit features an undercut in top-side inner diameter that aids in demolding of the piece.

Figure 42:
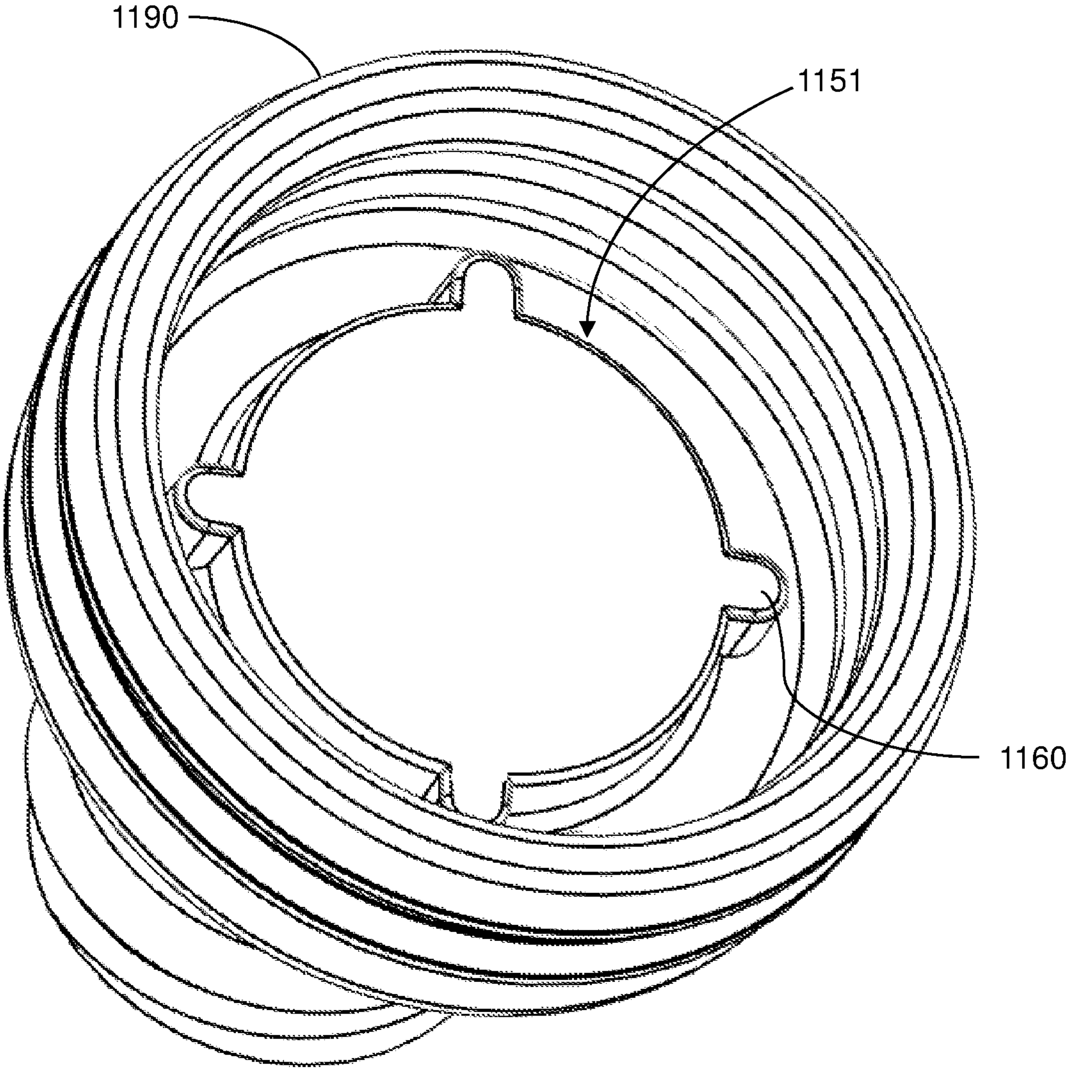
FIG. 42 illustrates a top perspective view of an integrated disinfection unit and tip cap assembly in accordance with a eighth embodiment of the present disclosure as shown in FIGS. 37-41.
Figure 43:
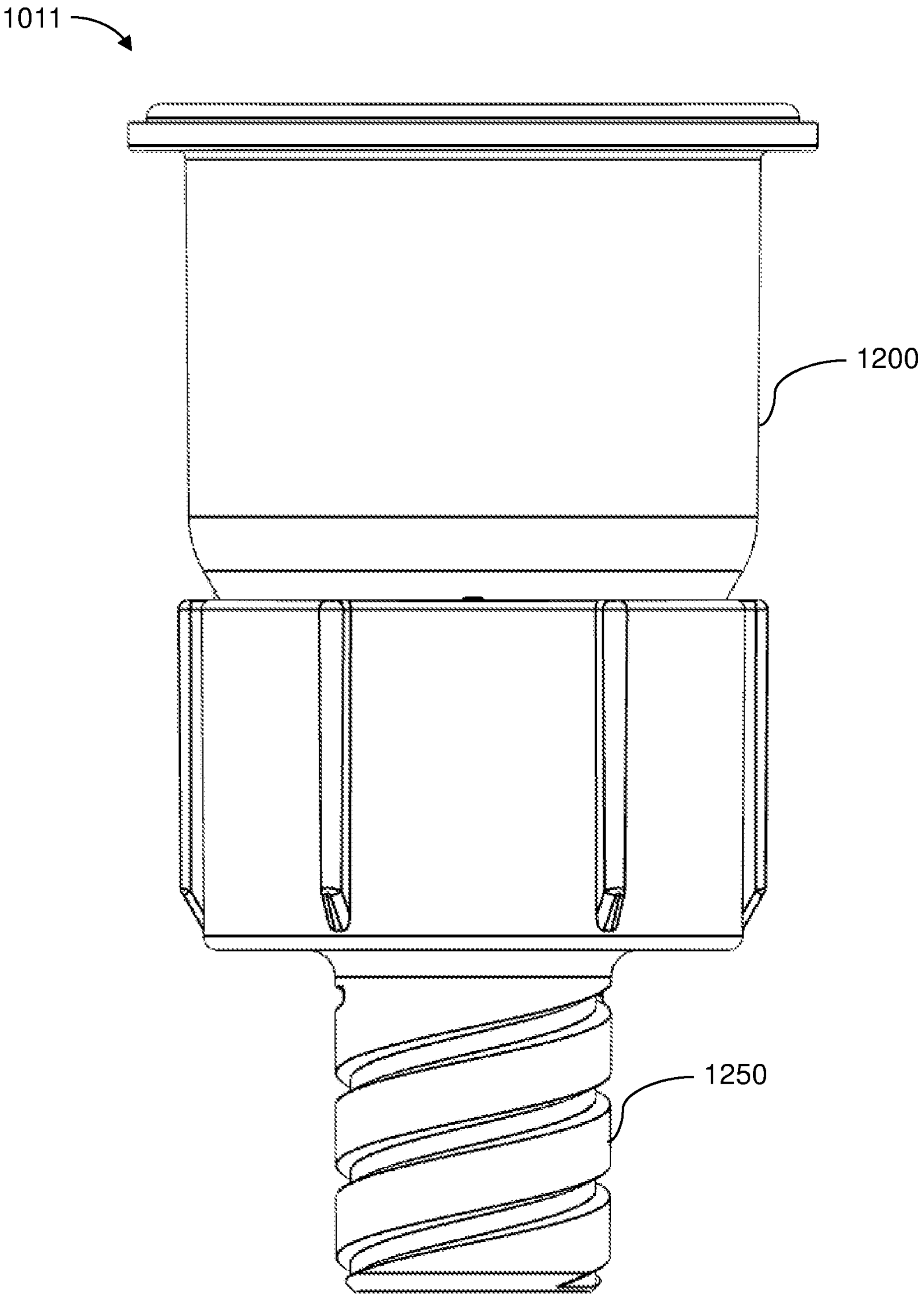
FIG. 43 illustrates a side view of an alternate integrated disinfection syringe tip cap assembly in accordance with a eighth embodiment of the present disclosure.
Figure 44:
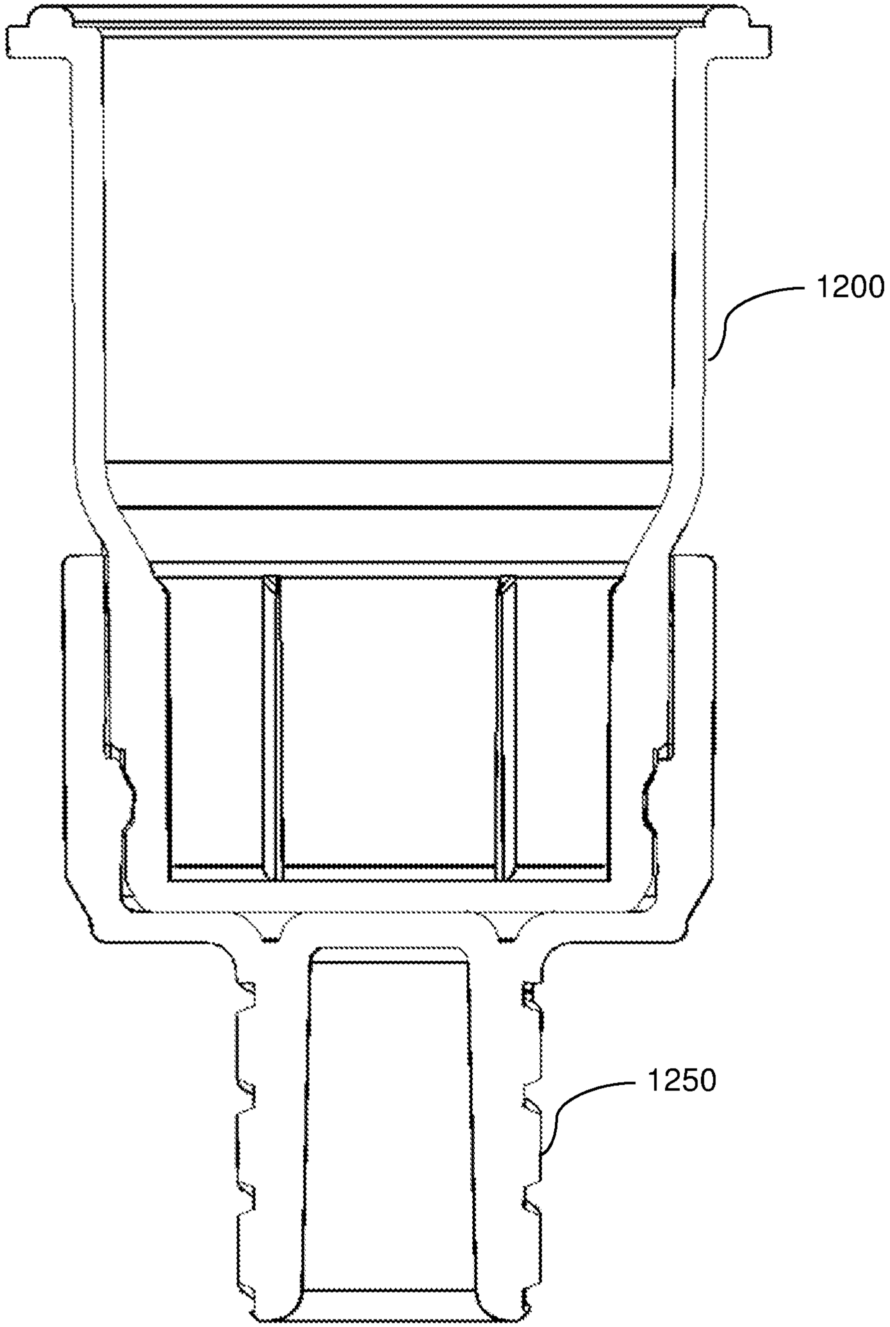
FIG. 44 illustrates a cross-sectional side view of an alternate integrated disinfection syringe tip cap assembly in accordance with a eighth embodiment of the present disclosure as shown in FIG. 43.
Figure 45:
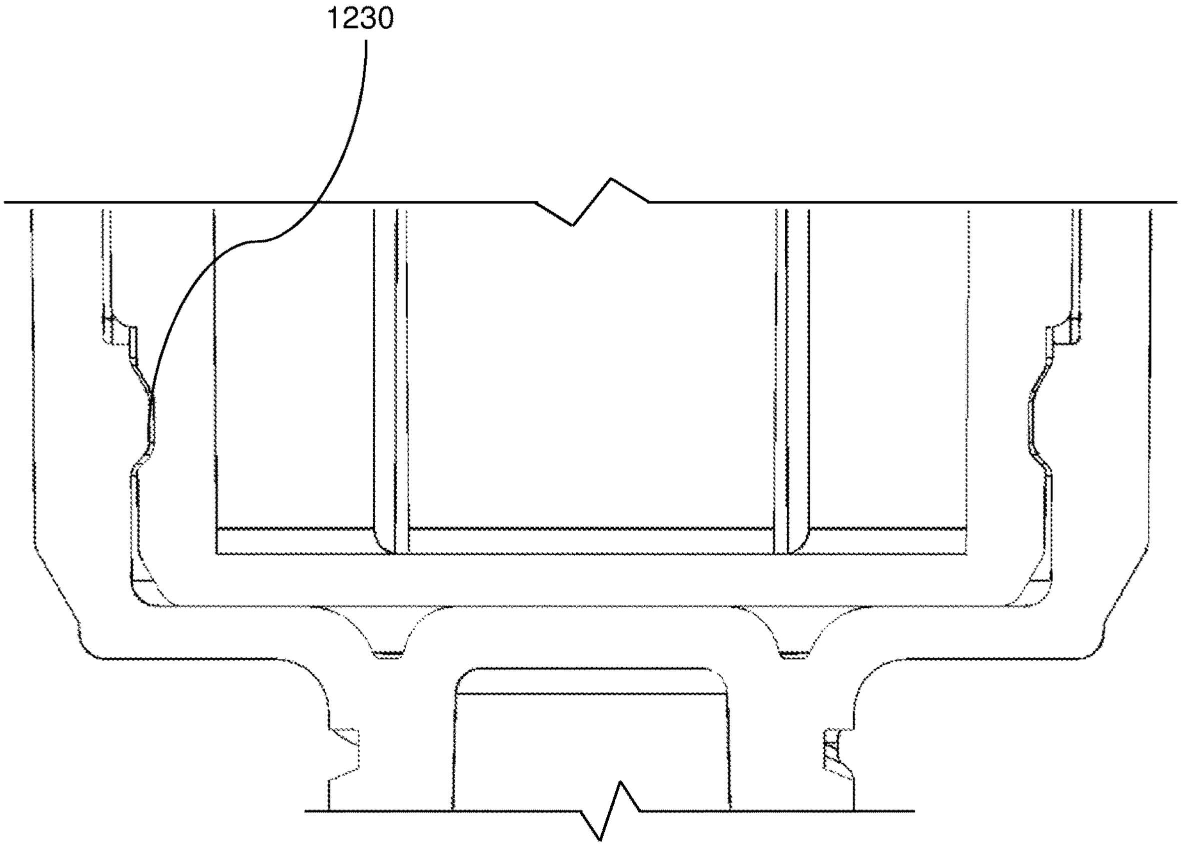
FIG. 45 illustrates a partial cross-sectional view of tip cap of FIG. 44 in accordance with a eighth embodiment of the present disclosure.
Figure 46:
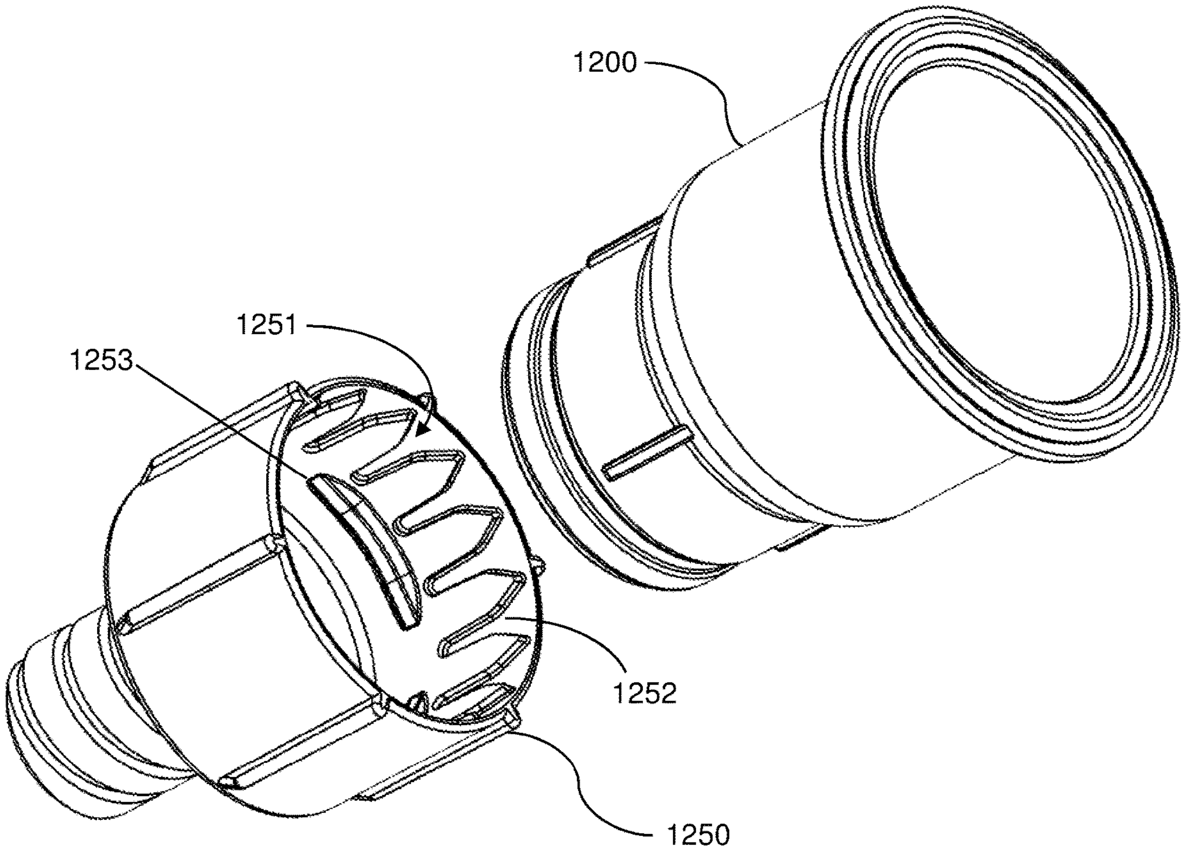
FIG. 46 illustrates an exploded perspective view of an disinfection unit and tip cap assembly shown in FIGS. 43-45 in accordance with a eighth embodiment of the present disclosure.
Figure 47:
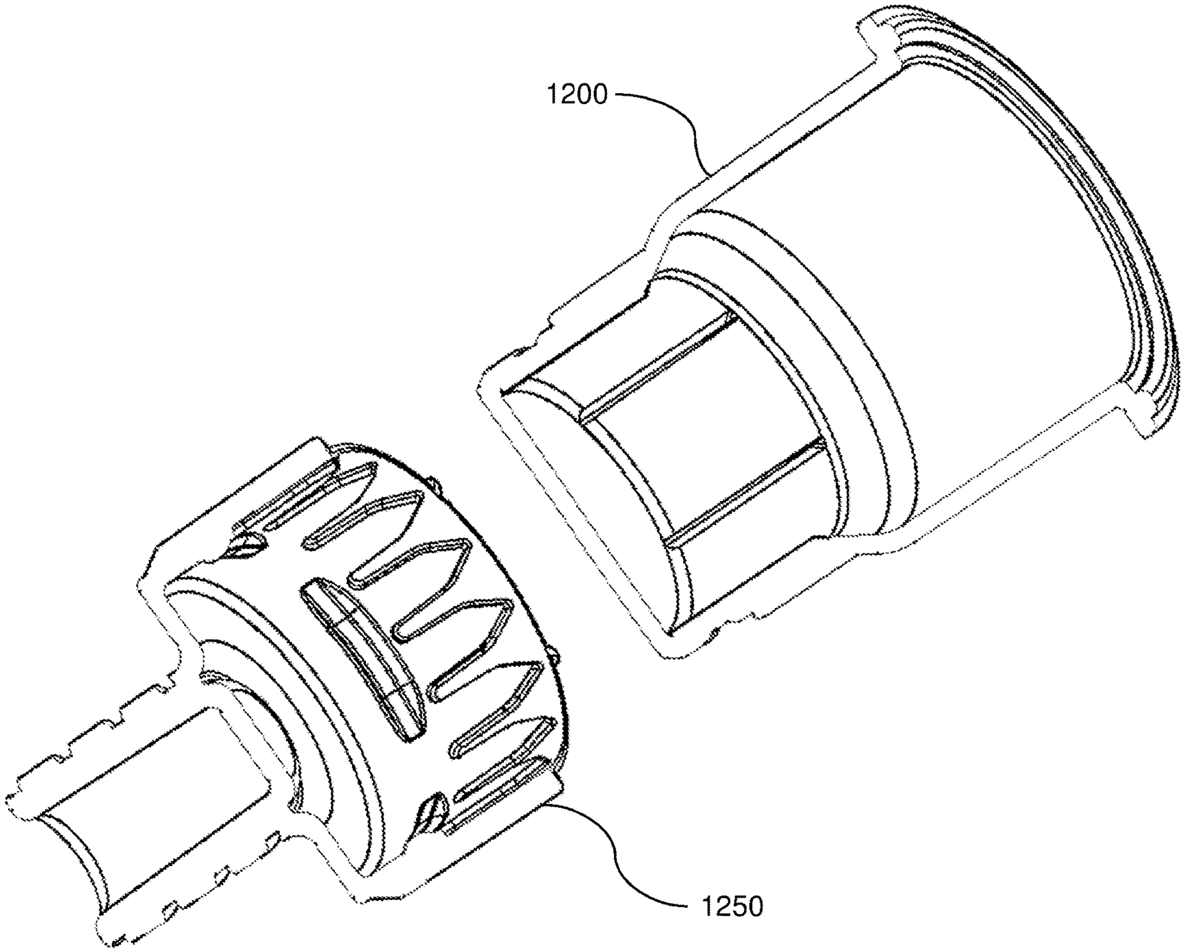
FIG. 47 illustrates an exploded cross-sectional view of an disinfection unit and tip cap assembly shown in FIGS. 43-46 in accordance with a eighth embodiment of the present disclosure.
Figure 48:
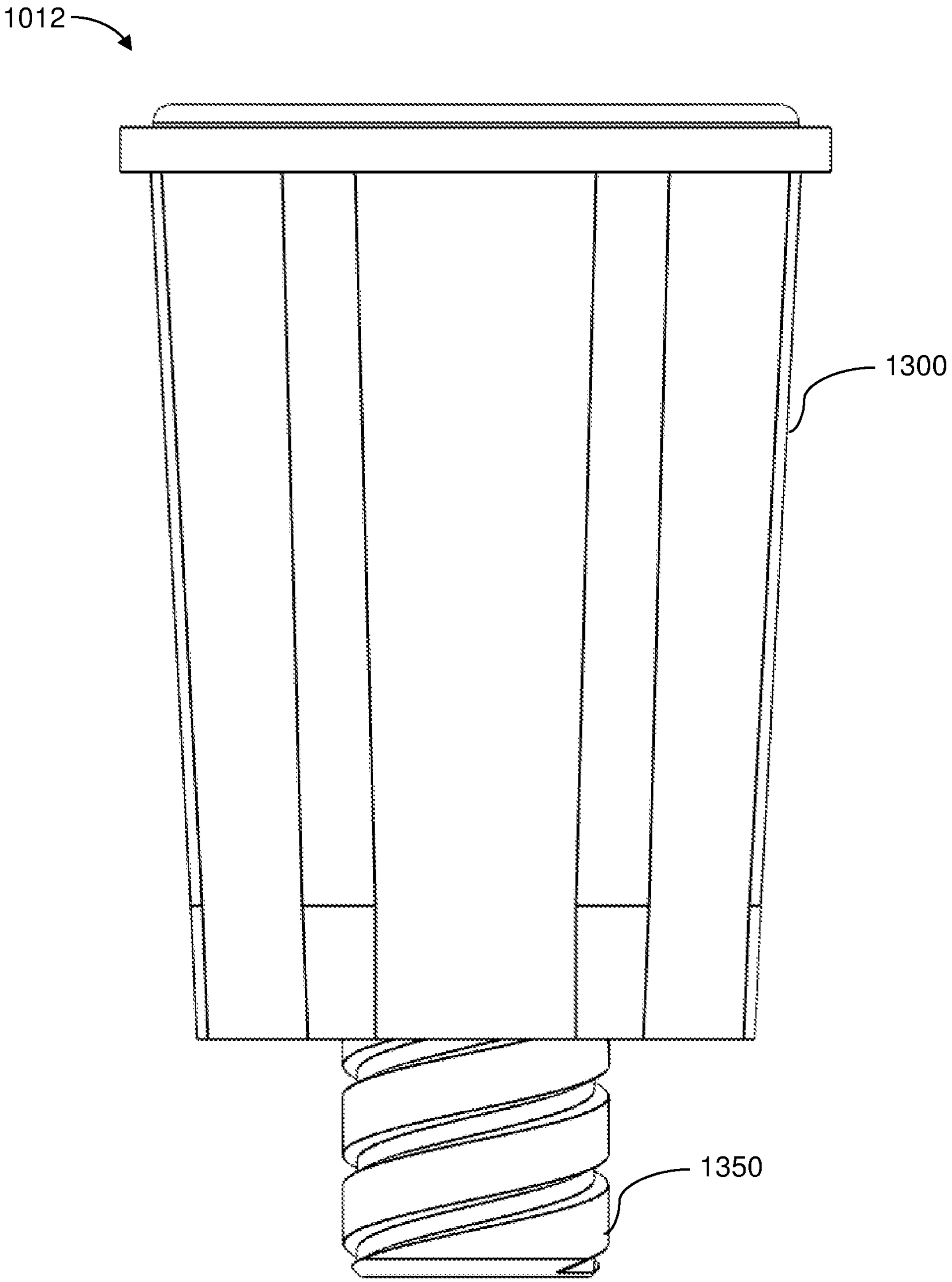
FIG. 48 illustrates a side view of another alternate integrated disinfection syringe tip cap assembly in accordance with an eighth embodiment of the present disclosure.
Figure 49:
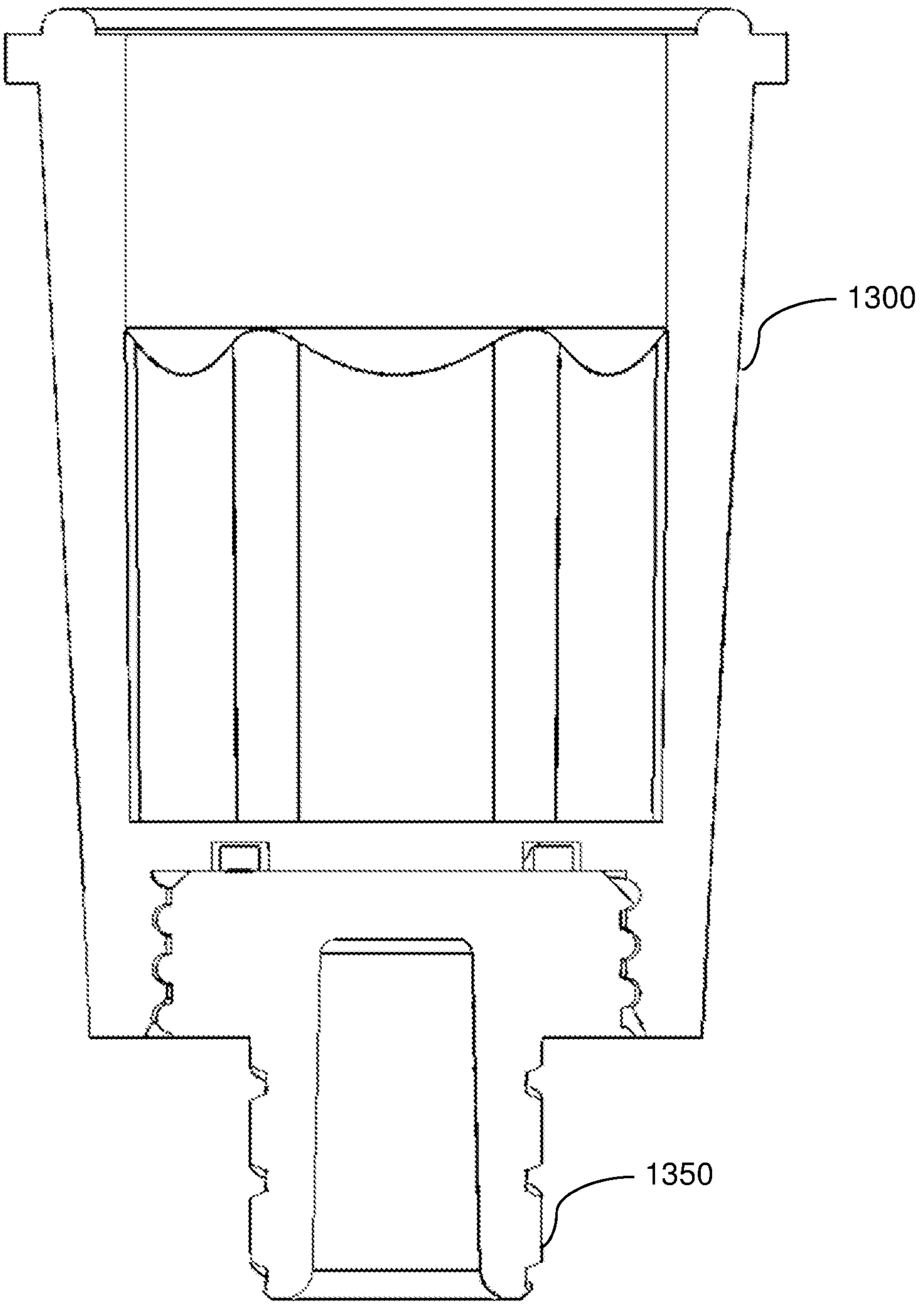
FIG. 49 illustrates a cross-sectional side view of the alternate integrated disinfection syringe tip cap assembly in accordance with a eighth embodiment of the present disclosure as shown in FIG. 48.
Figure 50:
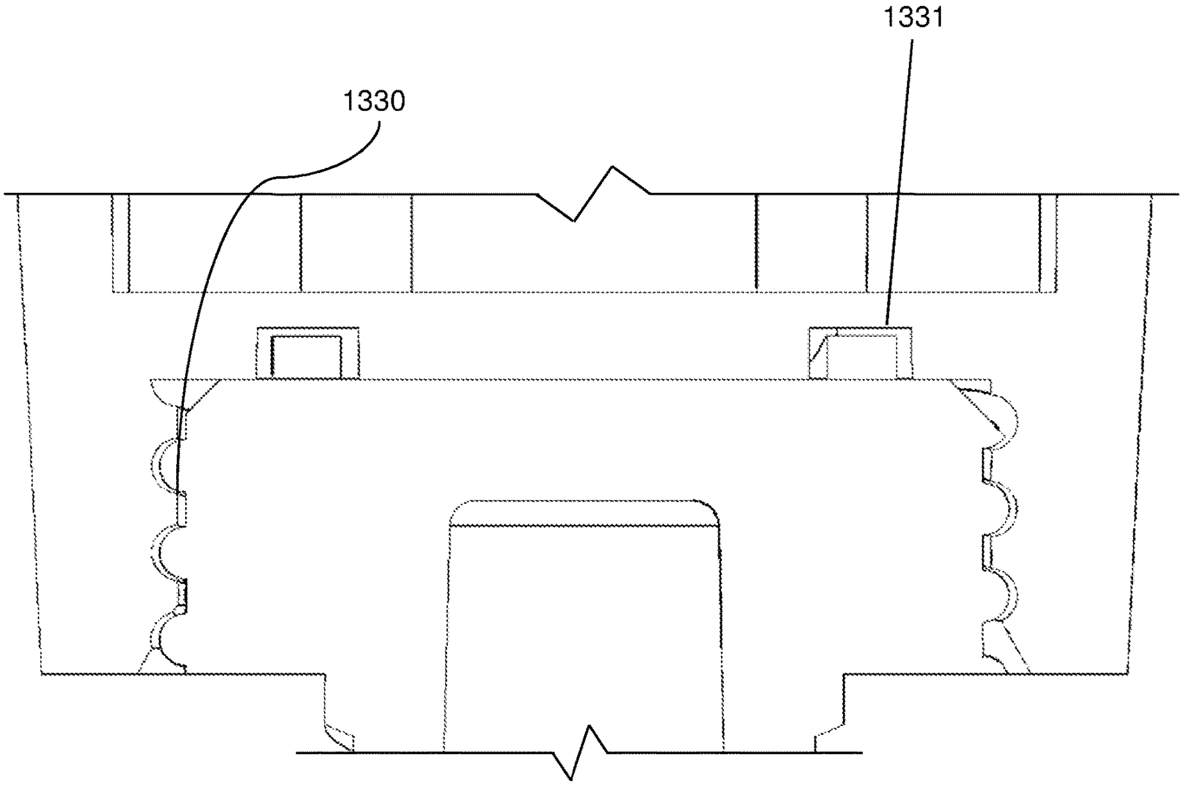
FIG. 50 illustrates a partial cross-sectional view of tip cap of FIG. 49 in accordance with a eighth embodiment of the present disclosure.
Figure 51:
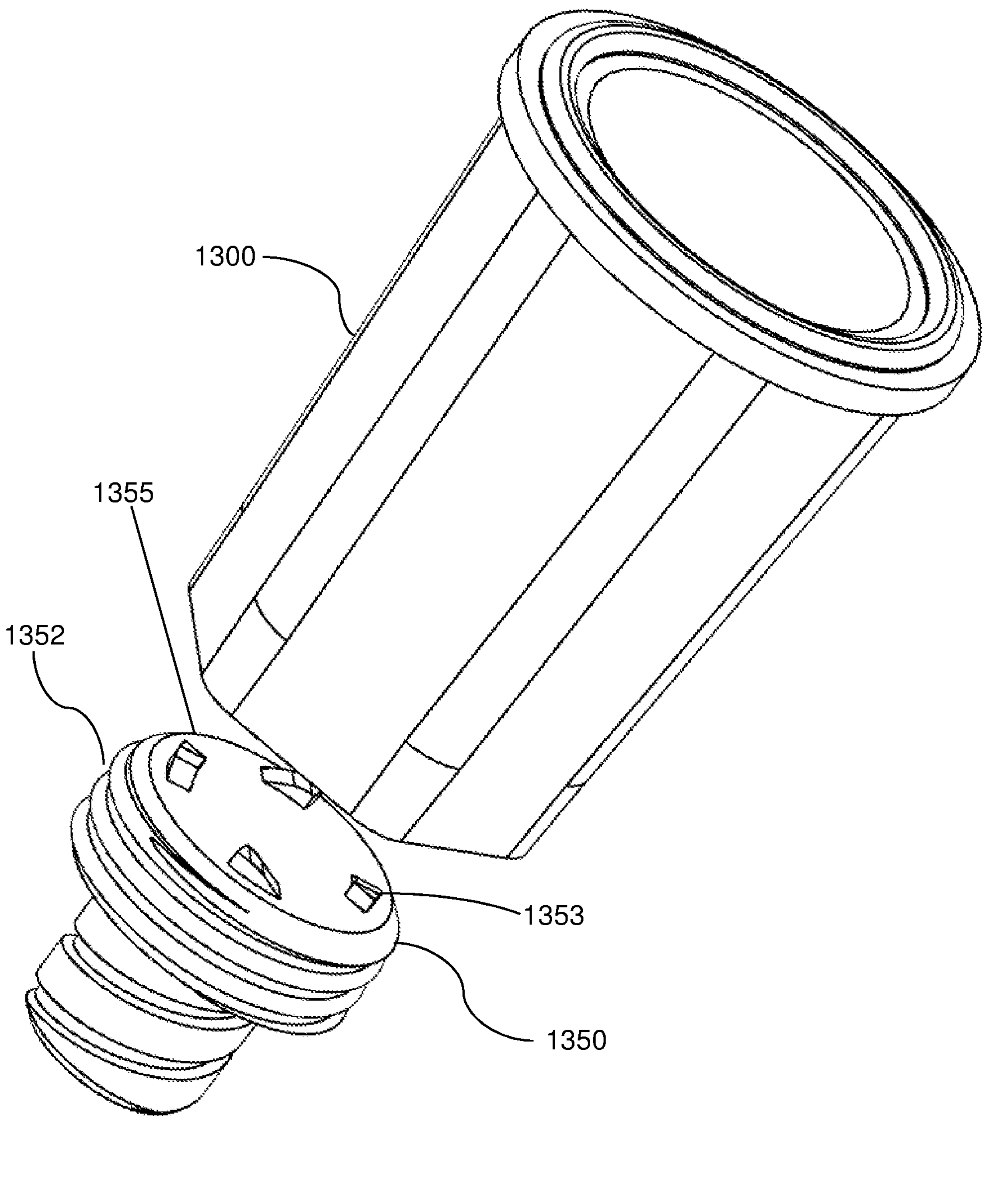
FIG. 51 illustrates an exploded perspective view of an disinfection unit and tip cap assembly shown in FIGS. 48-50 in accordance with a eighth embodiment of the present disclosure.
Figure 52:
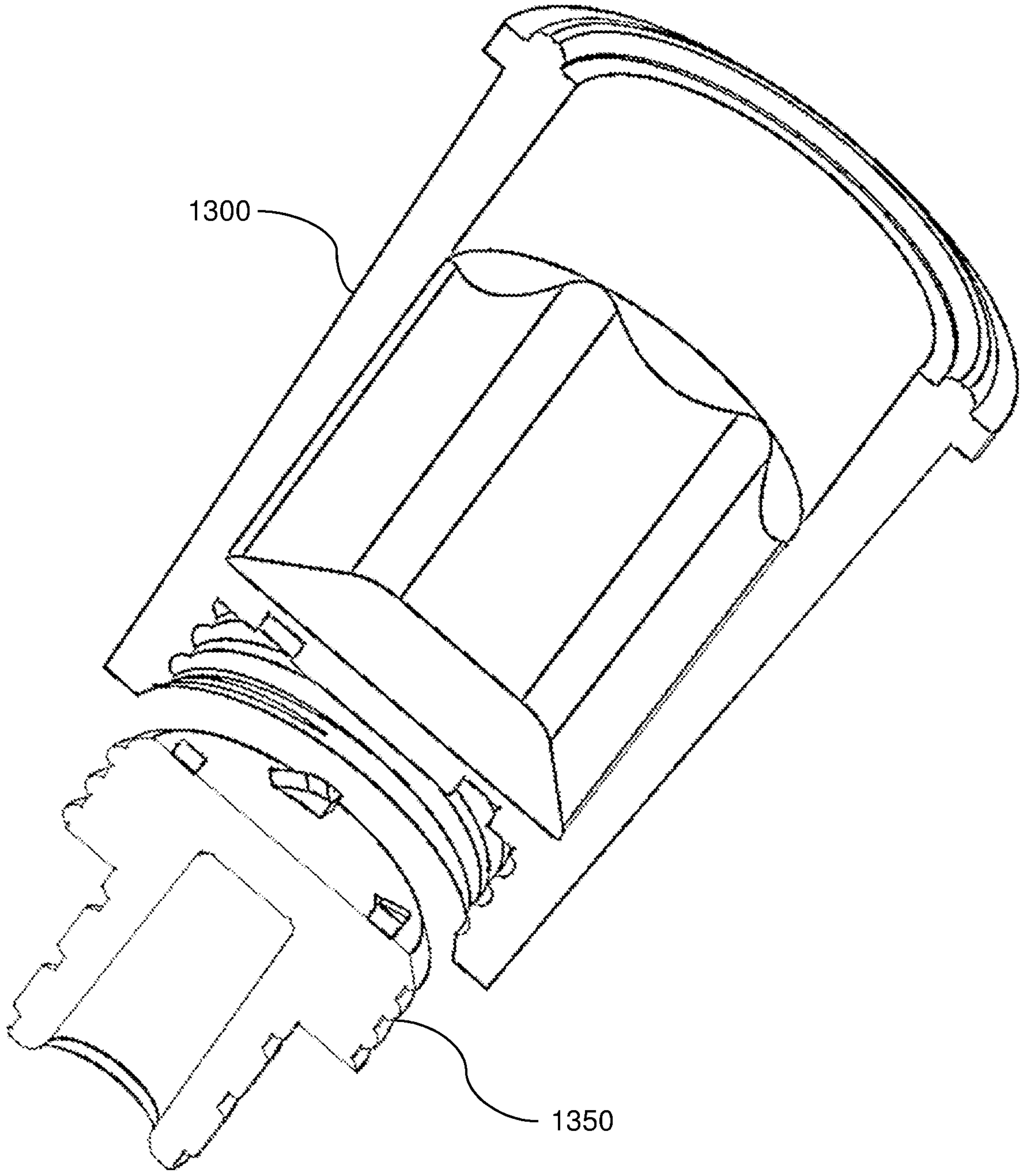
FIG. 52 illustrates an exploded cross-sectional view of an disinfection unit and tip cap assembly shown in FIGS. 48-51 in accordance with a eighth embodiment of the present disclosure.
Figure 53:
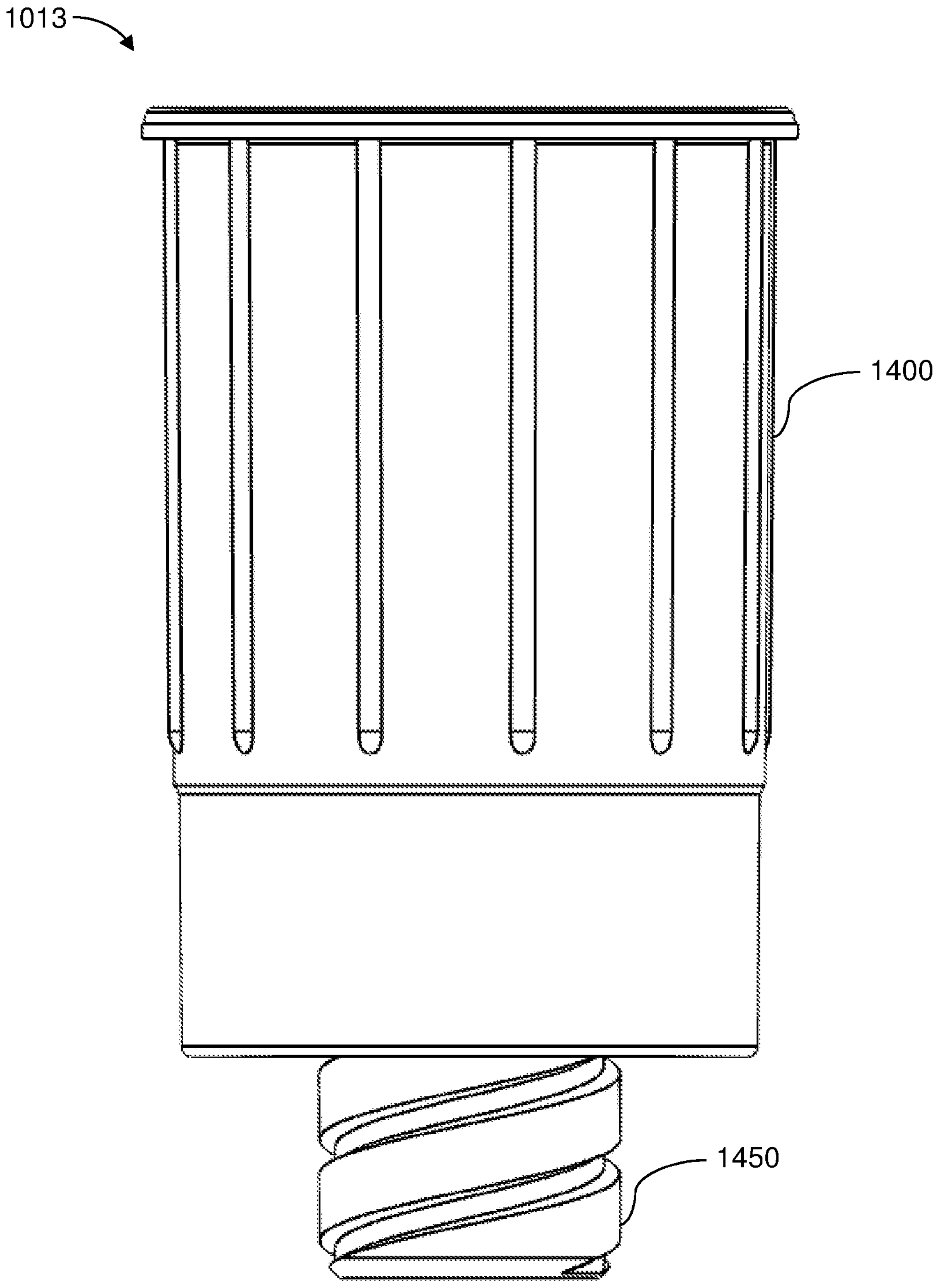
FIG. 53 illustrates a side view of yet another alternate integrated disinfection syringe tip cap assembly in accordance with an eighth embodiment of the present disclosure.
Figure 54:
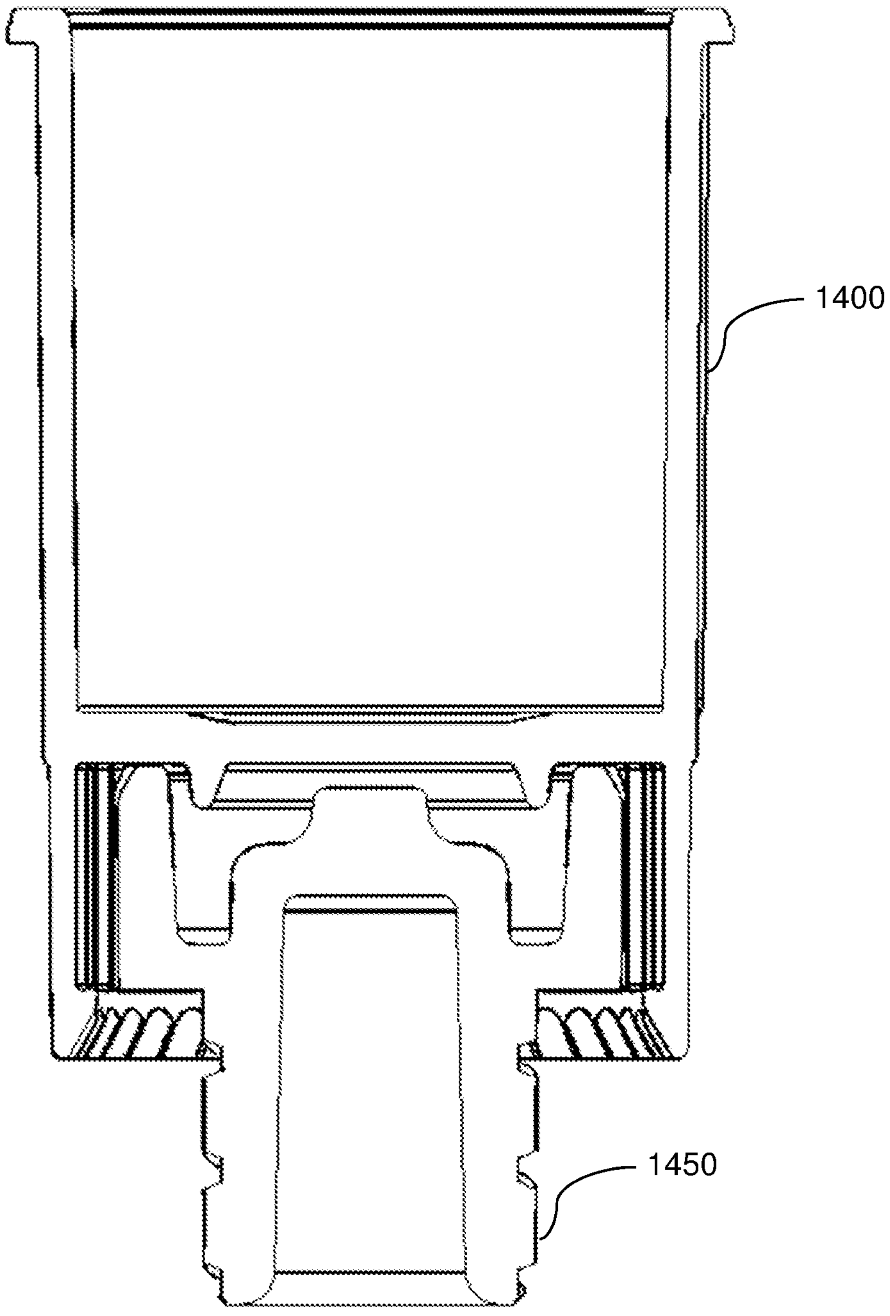
FIG. 54 illustrates a cross-sectional side view of the alternate integrated disinfection syringe tip cap assembly in accordance with a eighth embodiment of the present disclosure as shown in FIG. 53.
Figure 55:
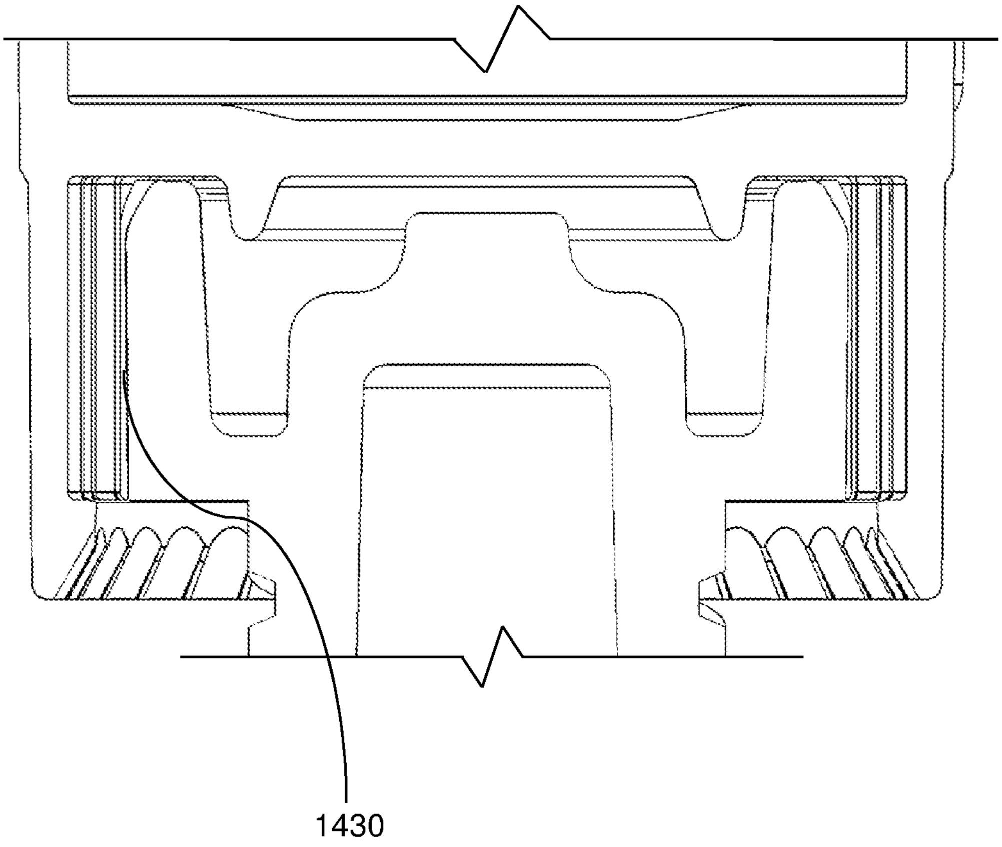
FIG. 55 illustrates a partial cross-sectional view of tip cap of FIG. 54 in accordance with a eighth embodiment of the present disclosure.
Figure 56:
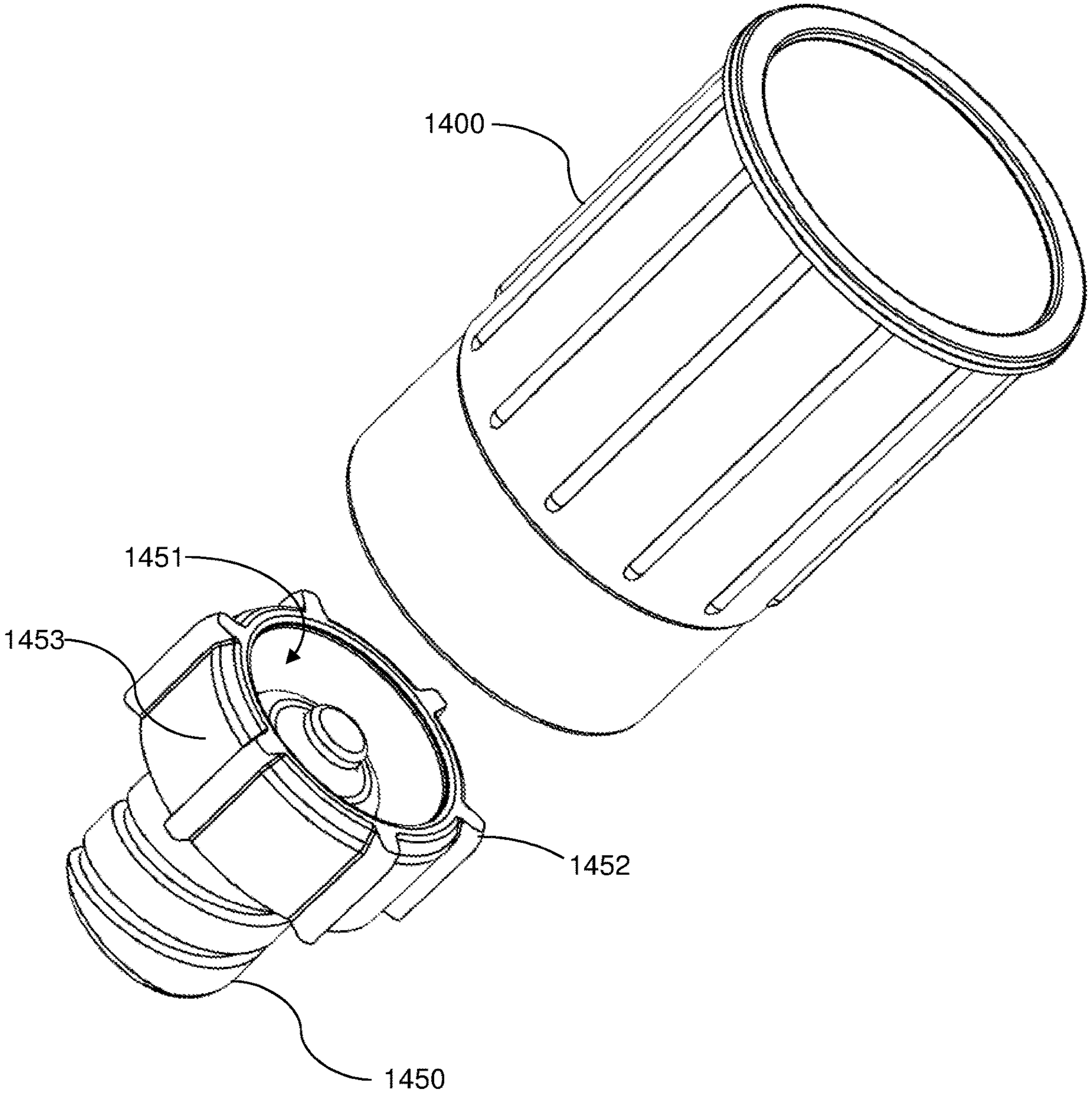
FIG. 56 illustrates an exploded perspective view of an disinfection unit and tip cap assembly shown in FIGS. 53-55 in accordance with a eighth embodiment of the present disclosure.
Figure 57:
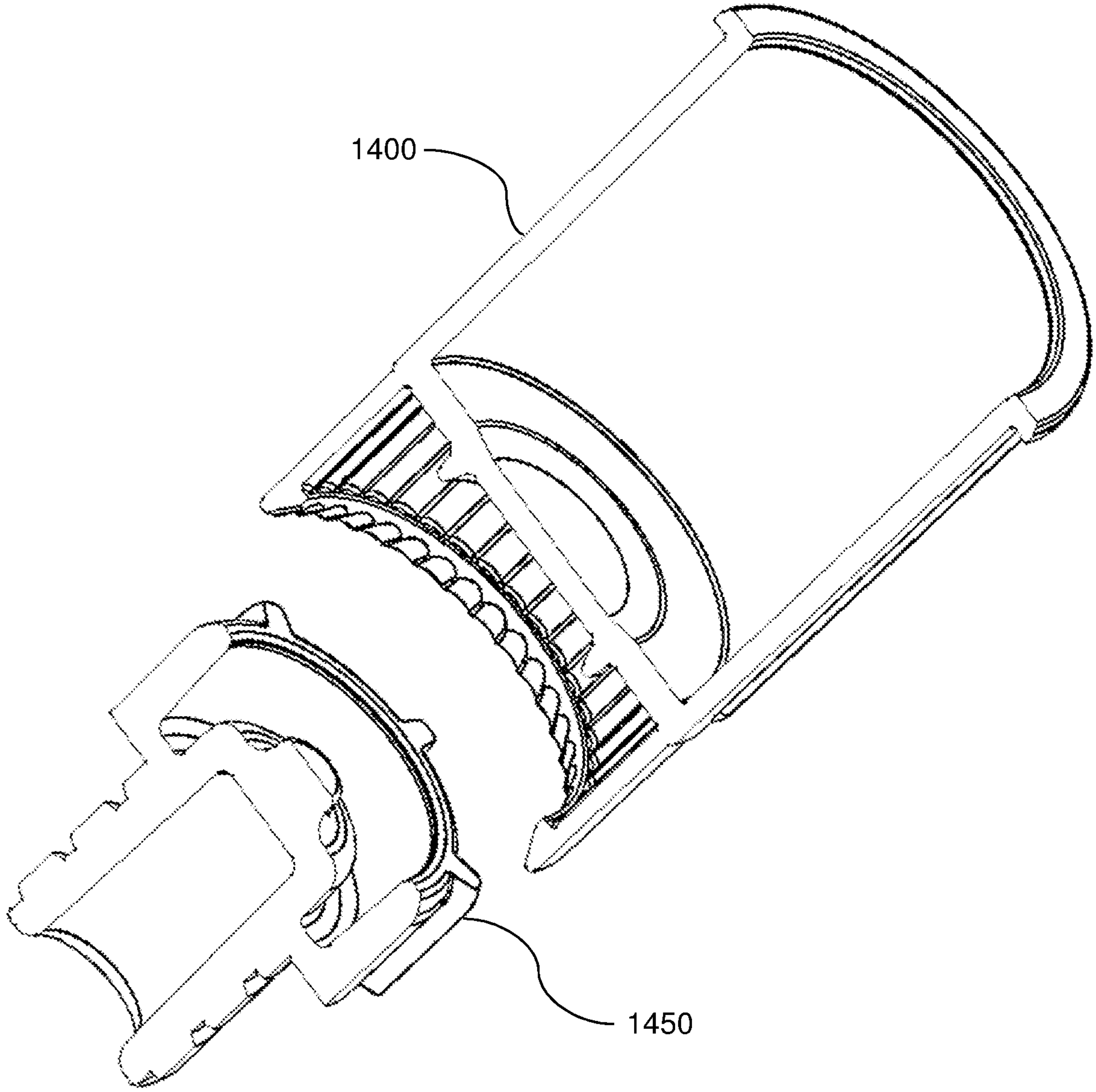
FIG. 57 illustrates an exploded cross-sectional view of an disinfection unit and tip cap assembly shown in FIGS. 53-56 in accordance with a eighth embodiment of the present disclosure.
Figure 58:
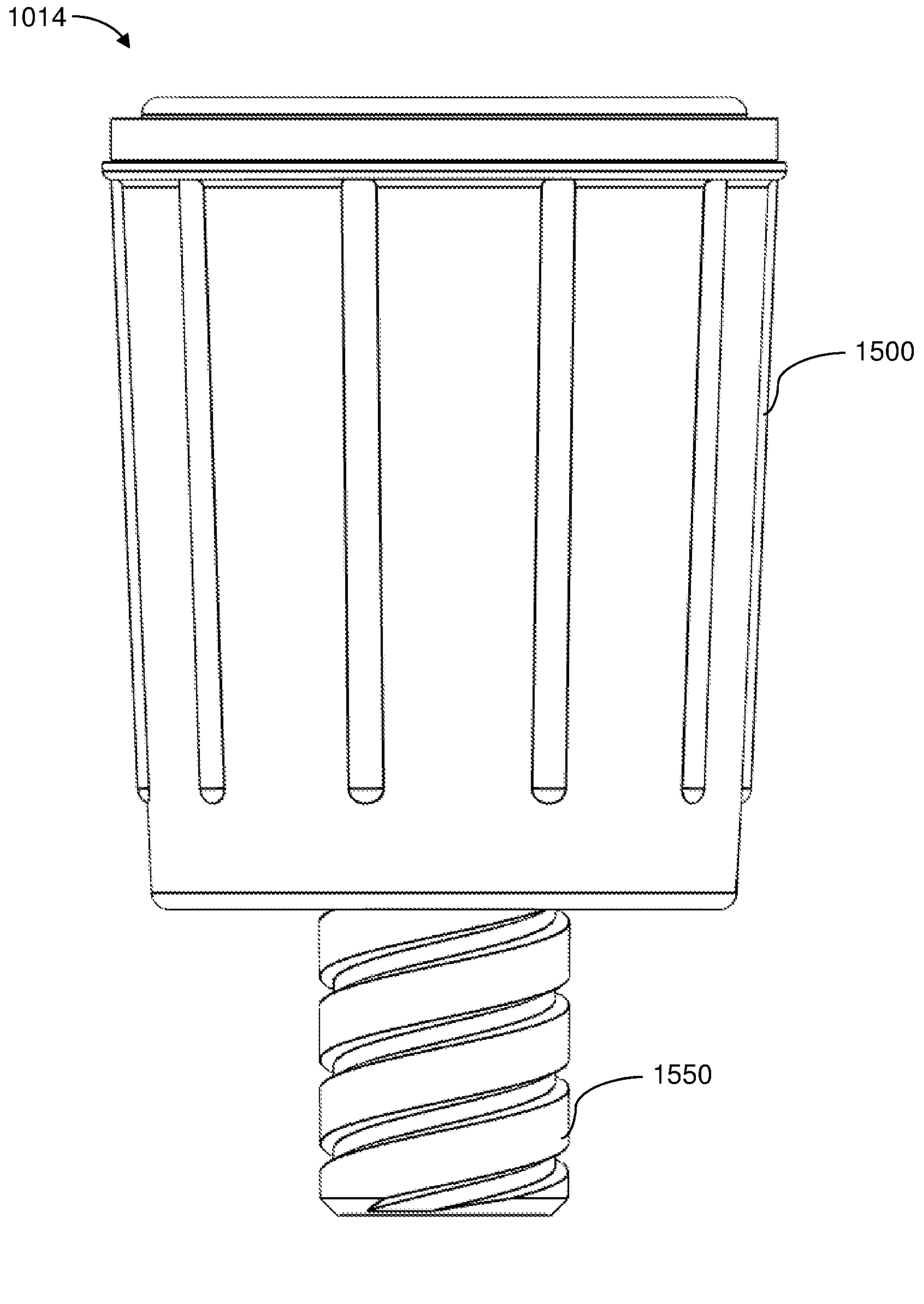
FIG. 58 illustrates a side view of yet another alternate integrated disinfection syringe tip cap assembly in accordance with an eighth embodiment of the present disclosure.
Figure 59:
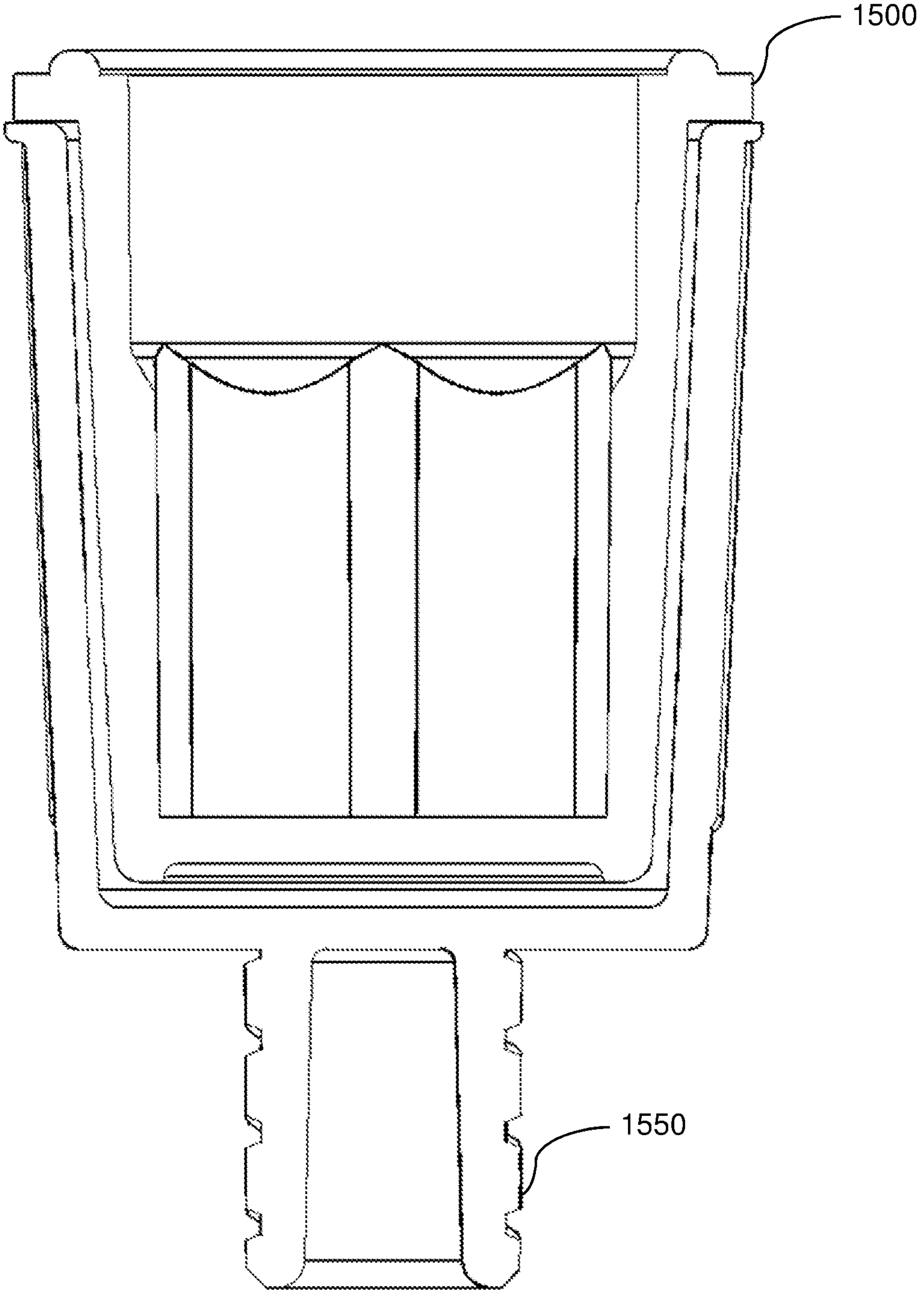
FIG. 59 illustrates a cross-sectional side view of the alternate integrated disinfection syringe tip cap assembly in accordance with a eighth embodiment of the present disclosure as shown in FIG. 58.
Figure 60:
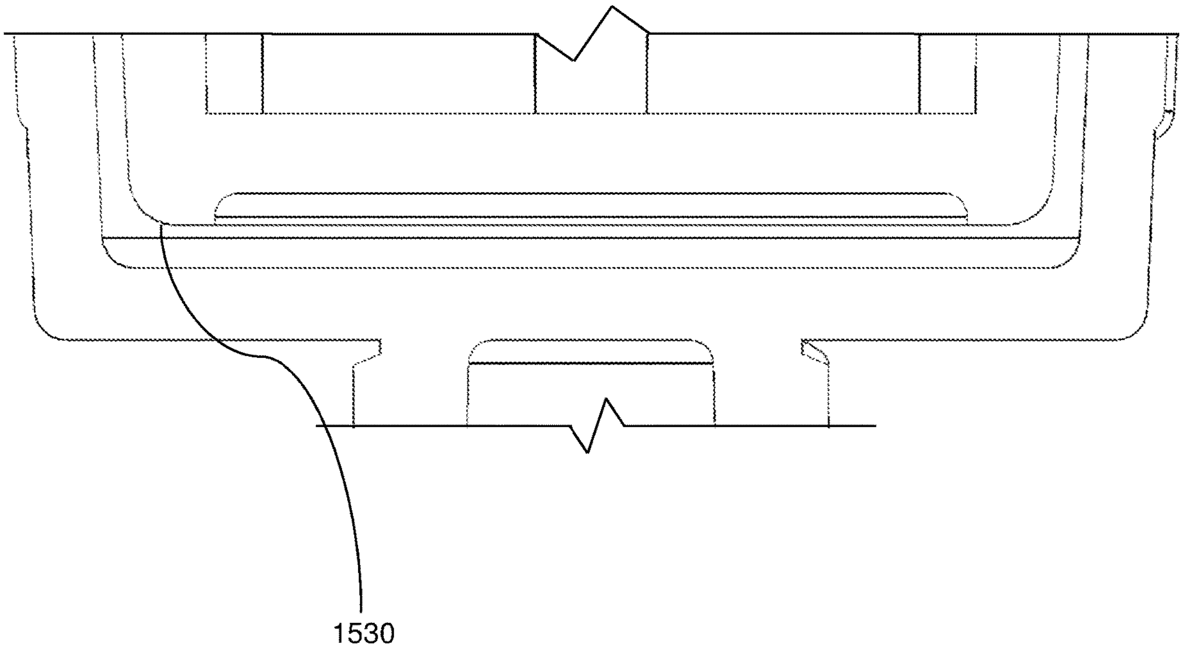
FIG. 60 illustrates a partial cross-sectional view of tip cap of FIG. 59 in accordance with a eighth embodiment of the present disclosure.
Figure 61:
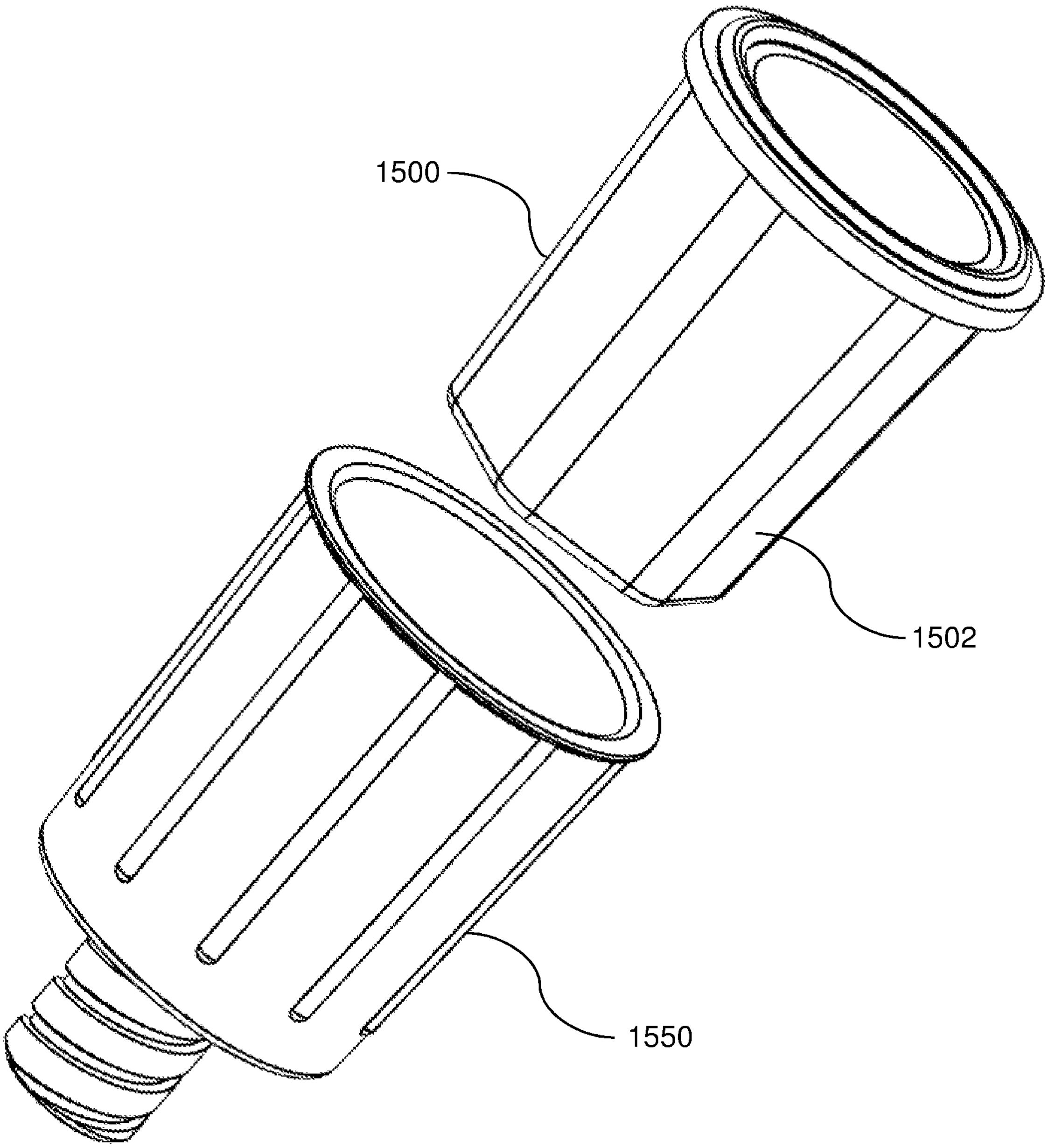
FIG. 61 illustrates an exploded perspective view of an disinfection unit and tip cap assembly shown in FIGS. 58-60 in accordance with a eighth embodiment of the present disclosure.
Figure 62:
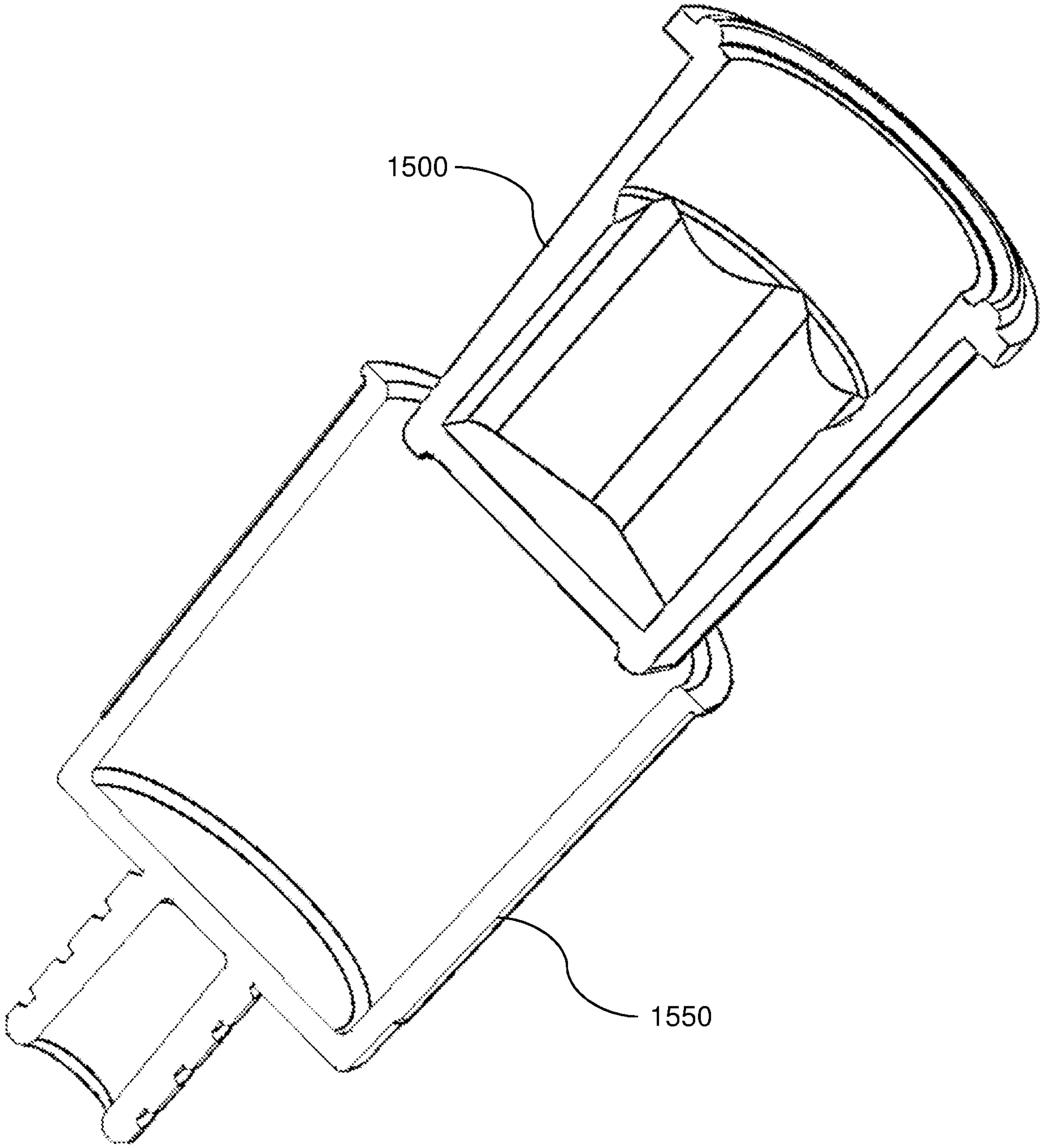
FIG. 62 illustrates an exploded cross-sectional view of an disinfection unit and tip cap assembly shown in FIGS. 58-61 in accordance with a eighth embodiment of the present disclosure.
Figure 63:
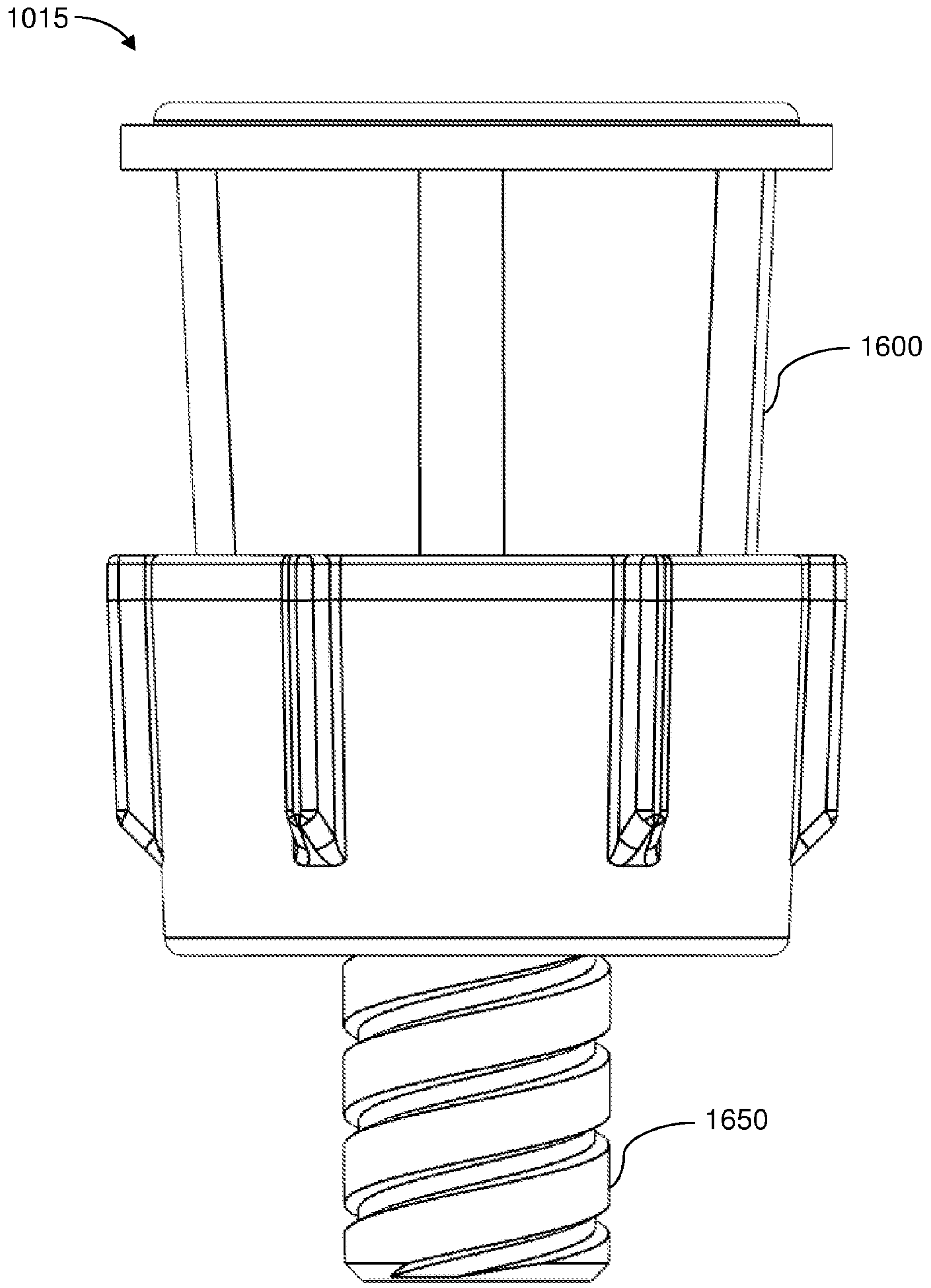
FIG. 63 illustrates a side view of yet another alternate integrated disinfection syringe tip cap assembly in accordance with an eighth embodiment of the present disclosure.
Figure 64:
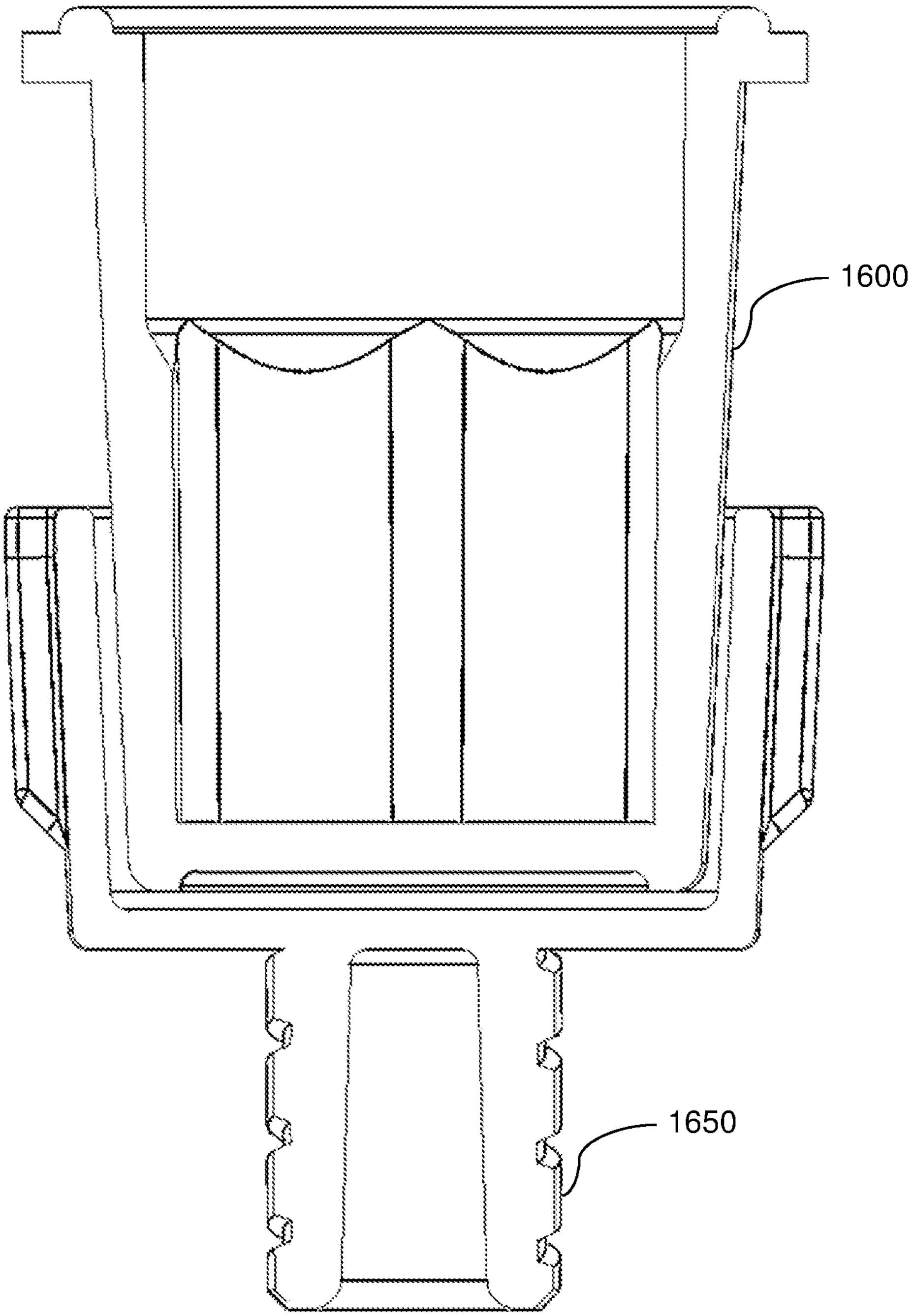
FIG. 64 illustrates a cross-sectional side view of the alternate integrated disinfection syringe tip cap assembly in accordance with a eighth embodiment of the present disclosure as shown in FIG. 63.
Figure 65:
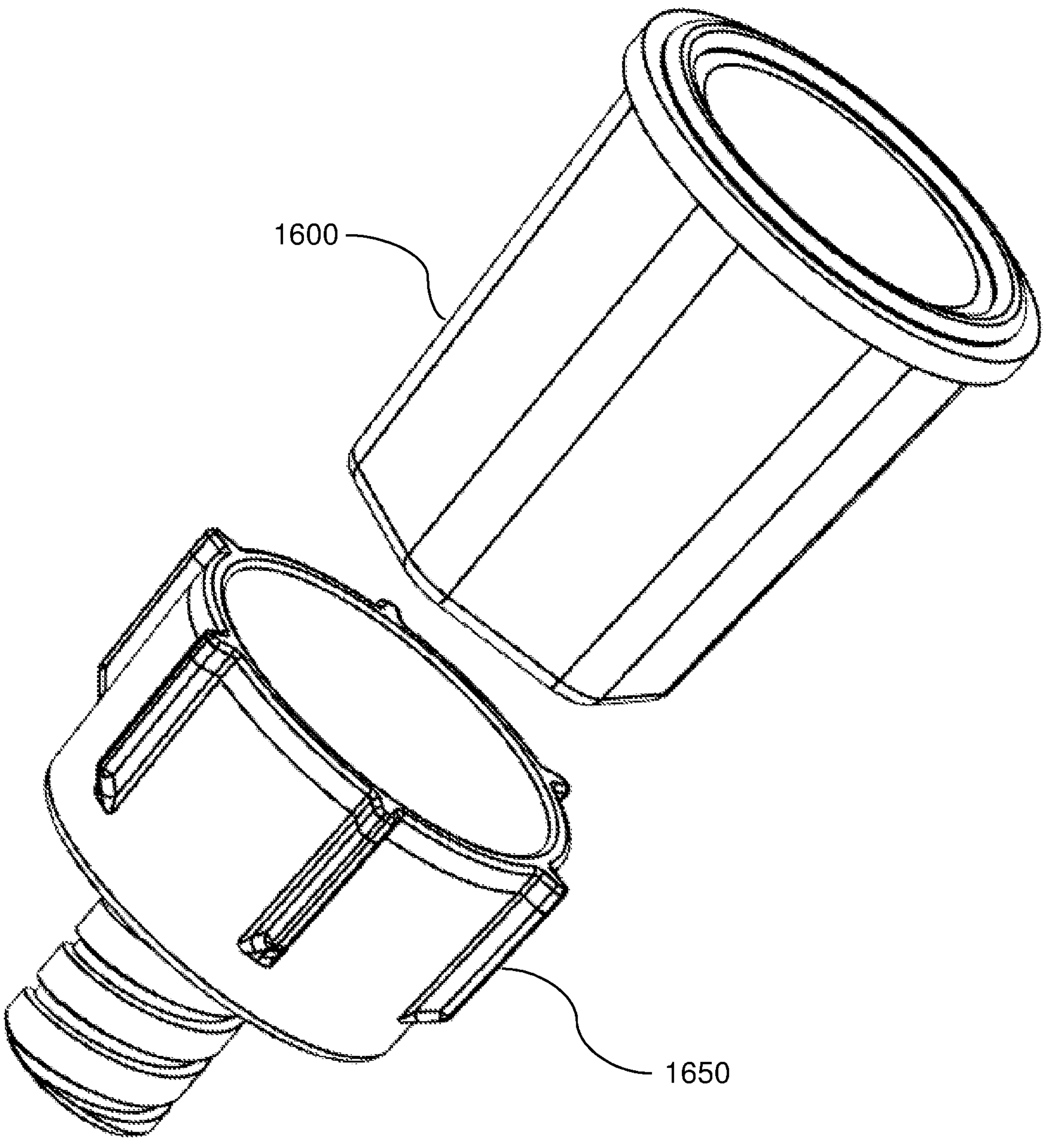
FIG. 65 illustrates an exploded perspective view of an disinfection unit and tip cap assembly shown in FIGS. 63-64 in accordance with a eighth embodiment of the present disclosure.
Figure 66:
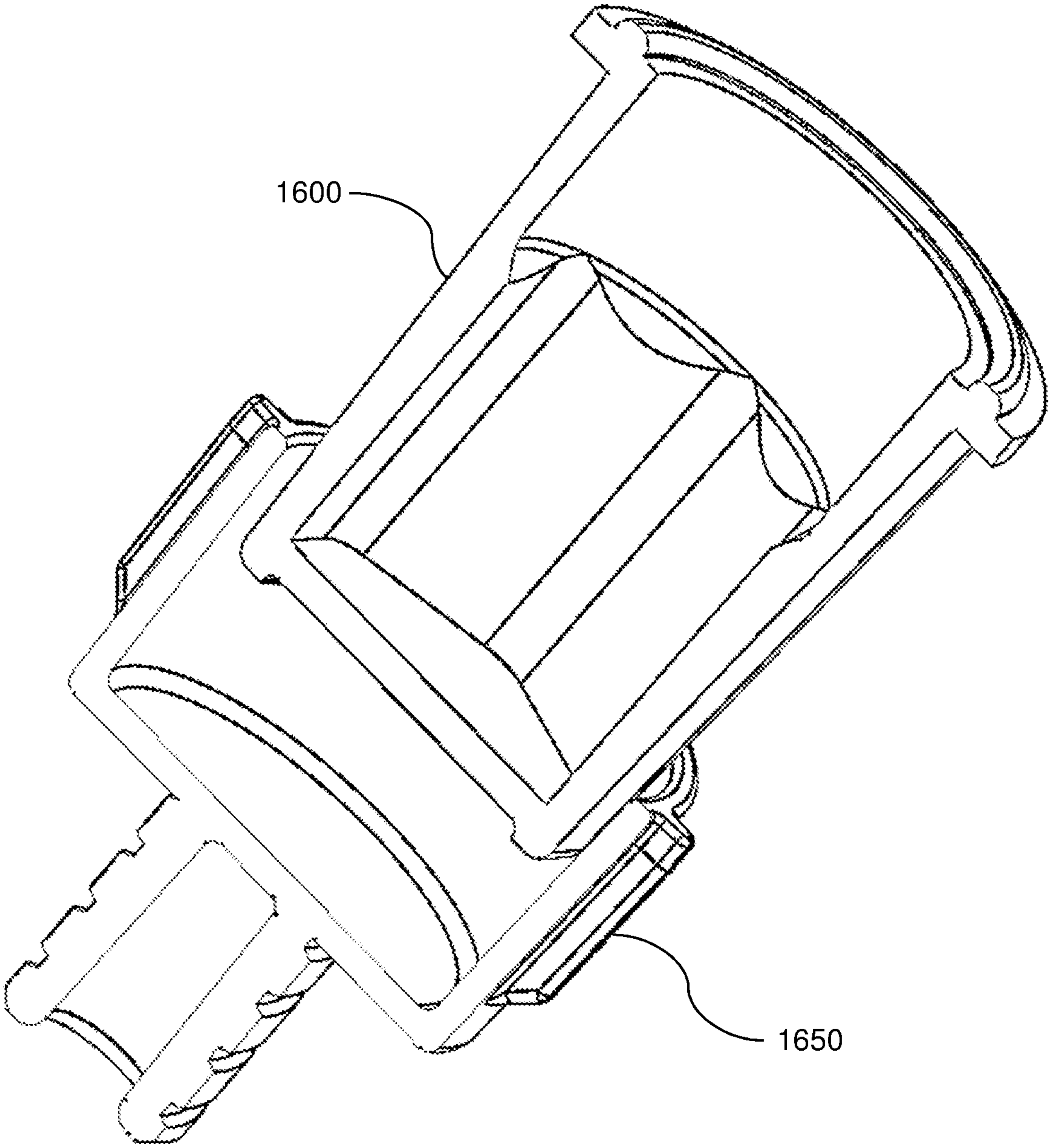
FIG. 66 illustrates an exploded cross-sectional view of an disinfection unit and tip cap assembly shown in FIGS. 63-65 in accordance with a eighth embodiment of the present disclosure.

FIG. 42 shows an alternate embodiment of the assembly 1010 of the syringe tip cap 1150 (TP) and IV access port disinfecting unit 1100 (DU) shown in FIGS. 37-41. As shown in FIG. 42, the assembly includes undercuts. The embodiment of FIG. 42 differs from the embodiments shown in FIGS. 37-41, with respect to the torqueing and anti-rotational features. As shown in FIG. 42, the torqueing feature is also disposed in the inner most diameter on the top of the cap, however, these features increase the surface area for the assembly equipment to torque the tip cap on. These ribs resemble closer to fins 1160 with complementing fins being on the underside of the disinfecting unit. Once the fins 1160 slip past each other, this ensure they can only be removed as once piece when a torque is applied.

As shown in FIGS. 43-47, another alternate embodiment of the assembly 1011 of the syringe tip cap (TP) and IV access port disinfecting unit (DU) includes a tip cap 1250 having a larger top diameter and having torqueing ribs that run along the outer diameter. The tip cap 1250, as shown in FIGS. 37-41, is a female as it catches and wraps around the disinfecting unit during and upon assembly. As shown in FIGS. 43-47, the anti-rotational features 1251 resemble a picket-fence. As the tip cap (TP) and IV access port disinfecting unit (DU) are assembled, the ribs on the disinfecting unit 1200 shall fall into the grooves 1252 between the fence-like anti-rotational features 1251, both self-aligning the part and preventing it from rotating independently. Once the undercuts 1230 of the tip cap 1250 clear the base of the disinfecting unit 1200, the tip cap (TP) and IV access port disinfecting unit (DU) shall snap together, making disassembly difficult. Additionally, the ribs 1253 on the tip cap 1250 have a specific geometry that allows the component to be molded in a split mold, which significantly eases the demolding process.

As shown in FIGS. 48-52, another alternate embodiment of the assembly 1012 of the syringe tip cap (TP) and IV access port disinfecting unit (DU) includes threads 1352 on the tip cap 1350. Additionally, there are four anti-rotational slots 1331 on the bottom top surface 1355 where the threads are located. The tip cap 1350 features a threaded outer diameter 1352 on the top half of the device and anti-rotational lugs 1353 that are both used for assembly and to lock the devices together as they are being threaded on one another. As the disinfecting unit is threaded on the tip cap, the locking lugs 1353 will slip past the bottom surface of the disinfecting unit and into the locking slots 1331. The thread ensures mechanical stability against forces while the lugs and slots ensure both components are removed together as a torque is being applied.

As shown in FIGS. 53-57, another alternate embodiment of the assembly 1013 of the syringe tip cap (TP) and IV access port disinfecting unit (DU) includes a tip cap 1450 and a disinfection unit 1400. The ribs 1452 on the outer diameter 1453 serve the purpose of torque assembly, locking, self-aligning, and anti-rotation. The disinfecting unit features a "racheted" undercut 1430 that first aligns the parts and then locks them together once the undercut clears the ribs 1452 on the tip cap 1450 and wraps around them. Once fully assembled, a "racheted" sidewall in the cup locks on to the torqueing ribs ensuring the parts do not rotate on one another.

Figure 67:
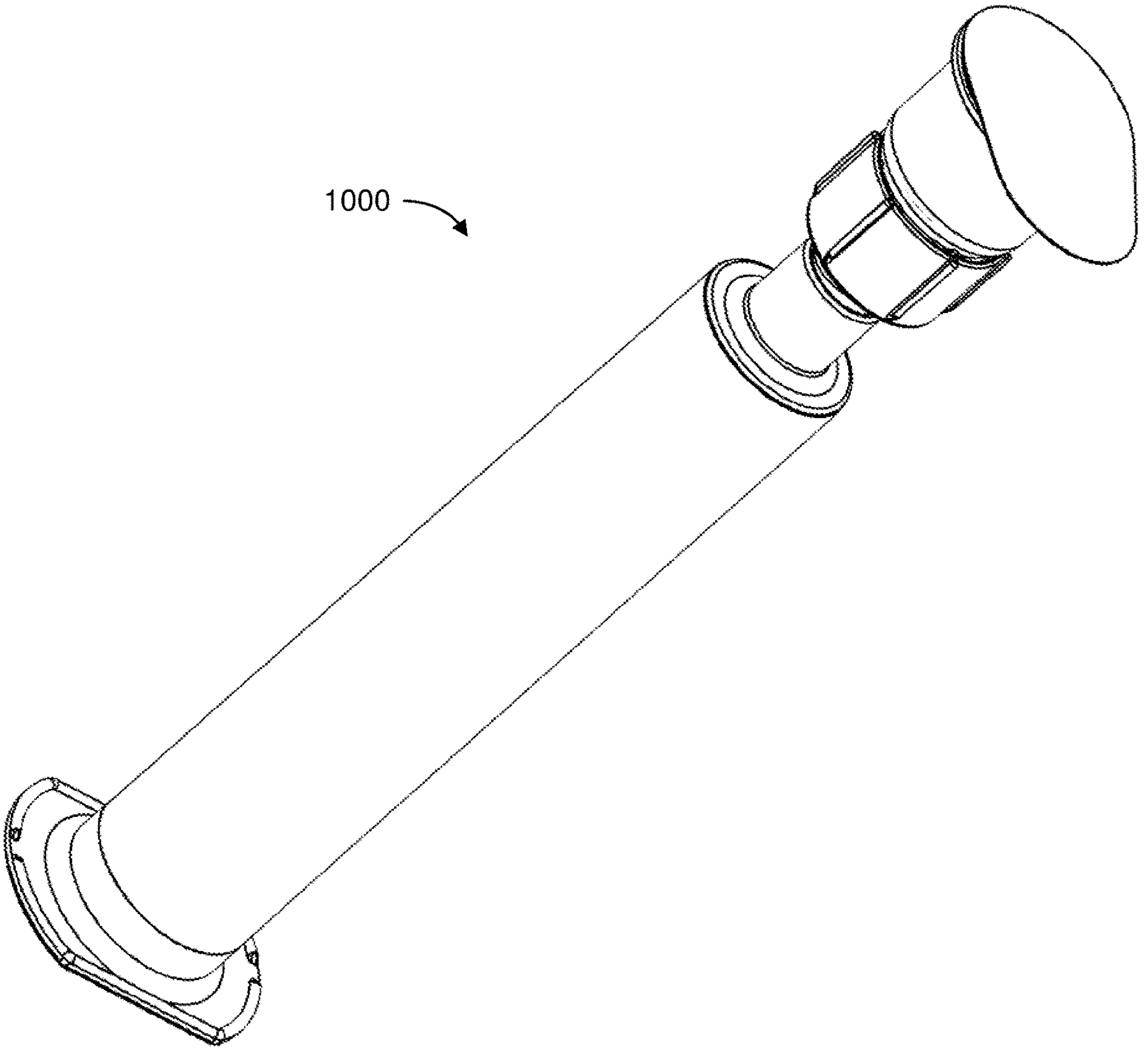
FIG. 67 illustrates a perspective view of an assembly of the integrated disinfection syringe tip cap assembly shown in FIGS. 63-66 in accordance with a eighth embodiment of the present disclosure; and, FIG. 68 illustrates an exploded view of an assembly of the integrated disinfection syringe tip cap assembly in accordance with a eighth embodiment of the present disclosure.
Figure 68:
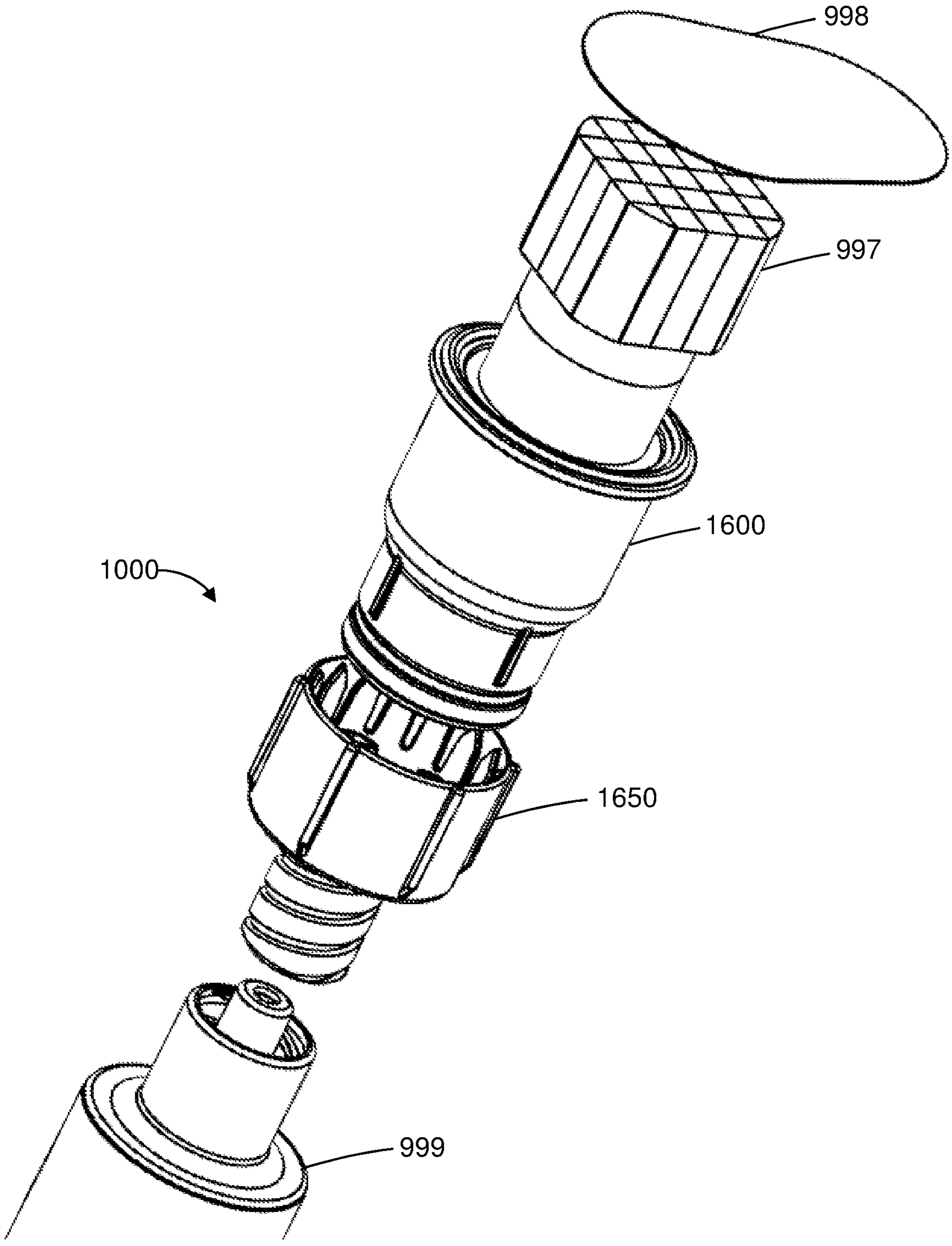

As shown in FIGS. 58-66, another alternate embodiment of an assembly 1014 of the syringe tip cap and IV access port disinfecting unit includes a tip cap 1550 having a similar geometry to the tip cap shown in FIGS. 43-47 in terms of its outer diameter and torqueing ribs, however there are no undercuts or specific anti-rotating features to keep them together and keep them from spinning. The tip cap and IV access port disinfecting unit are mated utilizing a locking taper and rotation is prevented due to their competing geometries. The disinfecting unit's 1500 outer shape is a hexagon, while the tip cap's 1550 inner diameter is a circle. As shown in FIGS. 58-66, the height of the tip cap 1550 runs along and covers at least a portion of the side wall 1502 of the IV access port disinfecting unit 1550. As shown in FIGS. 63-66, in an alternate embodiment, the height of the tip cap 1550 covers only about half of the side wall 1602 of the IV access port disinfecting unit. FIGS. 67 and 68 are shown an assembly 1015 of the device shown in FIGS. 63-66.

In one or more embodiments shown in FIGS. 34-68, mechanical locking is achieved by use of undercuts, interference fits, and locking tapers.

In one or more embodiments shown in FIGS. 34-68, anti-rotation is achieved by use of ribs, fins, and channels (created by "racheting" and "picket-fencing").

In one or more embodiments shown in FIGS. 34-68, automated or universal alignment is achieved by used of channels and chamfers.

In one or more embodiments shown in FIGS. 34-68, a syringe assembly includes a tip cap with an integrated disinfecting unit attached to the top of it, which are designed to withstand forces experienced during normal use.

In one or more embodiments shown in FIGS. 34-68, the mechanical mating and assembly features ensure that the device can be assembled in an automated process and ensure device integrity during transport, use, and over the course of the product's shelf life.

Compared to separate flush syringe and disinfection unit products that are currently available, embodiments of the integrated disinfection unit of the present disclosure provides easy access to the disinfection product at each flush and easier hand operation during disinfection followed by flushing.

Embodiments of the integrated disinfection unit of the present disclosure provides numerous advantages including, but not limited to: 1) the syringe unit closed with the cap and the disinfection closed with a peel-off foil cap can be individually sterilized because the two units currently available may not be compatible with the same sterilization method or could sufficiently be sterilized with identical sterilization parameters; 2) compared to using an adhesive to join the two sealed units, embodiments of the integrated disinfection unit of the present disclosure eliminate the cost of adhesive material and application; 3) embodiments of the integrated disinfection unit of the present disclosure eliminate the risk of leaching of the adhesive material into the two closed units; and 4) in certain embodiments of the integrated disinfection unit of the present disclosure having locking tabs, the locking tabs are annular and structurally more robust and are easier to mold.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as disclosed.

What is claimed is:

1. An integrated disinfection device comprising:

a cup having an integral body, an annular wall having a length extending from a closed end to an open end defining a chamber; the annular wall having an exterior wall surface and an interior wall surface;

a plurality of alignment teeth disposed on the annular wall;

a plurality of inward protrusions disposed on the chamber of the cup adjacent to the interior wall surface;

a plurality of locking tabs;

a cap having an integral body, an annular wall having a length extending from a bottom end to a top end defining a chamber; the chamber is appropriately sized to adapt to the annular wall of the cup;

a plurality of alignment teeth face disposed on the interior wall surface of the annular wall;

a mating surface dispose on the chamber; and a locking hole disposed in the center of the mating surface.

2. The integrated disinfection device of claim 1, wherein the locking tabs are perpendicular to a plane coincident to the closed end of the cup.

3. The integrated disinfection device of claim 1, wherein the locking tabs comprise a harpoon-shaped lip.

4. The integrated disinfection device of claim 1, wherein the locking tabs are disposed in the center of the closed end.

5. The integrated disinfection device of claim 1, wherein the alignment teeth are spaced evenly along the interior wall surface of the annular wall.

6. The integrated disinfection device of claim 1, wherein the cap includes a connection element.

7. The integrated disinfection device of claim 6, wherein the connection element is a luer slip connection.

8. The integrated disinfection device of claim 6, wherein the connection element is a luer lock connection.

* * * * *